United States Patent [19]
Williamson et al.

[11] Patent Number: 6,114,605
[45] Date of Patent: Sep. 5, 2000

[54] MI NUCLEIC ACIDS AND USES THEREOF FOR CONFERRING PEST RESISTANCE IN PLANTS

[75] Inventors: Valerie M. Williamson, Davis; Isgouhi Kaloshian, Grand Terrace; Jafar Yaghoobi, Davis; John Bodeau, Davis; Stephen B. Milligan, Davis, all of Calif.

[73] Assignee: The Regents of the University of California, Oakland, Calif.

[21] Appl. No.: 08/947,823

[22] Filed: Oct. 9, 1997

Related U.S. Application Data

[60] Provisional application No. 60/028,191, Oct. 10, 1996.
[51] Int. Cl.[7] .............................. A01H 5/00; C12N 15/29; C12N 15/82
[52] U.S. Cl. .................................... 800/317.4; 435/320.1; 536/23.6; 800/279; 800/287; 800/298; 800/301
[58] Field of Search ................................ 435/69.1, 320.1, 435/419, 468; 536/23.6, 24.1; 800/279, 301, 317.4, 287, 298

[56] References Cited

U.S. PATENT DOCUMENTS 5,608,144  3/1997  Baden et al. ............................ 800/287

FOREIGN PATENT DOCUMENTS

WO 95/18230  7/1995  WIPO ............................ C12N 15/29

OTHER PUBLICATIONS

Lagudah, E., et al., Map–Based Cloning of a Gene Sequence Encoding a Nucleotide–Binding Domain and a Leucine–Rich Region at the Cre3 Nematode Resistance Locus of Wheat, *Genome*, vol. 40:659–665 (Oct. 1997).

Cai, et al., "Positional Cloning of a Gene for nematode Resistance in Sugar Beet," *Science*, vol. 275:832–834 (Feb. 7, 1997).

Staskawicz, et al., "Molecular Genetics of Plant Disease Resistance," *Science*, vol. 268:661–667 (1995).

Salmeron, et al., "Tomato Prf is a member of the Leucine–Rich Repeat Class of Plant Disease Resistance Genes and Lies Embedded with the Pto Kinase Gene Cluster," *Cell*, vol. 86:123–133 (Jul. 12, 1996).

Ori, et al., "The 12C Family from the Wilt Disease Resistance Locus 12 Belongs to the Nucleotide Binding, Leucine–Rich Repeat Superfamily of Plant Resistance Genes," *The Plant Cell*, vol. 9, 521–532 (Apr. 1997).

Mindrinos, et al., The *A. thaliana* Disease Resistance Gene RPS2 Encodes a Protein Containing a Nucleotide–Binding Site and Leucine–Rich Repeats, *Cell*, vol. 78:1089–1099 (Sep. 23, 1994).

Bent, et al., RPS2 of *Arabidopsis thaliana*: A Leucine–Rich Repeat Class of Plant Disease Resistance Genes, *Science*, vol. 265 (Sep. 23, 1994).

Grant, et al., Structure of the Arabidopsis RPM1 Gene Enabling Dual Specificity Disease Resistance, *Science*, vol. 269:843–846 (Aug. 11, 1995).

Lawrence, et al., The L6 Gene for Flax Rust Resistance is Related to the Arabidopsis Bacterial Resistance Gene RPS2 and the Tobacco Viral Resistance Gene N, *The Plant Cell*, vol. 7:1195–1206 (Aug. 1995).

Whitham, et al., The Product of the Tobacco Mosaic Virus resistance Gene N: Similarity to Toll and the Interleukin–1 Receptor, *Cell.*, vol. 78:1101–1115 (Sep. 23, 1994).

*Primary Examiner*—Amy Nelson
*Attorney, Agent, or Firm*—Townsend and Townsend and Crew, LLP

[57] ABSTRACT

The present invention provide Mi nucleic acids encoding Mi polypeptides which confer resistance to nematodes and other pests. The Mi nucleic acids can be used to produce transgenic plants resistant to these pests.

34 Claims, 1 Drawing Sheet

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 51952 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
AAGCTTAGGG TATTGTTCAA GTTCCAACCT GATTCCACAT ATTCTGGACA TGCAGTTACA      60

TCCCGTGGAT TGGTTTTAAG TGGAAAACCA CTTTGGCTTG CACTAGTTTC CGTAGTATTC     120

CCATGGAGCA CCTAATAAAC CAAATTGAAA ACGAAAAGTA AGAAAAAATG ATGGAAAGAA     180

AAAAAAATTT GGCAGATCCC TAGAAAAGAA AATTGCAATT CCAGAAGAAA ACCTCNATTT     240

CTTCAGTTGG ATTCTCAATA ATTCCTCCAG TATTCCCCCT TCAATATCAC GAAATAGATG     300

GTTCTGAACA GCATCTGCGT TGCATCTGAA TTAAAGTTTG AAGCTGTGAT CTGATCTTCC     360

TTGACAAAGT ACTGCCTCTT GAAATGATCA GCGTAATTCT TGAAAGACTT CAACTTAAAC     420
```

```
TTTGGCCCAC TTTTAAATTC AAAGTGTTCA TTACAACAAC CAGATTCTTT AAGTTCCACG      480

GTGTGTCCAA ACTCTGGCTT CATACTTGGA ATTTTCTGCC GTCTATTATT ACTCTTCTTA      540

TGGGCTCCCT CAAGTCTCAT CTTTAAAAAC AGACTCTGGA GGTCACTAAT GCGCTGGATA      600

CGAGTGTCGA CTCCACACCT CGTGTCCTCT TCTTCAATGC GGCAAGGTGG TCTCCAGGAA      660

GAGGGAGGAA CAATACGGCA TACTCCATAT TGCTTGACAT GTGGAAGGAT GCTTGCAACA      720

TACTTGAGAG TATCTTTAAA TTCCTAGCAT AAGATTTAAC TTCATGAAAG CAGAATGTGG      780

CAGGGTACCT GTTCATGATC CAATAGAGGG CATATACCAG GCTGAAAGAA AGATGGGAGT      840

GTTAAGGAAT ACCTCTTCAG TAGGATGGAG TACAGGAGCT TCATCAAGTG AAGGGATCCG      900

TGCCGATTCC GGACAACTTC TTGCAATAAC CTTTTGAAAA TGCATACCAC AAACATCATA      960

AGCTCAATGT AAACTGAAAA AAATAAATAA CAAGACAGAT GATCGCAATA ACTTTTGGAT     1020

AAAGAACATT TAATCCTTGC CTTGAAACCA AACATTATAC AATATTAAGG AAGAATGAAC     1080

CTTCTGGCAG TTGTGACAAC TGGAACATCC ACGGATCACT CCTCTGGGAA GATAAGCGCG     1140

TGAAGACGAA CCCTGAAAAA TAAATTCAAC CCAGAGATAA TCAAATGACC AAACCATTAT     1200

TCTAACTAGC AGTGCCACAA GCCAACAATT ACACAGAGAA ACAGTATATG CTGCCACATT     1260

CTTTGACCAG CCTCTACAAG AGAAGATGCA ACCGAGAGGC CTCAGGCTCA GTAGATCAAT     1320

GGGCAGCCCT TAGCTTACAA CTAATGTATG AGACAATCAA ATGAAAAAAA GTATACCTGT     1380

AGAGAAACAG GAAAGAAAAT CATCCTTGAC CAATACTCGG AGCACACACT CCAAGATTTA     1440

TGTCTTAATA AAGCCCATCA ACACAGTTAC AGTGTCCTAC ATTGATTGAG GGAATTGATG     1500

ATTGTCCCCT TATATTGTTT TGGACAACCC TCACCTAATG GGCTACCATT TTATGTTTGA     1560

CTTAGGCTCA AAGTTCATTT TCTTAACATG GTATCAAAGC CATACATCCT CTTGTTGATT     1620

TGTTTGGGCA TAATATTATG TCATCCATGC TCCAAATGGC CATGGTTAGG AACACAAGGG     1680

ATTGTTGGAG TCCCACATAT GTTGAGGGAA AGGGATGTTG TCTTATTATA TGATCTTGCT     1740

CTCTTGGACA ATTCCCTATT TAATGAACTT CTTTTCGAGG TAGAGTTAGG CTCAAAGTAC     1800

ATTTTCTTAA CAGGCACATA TTATTAGGAT TTAGGAGTAG TTAGTACCTC TCATTTCATA     1860

ACCAGAGAAG AGCTAACTTA ATAGTACAAG CTTTTGAGGA ACGTAGGTGG ATAGTATGGG     1920

CGATCAGGGC TGAACATCCA GGGACACTAC GATTCAGATT TAAGGTTAGG TCCATATATA     1980

TATACTTCCA TATTAACTAC TGTCTACATA TACTAGTTCC CTTATTGACA AGTAAAGGAG     2040

CAAAAGAATT CACCATTTGG CCCGTCCCCT GTATAGTGCG GGACAAACAG AGAATAAAAC     2100

CTTATCAGTA GATACAACTT TTCTCTCGAT AAATCAAAAA GAAAATTCAT AAATGTGCAA     2160

GAAGATGATG CAAGGGTTAG TAGGTACAAA TGCTCAGTTG TAGAGCTCCC AAAGAACTAT     2220

CCACCCCTTT ACATATCCTC CTTTTCTTTC CTTATTTAGC TTAACTTCCA TGTTGCAAAG     2280

GCATATATAG CCCCAACTGA TTTGCCATCT CCGTGGACGC AATGTTATCG AAACTCCCAG     2340

CATCGATGAT TATCTTTGCA CCGGCCAATT CTGACATAGA TTTTGAATAC AGCCTTCCGT     2400

CTTCTCCTCC TTTTCTGCTGA CGTTGGCTCA TGTTGATACA CAATCTAATG ACAGTGAAAC     2460

TATCTCCTGT CCTGAGCTTG AGAACCCCAG CTCAAAGGGT AATACCCATG ATATATTGAA     2520

CACGACAAGA GTCAACTCG GCTCCAGTGC GATAATGAAG AAACATAAGA GGGACTTCCC     2580

TTTCTTTCTA GCGCATACAA CAGTAATTCA GGTTTATACA AACCTTTCTT CTCTAAATAG     2640

TGTCTCACAC AGCATACTAT GCAAAGGAAA CCACTTTTCT GGTTCTGACT TACAAACATA     2700

TTTTCAGATA CCTCTAGCAA GATTGCACTG CAAAGCAATC ACATTTTGCA CCAGGGCCTT     2760
```

-continued

```
AACATACCAT TCTGTCCTCA TCTTGCTATA CCACTTGGCC ATAAATATGA AATATCTTGA    2820

AGAAATACTC CATTTCTTCC TACTTCTAAT CACTTGACAG TTGACACCAG TGTTATCAAA    2880

GGCGCGCTTA AGCCCTTAAG CGAGGCTCAA ATGTGTTTGA GCGCTTCGCC TCCCTTTATG    2940

TGCGCTTCAA TGTCGTCATC AAGGTTCTAA GACAAATGTT TCCTTGCCAA TGAGCTTCGC    3000

ATGAAGACGT GACACTAAAT AATAGATATT TTACTTTATC ATAAAAAAAA TTCAATTTCT    3060

TTGGTCATAT ATTTGACATT CATTTTTATA ATTATTAATT TTGGACTAAA CATATATATT    3120

TGTACTCTTT TCTCCCTTTG CGCTTTTTTT CATTAATGTC CACGCTTAAT TTGCGCTTAA    3180

AGCCCTCACG GACTTTAGAG CTTTTTTGCG CTTTTCGCCT TTGATAACAC ACTTGACACA    3240

ACTTTCTTTT TGATGACTAT GGTGTCTGGG CCAATTTGTA CGCACCTCGA CTAATTCCAC    3300

AAGATATTTG CCACTTCCTG CCAGTGCAGG TACGGTAACT CTGTCCACTA AGGCAAGGAC    3360

AGATGAGAAG AAATCGCCCA GTGTTTTTGT CCGTTAACAG TGTTCATCTT GTTCCAAGAA    3420

CACAAGGATG CATATGGTCA ACAGGAATAA TCCTCGGTAA AGCCCAAAAA TATTATCCCT    3480

ATATGCATCT CTCACCAGAT ATGTTTATCT CATATGGTCC AACCAGAAGC ATCAGCTGTG    3540

GACTTCACTC TTCTTTTCCT GCCTTCTCAA TAAACACCAC AAGGGGAATT CTTTTACAGC    3600

AGTGTACATA TTGATGGTGA GACAAAATCA AAACTTATAG TTCAATCAAT TTAATTGAAA    3660

TCCATCATTA ATATGTTGAT GCTACGTATG GAAATAAAAA AAAAAGGATT TATGAGAAAA    3720

TTTTATGAAA ATCTTACTGA CCTTATCAGA TTCACATTCA AAATTCTCTT CCATGTGATC    3780

AACATGATCA TCAAGTATCC AAGGCCTACG CCTAACAGAA CTCTTAAGCT TTCCTGTGCT    3840

AATAATTGTT GCTGTAGAAG CAACCTGGAC AGGACCTTGC TCAGACTCAT TCCCAACAGC    3900

CACAGAGTTA CAGGCTTCCT CATTATTTTC TACCTTCTGT AGTGTGAAAG ACGTTAGTGA    3960

TTCAAAACCG GGTGGAACTG AAAATCTTTT CCTGTCGTCA CATTCACCCT GTAATCTGAT    4020

GCGCTTGGCC CCCATTAACA CCAAGACAAA ATAGCACTGG AACAAAGAGC TTAAGTATTA    4080

GTGGACATGA AATGTGACAT GGACCTACTT TGCCTTCTAA GGAAGAAAAT AACCAAATAC    4140

AGGCATGCTT CATCAATGTC CATGTAAGTT GTACCTCTTA ACTTCACCTT TTATACTGTC    4200

AAGTACAATT AGACATCGTC TGTGAGAACT TCAGAACTGA CCTGCAACAA GAGAACACAG    4260

ATTAAAGGGT AAATACTAGC CAATATGAAT ATAGTCAAAG ATAAAGTAAT CTGTATACAG    4320

ATACAAAAGA CTAAAGTAAT AAAAGAGGAA TTTGGTCGTG CCTGGTATTT TAAGGTCAAT    4380

AAAAATAGAT GCGGATGAAT TTTAAACAAA TTCTTCATAA AATTCTTTAT TAAATTGCAG    4440

ACATGAATCT TGTTAATATG AGAACACCAA AAGTAAGGGT AAAAAGGGAT ACACATCAGA    4500

AAGAAACTAA TCCAATCTTC TTCTTTTTTG AACTGGTAAG TATATTGAGA TAAACAACAA    4560

AGCGCTGAGA AGGTTCTCTA TAGGCACAAA TCAGATATCC TCATGCAACA ACAAAAAGAG    4620

GGCCAATCTA TACAGAAAAA TATATTCCTG CAGTGAATTG ATAATATCGA ACATACTGTT    4680

TCCATCCTTT ACATCCTGTA AAGTTGCACC AAAAAGCCAT AAGCTAAAGA CATTTGTACA    4740

GAGATAGCTT TCCCTACAAA AACCTGGCAT TTACTTCCGT CCACAGAATT TTAACAGATA    4800

CAAGTCGGCA CTGTAACCCA CAGACTTCTT GCTGGTTTCC TAATCCCACT TTTGCCCCAA    4860

ACAGTCAGCA GGTTTGGGGA AGTAACAAAA TAGAAGCCAA ATCACTCAAA TTCATATCCA    4920

AGAGCAAATG CAGAACTGCA AAGTGTAATT GGTTGGATAC TCTCTTCGTA TAACGTCTTA    4980

GCATGGTCAC TCAAATTAAA TTCTCCTAGC AAGTTCGCCA AACGGGATAC AAAAAGATGG    5040

AATTTTTAGG ATGGAATAGC AAATGCACTT GCTGTTAATA CAAGTCCTGC ATCTCCTTCC    5100

AAATTCAGAC CTCTCCACCA TTCTCTCCTT CAAAAAGCTG CCTTCACTTC CCTTCTAGAT    5160
```

```
ACTACTTACC TTTTTTCGGA AAAGAAATCA ACCAACCAAC TATGTATCAA CTTCAATCTA    5220

TTAGAGTCAA TTCTATAATC CGATATATCC ATTTAGCTCT ATTTGGATCC ATTTCTTTCT    5280

TAGATACTAG ATTTCCAAAA AGAATGATGT TCTTTGGCAT TTATTCCACA AACTTGATCA    5340

GCTCTTGGAA GTATCACAAA CTAGAACAAA CCCATTTCAT AATTCAGCAC CATGACAAAT    5400

ATCTACACAC AAATGACACA TCTATTGTCC ATATGAAAAA TCGAAGAATG AACCAAACTT    5460

GCAACTATAA GTGAGACATA TATGAAGCAT CGAGAAAATG AAATACACTT AAGTACCTAG    5520

AAATTAAACA AAAGGTGGTC GTGGTTTTAC CATTGCAGTT TCATAAGATT CTAATTAGAA    5580

GACAGCTATA AGAATTCTGG GTGTCCATTT TGATCTATTT GGGTACATCT TCATTCCTTG    5640

ATACTAAATT CCCCAAAAAA TAATGTGGGC TCTAAATCCA CATTCCACTC AACTTAATCA    5700

GTTCTTAGAA GCATAGCAGA CAAGCACAAA CAAATTTCAT ATTTCAGCAG CAAGTCGAAT    5760

TACAAATATA GATGCACAGA TGAGACATTT ACTGTCCAAG TGAAAAAAAA TCGAAGATTG    5820

AAACAGTAAA TTAAATAAGT ATGAAGCAGT ATGAGAATGA AAATATGATG AAGCACGTAG    5880

AAATTGGACC ATTAAAGGTG ATGTAGTTGT GTATCCGTTT GCTCAATTAG GGTCCATTTC    5940

ATTATTTGTT ACTAAATTCC CAAATAGAAT GATGCGGGCG TCAAATCTAC CCAACTTAAT    6000

CAGTTCCTAG ATGTCACAAA CTAGCACAAA CTCATGTCAT TTCAGCACAA ATCAAAAATA    6060

CAAATACACA CATTTATTAT GACCAAAAAA ATTGAAGCTC GAACCCAAAA TTTGCAACTG    6120

TAAGCAATAC ATATATGAAG CAACTATGAA TTGGACCGCA AAAGGTGATA GTAATCACAA    6180

AAATTCGGCT ATATGAATCT TGGGTATCCA TTTTGATCTA TTCGGGTGCA TTTTCATTAC    6240

TTGATACTAA ATTTCCTAAA AAAAAAAATG TGGGCATCAA ATCACCCCAA CTTTCTCAGT    6300

TCTTAGAAGT ATCACAATTC AAAAACTAGC ACAAACCAAT TACATATTTC ACCACAACAC    6360

CATAGAACAA ACAGAAACAC ACACATATGA CACAGCTATT GTCCATGTAA AAACACCAAG    6420

CTTGAACCAA AACTTGAATT AGTAAACAAA ACATGTATGA AACAGTAAGA GAACGAAAAT    6480

ACAAAAAAAC ACTTAGAAAT TGAACCATAA AAGTTGTGTA TCCAGTTTGC ACTATTCAGG    6540

TCCACTTTCA TACTTTGTTA CTAAATTCCC AAAAAAGAAT GACATGAGCA TTAAATCCAC    6600

CCAAACTAGC ACAACCCCAT TTCATAGTTC AGCAAAATAA CGAAGAATAA ACAGAAATAC    6660

ACAACTAAAA ATCGAATCTT GCATCAAAAT TTGCAGTACG TTTACCTAGA AAAGGTGATA    6720

GTAATTCTGG AGTTGCAGGG TCAAAAGGGT ATCAGCAGAA CTTGATTTGA AAATGGAGAT    6780

AAGGGTTTGT ACAGGGAAGA AAACTCATAA ACCTCGTACT TGAAGACAAA ACTTTAAGGA    6840

ATTAACCATG GAGGATTTTT TTCTTTTCAA GATTCTTCTT CCTCATAATT CGACTGAAAT    6900

AATCTGAGTT TTTTAAGGCA AAATTGTCAC ATATTTATTG GAGAATGTCT ATTTTGACCC    6960

ATCATTTGCT AATTTGGATC ACTTTTCGTC CAAATAACAA AATGGATTCA AACACTATTA    7020

TCCAAAAAAA AAAATTCAA TATGGGTATG AAAAATCAAA AGAAAAAAAA ATTACAATTT    7080

AATCATTTTC AATGCAAGAA ATTATGCTGA TAATCTTGAA ATCAACAAT TTGAATTTT    7140

GATTATATAA ATTTTCGTGG TTAAAAAAGT TAAAAAGTGT TATTTATAGA TTACAACTTG    7200

ATGAAAAAGT GTTATTAATT TAGTACTCTG TAATTTTAAA ATTTTAGAAT TTGCATCCA    7260

TAAATTTTTA AGGTTTGACT TTATTTCAAA CAACAAAGTT TAATATAGTA GAGAAGAATT    7320

TTGAATGTTA TTATTATTCG AATACAATAT GTTTGTAATT TATGTAACTT TGGACTATT    7380

TATTATCCTA TAATTTATGT AATTATAGGA CTATTTATTA TCCTATAATC TTTTTATTTA    7440

TTGCAAGGAA GTATCACCAT TGAATAGTGA CGGTCTTACT TTATTTTGAT AACAAGAGAT    7500
```

```
ATACAAGAAA ATGTGGAGTG AAAAAGACGA GAAGTACTAT ATTGTGTTTC TATTGAGATT    7560

AATATAGCGA AAAATAGAGT CGAGACAAAG AAAAATACTC TAAAATCTTC GACTATATTC    7620

ACTATATAAA AGAGAGTAAT TATATGTTGA AGATAAATGT TCTTTTTTTG TGAAGCTTTG    7680

AATTCTTAAA TTAATTCGAA GTTTCTTGAA TTGTACGACG TTATTGAACT GTTATATCTT    7740

GAAGAAAAAG AACGTAGGCA GAGTGCGATC ACTCTCTTTC ACCAAATTCT GTTTACTTCA    7800

AGAATTTTGA GCACTATAAT CTAATAACAA AGCAAGCAAA GGATATATAG TTTCATCATC    7860

AAGTAAAAAG GTTGCTAATC TCATTTCTAT TGAAGTAAAA TTATTGAAGT AAAATTATGG    7920

AAAAGTAAAA AATGATGCAA GGAAGATGAA ATCTATAAAC AGAAACAAAA TGCAGGAGAA    7980

AGAGAGAGGG TTAAATACGT ACTCACACCA TTGATTTACA ACAAATCAAT AGATGCACAA    8040

CATTCAGGGC AGAGCTATAG CTTGAAAAGG TTGGTTAGAT GAACAACCTT CATTAAAAAA    8100

AAATTCCGAA TATATATACT AAATATCGAT TGTTTTTAGA TATATATTAA CTGTTGAACA    8160

ACCTTCACAT AATAAAGGTT GTTAGCCCAG CAGTTAAGGC TGTGCAAAAA TACCTCTAGC    8220

TTCAAGTTCG AGCCAAAGTG TGACAATTTC TTTAATTTTT TTATTCATTA TTCTGTTTTT    8280

TCCTAAAGTG TGAACACTCT TGGCAAAAAT TCTGACTCCG CCACTAACAA CATTATCACT    8340

TAATTATGGT TAGTTAATGC TTATATTCAC CTCATTAAAT CATTACTTAT CCATGATAAA    8400

TTGTATTAGT TTGGTATTAA ACATCCGGTA AGTGTGAATT CTTACTAGGT GAGAAGGAGG    8460

GTGACTTCTT ACCTGATAAA GTTTTTATGT ACTTTTTATG CATCAGGTCT TGAGAACTTG    8520

AAAGGAAAAT TACAATCATG GAAAAACGAC AATAGCAAGC AACTCATTGG TATGTTACTA    8580

TTTGATAGAG AGTAAAGTAT TAGATTGTAG ATATCATGTG GCCTTAAAAA TTTGATATGT    8640

GTTATTCTAG CAGGTATTAT TTTCTGCTCT TCGCTAGGAC ATTACCGATG TTCTGGATTT    8700

CCTAGAGAGA TTGAAGAATG AGAAAAATCA AAAAGTTGTT GATGTGGATC AAGTTGAAAA    8760

GCTGAAATCG GAGCTGGCGT TCATTTGTAC AGAGACACTT ATATGATTTG TTGGATTCGA    8820

ATGCTTATTC AATTGCTTTG ATAAAGGAAG AAGTTGGGCT GGTGAAACAA GACCTCGAAT    8880

GGATAAGANC TTTTTTCGTT AATATTGAGC AAGAATGGTA CAAGGATCTC TGGCCACGTG    8940

TTTTAGATGT GGCATATGAG GCAAAAGATG TCATTGATTC AATTATTATT CGACAAACAC    9000

AAATAGAACT TAACTTATAA GGTGAAGGTC AAATATAGTA GGTGACAAAC ACGATGAGAA    9060

TCTCACACTC AAACTTGTCT TCAAAATGAA GAAATCATAA TGAAGTATTT TTCTCTTTTG    9120

GATCAAGACT CTGCTTATCA AAATCTCAAC TGAAATAATC AGATTTCTCT TTTAAGACAA    9180

AATTATCACT AATGTATAGG GAAGTATCCA TTTTTGTACC CTTCACATAT AATATATTAG    9240

TCCTTAAGTT TGGTAGTATG GTCACTTTTG GTCTAAATCA TATATTATTA TAAGTGGAAA    9300

GGTTTTGAGT TTAAAGTTAG ATTACTAAAA TGCCCTTCAC TTTTTTATTA AATTAGAAAA    9360

TGTCATTTAA AAAATTTGAA AATTAAATGA ATAATGATAG CAATTTTTTT TTTATCTTTA    9420

ATTATTGATC CTTTGAGTTT CTGCAGTTAA ACTCATTCCA ATCGAACTTA ATGCTTTACA    9480

CTAAATTCAA TACTTAAGAT TGAAGATAGA TAGTCATAAT CTCCTTGATT ACAATCTAAA    9540

AATACATATT TTTCTTAGTT ATTGTTGATC AATGTTTATA TAATTTCTC CACCTTTTCA    9600

TATTCTTTAC ATTACAAAAC TCTATATAGG TATACAATAA GTTTTCTTTC TCTCATCTTT    9660

CATTCATTCT CATTCTGCTA GAGATTCTTT TTTTCCAGGT ATATCTATCC TTTTTTACAT    9720

ATGTATGTGT GGTTTAAGCC TCAATCTTAG TATAATATGA AAACGAAATC ATTTTTTTAT    9780

TAGAACTATT TATCCCAATT TTTTAAATTA ATCTTTTGGT TCATATAATT AATTTTCATC    9840

TTATGGAAAC AAAGATCAAA AGATATTCGA AAATGAGAAT AATGTTCGTC AATTTTTTCT    9900
```

```
ATTTTCATTT AAAAAATACT ATTGTATATA TTTTTTTAAA AAGAATGTAA TTCATATAAG      9960

CATAAAAGAA AAAGATTCTT ATATTTGTGA TTTCAGCAAT AACTAGAATT GCATTTATTT     10020

CTTCTTCATG TCTTTGCTAC TTTCGTCAAA GATTTTNACA TCCGTTTATT ATTTTTTTCG     10080

AGTAGAAATT CATTGTAAAC TACTTCAATA AATAAGTTGT TTGATCTGGA AAAATAATTA     10140

GCTATTCATA GACATATTCA TACCATTAGA GATTAAATCA TAGCTAAAAT TGTTAATTTC     10200

TGCATTTCTT ATTATATAAT TGAACTTTAT AAAGAAATAT TTAAAATAAA AATGAGTACA     10260

AAAATATGCT CAATTCCATT TTTCTTTAGA AATTAGATAA ATATGCCTCT TTATAGCTAA     10320

TTAATTGATT TCATTGTTAA GTGGTAATAG AAATTGAAAG CAAATAACCT TACTGTATTG     10380

ATGTCTATTA ATTTTTTTTA CAAATCATAT CTTATTATGT TAGTAACCAT ATAATCATCT     10440

TATTTCACAT GTTTCTATAT TTATAGCTTT ATATATGATG TTCATGTTAA TTAGAAATCA     10500

CCTTAGTACT CAACACTCAA TTAATAGAAT ATAACACTTG GGTGTGTCAT CCCAATTAGG     10560

GAGGATAAAT TGGCGAAGAC AATATTTTAG CTTATTCATG TTTTAAAATT AATAATGTGA     10620

TCGCTAATAA TTGATCAGGT TTAACACATG ATTTTGCATA ATTGGCATTA AAACATAGGT     10680

ATAATACATA ACTATATCAT TTAACTTAGT CTCATTTTAT ATTTATGTCC TCAAATTTTG     10740

AGTATGCACA ACTAGACAGT TAAATTAGTA TAAAGTTGAA CAAATAGACA CACCAGTCCT     10800

ACTTGTCATA ATACATGTAA GACACCATAT AGGACACAAA TTTTCATGTA GGATGTCAGT     10860

AGGACGTTTG TGTCTATTTG TCCAATTTTA TACAAGTTTA AGTGTCTACT TATGCACATT     10920

CAAAGTTGGA GGGCATTAAT GTGAAAGGAG ATCAAGTTAA AGGGCATATT CATGTAATAT     10980

GCCTAANANA TAATAGCATG AATATGTCTT TTCTCAAACG ACAATGACAT AAATGAGTCA     11040

AGCTACATAA ATAAATTTTT TCTCAAAATT CAATAACATA TATTTTTAAG AATTCATCAC     11100

CAACTTAATT ATGTACTCAA GACAAGTCAA GAAAAATCTA GAATATTTTG GAGTTATGGC     11160

GAATTGAAGG AAGATCTCTA AATGTGTATT CTAGAGAGAC TAGTCTTCTA GATAGGGTAA     11220

TTCTAGAATT AAGTAATTAA AGGAATATTC TAGGATATAG TAGAAAAATA TGTTTAGCTA     11280

GATTGTTCTA TCACCTCCTA TGAATAGAGG TGGTCCATTT GAGCTGTAGG CAAGCTAGCA     11340

AGACACGAAG TAATAAAAGT AAGAGAGCCA CCAAGAGTGA GTGCTCAAGT AAAGAGTGTT     11400

GCTGAAGCAA ACAACAAGTG TGGTAAAGAT TGTAAGACCG AATCGGGTTC TTACTTTGAT     11460

ATAATAAAAT TCAAGTTGTG AGAAATCGAT AGTGCCCCGT CGTCTGCACA CCCAAAAATA     11520

TTCAACATAT TGAGCCTTTT TTTACCTTTT ATTTTATCAA AATAGTCCAA AATTTGATCA     11580

TACATAGCAT GGAAAATAAG AAATTAATAC TCTTTCGTGA GCAGCGAGCT CTGCAGTTCA     11640

GCAAGAAAAG GGTGTTTTTT TGGCATATAA CATAAATGTA CCCTTTAACT TGACCTCATT     11700

TTACGTTTAT GTCCTCCAAC TTTAATTTGA ATATGAACAA GTAGAACTTA AACTTATATA     11760

AAATAGAACA AGTAAACGCA CGAGTCCTAC ATGCACAAT ACATGCAGGA CACCACGTAG      11820

GACAAAAAAT GATATGTAGG ATATCATGTA GGACATGTGT GTTTATTTGA TAAACTTTAT     11880

ACAAGTTTAA GTGTGTATTT GTGCACACCC AAAGTTGAAG GTCATAAATG TTATTTGAAG     11940

CCAAGTTAAA ATGACATATT TATGTATTTT ATCTTTTTTG TAATATCTAT CCATGTCTTT     12000

GACGAATAGA GTTATGCATG AAATTAATCA AAATACATGC AAATTGAAAG TGGACGGTAT     12060

CTTGTGAAAT TGATTGAAAT GTGTGCAAGT TAATCCGGTT AGCATGATTA ACAAAAATCA     12120

AAAAGGAAAA TTATGGAGCA TAATTTAAGT GACAGCAGCA TTATAACAGG TTCTTCTCTA     12180

TTGTTATAAG TAACCATTTT TGCTACTTAA AAACCAAAAG TCTTGTAGTG AGAATCGCTA     12240
```

```
ATGTTAAAAG ATGTGTTTGA TAAAAGTCTC AACTAAATTT ACTAAGTAGA AATGAGTAAA   12300

ATCCCCTTTC ACCTCATCAA CCTTAAAGGT AATTACAGGA AAAATCTATC GTCATAGACT   12360

CATTGGGTTC CGGCGGATCC TAACGTTATT ATATATGTGA CCATCTCATC TAAAAGCGAA   12420

ATCATTCATG TCTCGACTAT ATACATCTGC CCTTGACGTT GGTAACTCAA AAAAAGATGA   12480

TAGGTACAAT TCAAAAGTCA ATAAATTTTA GTATTATGAA TGAACAAACT GCCAATATAT   12540

ATATATATAT ATATATATAT ATATATATAT ATATATAACT AAAAGAATGA ATAAAAATGT   12600

TGAAAGTTGA ATTACGTTTT TACTTTTACT ATAAATTAAA TTGTTATAAA ATATTTAAAT   12660

ATTTGATTAT ATAAATTTAA TTAAATGTTA ATGACTTTTA GACTTCCTAA AATTAATTCC   12720

TAATTTAATA TCTAATCTAT TAATATTTAT CATCTATAAT TTATATGTAT ATAATAATTA   12780

TAATTTTTTT TTAAAAAAAT GTTACCTAAT TTTTTTCTCT TYYCCTCTTC TTAAAACTTT   12840

TTCCTTAACC CCTCTCATGA ATAATATAAT TGATGTGGAT AAAGTATTAT CCTTTATGAT   12900

AAATAACGAA ATTTAATAAT TTAAAGGGTG CAAATCTATA AAATGGAGAC GCACATTGAT   12960

AATGTCCTCT TGATTATTAT TAAAGAATTA CTCTAGCTTC ACAAATTTAA ATTCATTAAT   13020

GCTTAATTAC ATGATAAAAA CTTTAGTTGT TCTTTTTACA TGGTTTGCTA ACTTTAATTT   13080

TTTTTCTTCA TATTCTTCAT TTGTTTATTA TTATTTTCTA ATTACTTATT TAACTTTTAT   13140

ACTCTTAATA TTCATAACTC TCATCTTTTC ATATTCATAA CCTCCAAATA TTTAAACTAA   13200

AACTTTAAGA TATCTTTTGA TATTTGTTCA ATAATAAATT CAACTTCTTT ATCTTATGAA   13260

ACCCCTACCA AGATTATTAG GCTATTATTT TTTATTCTAT AGTAAAAACA AATGATGAAG   13320

ATTCTTGAAT TTTATAGGAT ATGAAAGAAG TCGATAAAAT CTCAGAGAGT TATGTACTAA   13380

TTTTGTACTT ATTTTTTCAT CTATATATAC ATAAATCTTA TAAGAATAAT GTCTATATTG   13440

TATTTTTTTC TTAAATATTA TGTTTCTTTT TAATTTTTTT TCACTCTGTT AGACTTCTTA   13500

ATTTAGTTTT CTATGAATGT TTTATTGCCG TAAGTCTTTG AATTTTGTAA TTGTTACATT   13560

TTATTATTCA TTACGATTTA CATATATATT TCCATGAGAT TTGGTCATTC TAACGTATCT   13620

ATAAAAATTC ACATGAAACA CACGTGTGAA GCGCATCCTC AGAAAAACTA GTGTATATAT   13680

ATATATATAT ATATATATAT ATATATATAT ATATATATAT ATATATATAT ATATATATAT   13740

ATATATATTA TTCTTATTAA AAAGAATGT  CCTTATTTCA TTTTTAATCT GGTTAAAAAA   13800

GAATAATCTC TTTCCTTTTT TGACAATATT TTAACTTTAA CTTTCCACGT AACATGTTTA   13860

AGACAACAAA ATTAAATGAC ATTTTAATCT TGTAACATAG AAAAGTAACA TATGATAATT   13920

GTCGTTGTCC CTAAACATGA TAGATGTATA ATTCAAAAGT CAATGAATTG TATTTTAGTA   13980

TTATATTATG AATGAACAAA CTGTCAAGAT GTGTATATAT ATATATATTT TATTCTTGTT   14040

AATTTGGCCT TTCAAGTAAT TAATTCATTG TTAGGCAGTT GAATTAATAA TCTCTTTTAG   14100

GAATCTTCCC ATGTGAATAA CAAGACTTAT AATAATAATA ATAAAGTCCA GATCTTGTTT   14160

CAATTGGATC ATTTGGCAAA CAATTACTCT GTTTCTGAAA CAAGGAATAG GCTTCTAAT    14220

ATTGTAGGGG ATTTTTTTTT CTTCATTAAT TTATACTTAT GATATTAATT ATTGTTTTG    14280

AGTACATATT TTAAACTCTG TTGTTTATTT TTCTGCAAAG TTTCTCCGCT TATATTGAAC   14340

ATATACACAT ATAGTACATA TATTTATTGT AAAAAAAATA ATTATTATAC TCCATTTCAA   14400

GAATTTATGT TTTGATATTA TATATTAAAT TCTATAATGT GGAAATTGTC AATGTCTACA   14460

ATGTGTTTGA TGAAATGACA ACCACTTGTT TTTATCTGCA ACAGTATAAA AATTGGCTTT   14520

GCTTCTTTTA GATTAATATA ATATTTTACA GGTCACATAT TATATTTATA TTGTGAAAGA   14580

CAAGAGATAT TGATTAAAAA AAGACTTATG GGTTTGTATT TTAATATTTC ATTCTTCTTC   14640
```

```
ATTACTAAAA GACTTGTATT GTATATTTCA ACTACTACAC TTGTTTTCTT ATCCAATAGC   14700

TTCAACATTA TTTCTCAAAC AAAGGGTTCT CTAGCTAAAC TTCAGCCTGT GTAAAGGTAA   14760

CATCTTCTTT ATTCACAGCA TAATAACAAT GAATTTGGTC GATGTTGAA GTAAGCTTGA    14820

AATTTTCTCT TTCTAAGTTT GTTTGATCCA TTTAGATTCT TTTAAATACT TTGGTATTT    14880

AAAGGACTTG TGAAGTCAAT GAATTGTATT TTAGTAATCT TGCAATTCTA GATCTAGCTA   14940

TTTGTTGTTC TCCTTTCAAC CAAACTACTT CTTCAATTTG TCTAACAAAA ATATGTCAAA   15000

AAGGTATGAA CATGCTTAAT CGGAGATCTT TATTGATTCT ACTTCAGCTA CTCTAAAAAA   15060

AAATCTTTTT TCCATTAAGC CCAAGTCGAG ATAGGAGAAA AATATTATTA GAGAGATTAT   15120

TAATTTAATG ACATTTTACT CTAGTTTTTT ATCAAAATAA GGGAATAATA TCCTGTTATT   15180

TAACTACCTT TTAAGCATTA TGGGTGGAAA GTAGAAAGAA GAAACATAAC AGAACAGACA   15240

GTAAGTTATG CTTTAATGAG TAGATCTGTA TAGGATTACA TATTTGTTTG ACTTTTCGGT   15300

GTTTCGATTA GAAAACTTAC AAGTTTTTAA TACATGTATC ATTTGTTGAT TTGTCCGTTT   15360

GGCACGTCAT CTGTGGTTAC AAGTCACATA TGAAGTATGT CCACGAGACA CACCGAATGT   15420

CAAGTATAGA TTTCTACTTG ATCATACACA ACTTTATCTG AGGTTGATGC CAAATTTAAA   15480

TGACTACCTA AAGCTGATAT TTTAAACATT AATCTTGTAC ACGAAAACAT TATTCCTATT   15540

ACTGTTTTCT TTACCTTTAC CTTATAGACT TTTTTGGCAG AAAAAAGTTA GACAGATACA   15600

TTTGATGATG TTTACCATTC TCATTCTCTC TTTATTTTAT TTTCTTTACA TTCACACGCA   15660

CAATAATTTT CTTGTAGGTT CCTTATATGC CATATGCACA TAGACGAATC TAGGATTTGA   15720

TATTTACAAG TTTCTATGTC GACGTCATAT TAATATCAAT AATAATTAGA TTGACAATCA   15780

CATATTTATA ATATTAAGTC GATAACTTTC TTCTTTGTAT AGGTTGGAAA AGTAATGGTA   15840

AACGAGCAGG ACTCCTTTTT CTTTTTTTTG TAAATAATTA ACAGTTGTGA GATTTTATGT   15900

TTGTGACTTC ATGTCATAAA CATTTTGATG TGTGATTAAG ATTGACATTT CCAATTGTGC   15960

GAGTCTAAAA TTACTATATG TGAAAATAGT GATATTATTG ATTATTCGTA TTTTTTCATC   16020

TTCTTTCTCC TGTTAAAGTT TTATCTACTT TTTATTCATC AGGTCTTGAG AAAAAGTAGA   16080

ATCATGGAAA AACGAAAAGA TATTGAAGAA GCAAACAACT CATTGGTATG TTATTTTATA   16140

GAGTAAACTG TAAAGTATTG AATTATAGAT ATGTGGCTTT AAAATGTATT ATTTTGGCAG   16200

GTGTTATTTT CTGCTCTTAG CAAGGACATT GCCAATGTTC TAATTTTCCT AGAGAATGAG   16260

GAAAATCAAA AAGCTCTTGA CAAAGATCAA GTTGAAAAGC TAAAATTGAA AATGGCATTT   16320

ATTTGTACAT ATGTTCAGCT TTCTTATTCC GATTTTGAGC AGTTTGAAGA TATAATGACT   16380

AGAAATAGAC AAGAGGTTGA GAATCTGCTT CAATCACTTT TGGATGATGA TGTCCTTACT   16440

AGCCTCACCA GTAATATGGA TGACTGTATC AGCTTGTATC ATCGTTCTTA TAAATCAGAT   16500

GCCATCATGA TGGATGAGCA ATTGGACTTC CTCCTCTTGA ATCTGTATCA TCTATCCAAG   16560

CATCACGCTG AAAAGATATT TCCTGGAGTG ACTCAATATG AAGTTCTTCA GAATGTATGT   16620

GGCAACATAA GAGATTTCCA TGGGTTGATA CTGAATGGTT GCATTAAGCA TGAGATGGTT   16680

GAGAATGTCT TACCTCTGTT TCAACTCATG GCTGAAAGAG TAGGACACTT CCTTTGGGAG   16740

GATCAGACTG ATGAAGACTC TCGGCTCTCC GAGCTAGATG AGGATGAACA CAATGATAGA   16800

GACTCTCGAC TCTTCCAGCT AACACATCTA CTCTTGAAGA TTGTTCCAAC TGAACTGGAG   16860

GTTATGCACA TATGTTATAC AAATTTGAAA GCTTCAACTT CAGCAGAAGT TGGACGCTTC   16920

ATTAAGAAGC TCCTGGAAAC CTCACCGGAT ATTCTCAGAG AATATATCAT TCAACTACAA   16980
```

```
GAGCATATGT TAACTGTTAT TCCCCCTAGC ACTTTAGGGG CTCGAAACAT TCATGTCATG    17040

ATGGAATTCC TATTACTTAT TCTTTCTGAT ATGCCCAAGG ACTTTATTCA TCATGACAAA    17100

CTTTTTGATC TCTTGGCTCA TGTTGGAACA CTTACCAGGG AGGTATCGAC TCTTGTACGT    17160

GACTTGGAAG AGAAATTAAG GAATAAAGAG GGTAATAACC AAACAAATTG TGCAACCCTA    17220

GACTTGCTGG AAAATATTGA ACTCCTCAAG AAAGATCTCA AACATGTTTA TCTGAAAGCC    17280

CCAAATTCAT CTCAATGTTG CTTCCCCATG AGTGATGGAC CACTCTTCAT GCATCTTCTA    17340

CACATGCACT TAAATGATTT GCTAGATTCT AATGCTTATT CAATTTCTTT GATAAAGGAA    17400

GAAATCGAGT TGGTGAGTCA AGAACTGGAA TTCATAAGAT CATTCTTTGG GGATGCTGCT    17460

GAGCAAGGAT TGTATAAAGA TATCTGGGCA CGTGTTCTAG ATGTGGCTTA TGAGGCAAAA    17520

GATGTCATAG ATTCAATTAT TGTTCGAGAT AATGGTCTCT TACATCTTAT TTTCTCACTT    17580

CCCATTACCA TAAAGAAGAT CAAACTTATC AAAGAAGAGA TCTCTGCTTT AGATGAGAAC    17640

ATTCCCAAGG ACAGAGGTCT AATCGTTGTG AACTCTCCCA AGAAACCAGT TGAGAGAAAG    17700

TCATTGACAA CTGATAAAAT AATTGTAGGT TTTGAGGAGG AGACAAACTT GATACTTAGA    17760

AAGCTCACCA GTGGACCCGC AGATTTAGAT GTCATTTCGA TCACCGGTAT GCCGGGTTCA    17820

GGTAAAACTA CTTTGGCATA CAAAGTATAC AATGATAAGT CAGTTTCTAG ACATTTTGAC    17880

CTTCGTGCAT GGTGCACGGT CGATCAAGGA TATGACGACA AGAAGTTGTT GGATACAATT    17940

TTCAGTCAAG TTAGTGGCTC AGATTCAAAT TTGAGTGAGA ATATTGATGT TGCTGATAAA    18000

TTGCGGAAAC AACTGTTTGG AAAGAGGTAT CTTATTGTCT TAGATGATGT GTGGGATACT    18060

ACTACATTGG ATGAGTTGAC AAGACCTTTT CCTGAAGCTA AGAAAGGAAG TAGGATTATT    18120

TTGACAACTC GAGAAAAGGA AGTGGCTTTG CATGGAAAGC TGAACACTGA TCCTCTTGAC    18180

CTTCGATTGC TAAGACCAGA TGAAAGTTGG AACTTTTAG AGAAAAGGAC ATTTGGTAAT    18240

GAGAGTTGCC CTGATGAACT ATTAGATGTC GGTAAAGAAA TAGCCGAAAA TTGTAAAGGG    18300

CTTCCTTTGG TGGCTGATCT GATTGCTGGA GTCATTGCTG GGAGGGAAAA GAAAAGGAGT    18360

GTGTGGCTTG AAGTTCAAAG TAGTTTGAGT TCTTTTATTT TGAACAGTGA AGTGGAAGTG    18420

ATGAAAGTTA TAGAATTAAG TTATGACCAT TTACCACATC ACCTCAAGCC ATGCTTGCTT    18480

CACTTTGCAA GTTGGCCGAA GGACACTCCT TTGACAATCT ATTTGTTGAC TGTTTATTTG    18540

GGTGCTGAAG GATTTGTGGA AAAGACGGAG ATGAAGGGTA TAGAAGAAGT GGTGAAGATT    18600

TATATGGATG ATTTAATTTC CAGTAGCTTG GTAATTTGTT TCAATGAGAT AGGTGATATA    18660

CTGAATTTCC AAAATTCATGA TCTTGTGCAT GACTTTTGTT TGATAAAAGC AAGAAAGGAA    18720

AATTTGTTTG ATCGGATAAG ATCAAGTGCT CCATCAGATT TGTTGCCTCG TCAAATTACC    18780

ATTGATTATG ATGAGGAGGA GGAGCACTTT GGGCTTAATT TTGTCATGTT CGATTCAAAT    18840

AAGAAAAGGC ATTCTGGTAA ACACCTCTAT TCTTTGAGGA TAAATGGAGA CCAGCTGGAT    18900

GACAGTGTTT CTGATGCATT TCACCTAAGA CACTTGAGGC TTATTAGAGT GTTGGACCTG    18960

GAACCCTCTT TAATCATGGT GAATGATTCT TTGCTGAATG AAATATGCAT GTTGAATCAT    19020

TTGAGGTACT TAAGAATTCG GACACAAGTT AAATATCTGC CTTTCTCTTT CTCAAACCTC    19080

TGGAATCTAG AAAGTCTGTT TGTGTCTAAC AAAGGATCAA TCTTGGTACT ATTACCGAGA    19140

ATTTTGGATC TTGTAAAGTT GCGAGTGCTG TCCGTGGGTG CTTGTTCTTT CTTTGATATG    19200

GATGCAGATG AATCAATATT GATAGCAAAG GACACAAAGT TAGAGAACTT GAGAATATTA    19260

GGGGAACTGT TGATTTCCTA TTCGAAAGAT ACAATGAATA TTTTCAAAAG GTTTCCCAAT    19320

CTTCAGGTGC TTCAGTTTGA ACTCAAGGAG TCATGGGATT ATTCAACAGA GCAACATTGG    19380
```

```
TTCCCGAAAT TGGATTGCCT AACTGAACTA GAAACACTCT GTGTAGGTTT TAAAAGTTCA    19440

AACACAAACC ACTGTGGGTC CTCTGTTGCG ACAAATCGGC CGTGGGATTT TCACTTCCCT    19500

TCAAATTTGA AAGAACTGTT GTTGTATGAC TTTCCTCTGA CATCCGATTC ACTATCAACA    19560

ATAGCGAGAC TGCCCAACCT TGAAAATTTG TCCCTTTATG ATACAATCAT CCAGGGAGAA    19620

GAATGGAACA TGGGGAGGA AGACACTTTT GAGAATCTCA AATTTTTGAA CTTGCGTCTA     19680

CTGACTCTTT CCAAGTGGGA GGTTGGAGAG GAATCCTTCC CCAATCTTGA GAAATTAAAA    19740

CTGCAGGAAT GTGGTAAGCT TGAGGAGATT CCACCTAGTT TTGGAGATAT TTATTCATTG    19800

AAATTTATCA AAATTGTAAA GAGTCCTCAA CTTGAAGATT CTGCTCTCAA GATTAAGAAA    19860

TACGCTGAAG ATATGAGAGG AGGGAACGAG CTTCAGATCC TTGGCCAGAA GAATATCCCC    19920

TTATTTAAGT AGCATTTTGG TTGAACTTTG CTTGGTGATA TTGTATATGA TTAAAATATC    19980

CTGTGATGAG ATTCCTCTTA GTTTCTTTTA ACAAAAAATA TAATTTTTAT AAGTACACAT    20040

ATCGTTTGTT AATTTGTCCA TTTGTGATTG CAAGTCACAC ATGAGGTATG TTCGTATTAT    20100

GGGTTTCAAC TTGATCAGAC GTAATTTTAA GATAAGTGCT TATATGATGT TGCATGCCAG    20160

ATGGAAGTGA CTATGTGAAG TTTATATTTT AAACATTAAT CTTGTATACC AAACTACTAT    20220

TCCTATGCTA TGTTGTTTGC CATTGTCGTT CTCTCTTTAT TTTTTTTCTT TCCATTCACA    20280

CACACATTAA TTTTCTAGTA GACCGCATAT TACTACATCT GTATTGTCCG TATACAAGAC    20340

GAATCCAGGA TTTGATGTTT ACAAGTATTT GTGAAGAATC CAGGATTTGA TGTTTACAAG    20400

ACAATTAGAT TCATATATGT ATAGGATTTT GACAGAAACT GAGGGATTCA CATGACAATT    20460

ACTCTGTGGA TTTGCCTTTG GCTGTCCAAA CCTCCTTTGT GTCTAACTTC GTCTGAAGTC    20520

CCATTTATAT GCTCAAAGCT CAGTCAAGGT ACTGATTCAA AAGCTAGGCT GTGAAGTAAA    20580

CTTTAAAATG ATATTGCTGC AAAGTCGCTC AACAAAGGGT CATAACCATC ACTACAACTA    20640

CACAAGCTCA AGCAAGTAAA CGCGGGTGAA AGATTAACAT AGATCGCTAT CCCCTGCAAA    20700

AGCTAAGGAA AGCATCTCTA ACTTCTTAGC ATGTACTCAA ACACACGATC TGTAAGGATG    20760

CCAGAAAGAG AAAGTTACGT TGCCGCAATT CCTTACAGTG TTGCACAATG TCCCCAAAAC    20820

CAACATCACA CTACAAAAAA AGGCTCAAAT TCTGGGGGTT ATAATTAGAC GGTCAATAAC    20880

CCCTGCAATT TAGTGTTGTG GAGGTTGAAT AAACTCCTCC AATTAGGAGT GTCACAATTA    20940

AGTCGCGTGG GATTCTTGGC ACATCCCGGT AAGGTTAACT AGCGGGGGTT TTGAACCCCA    21000

ACCGCATTTC AAACTAGGAG TCGAAACCCC AACGATTTGT GAACTCGGGG GAGTCAAAAA    21060

CCCCCGCAAT AAATGATTTT TACATTAAAA TTAATAGGAG CTTGGACCCC TGTGATTTAT    21120

GAAATATAAC TTTTTGTAGC ATTTGCCAGA AATATTCAAT TTTAGATACT AATAATAAAT    21180

TAATTAACTA ACATGTGCAT CATTATTCAA AGGACATATT AGTATTAAGA AATAATACAA    21240

TATTCAACAC AAAAGTACCC AAACTCAAGA TAGGATCAGT TTATGGAACT TCAACTAGTT    21300

TCACTATAAT TATTGTCACT AACATCAGCT GGCTGCAAAG GAGAATACAT AATAAGTGAC    21360

TTTATCCAAA CTCAAAATCA TGGCTGAATG TAGTAAAACA CCAAAGATTA TAATAATTTC    21420

CATTAATTAT CATATACTAC ACAACAACAA ACTAAAAACA ATATAGAAAA GGATTAAACC    21480

ATTTACACAA GCAATGATTC TATACCATTT CAAAACGACA ACATACTGTA CTACTAAACA    21540

AGACACCATC AAACTGATTT GGACAAATAT TAACAATAGT TAAAACATGA ACAAAGAATC    21600

TCAGGTTTCT TGTCAGTAGA AAAGAGACAG ACTAGGAACT GGAGTGCTAT TTTTCTTATA    21660

AGAGACAATT AATGTTTACT TCTTTATATT TTGACTATAA GTTGATTGGT TATAATGTTT    21720
```

```
                                      -continued

ACGAGGTTGT ATATAATCCG ATGTTCAATG ATATGACTTT CCTATTGACT GAAATGCTTG    21780

AACGCAAACA GTATATCTAG ATTAAGAATG AGGACGAATT ACCTCTAGAG GCATGGGTAA    21840

TGGAAGCATA ACTCCTTGAT AATGGTTGTT AGCCCACTGC AAGTCACAAA ACAAAACATC    21900

CGTAATATTA ACATACTAAG GTTGTAAGCA CTAAACGACA ACAACTATGC CTCAATCCCA    21960

ACTAAGTTGG AATCGACTAT ATGAATACTC ACAATTTCGA TTTATAGACA AAGATACTAG    22020

TAGAAATGAC GTCTTTCCTT TCTATGTTAA CACTTGGACA GAGAATGTTA AAGACTTACA    22080

ACAACAGAAA AGAGTTAAAA TCATTTAATT GAGCAAGGAT TTCAAAACGA CAACACAATA    22140

TACTCAATTT TTCGACGGAA ACAACTGGTT GGACAACAGT GCTATTTGTA ACTCCAATGA    22200

ACAACACTGC AACGTACATG TATCTCATTG CACTAAATAA ATCCCGTTGA GAGTAACATA    22260

TCAATAGTTA CGAACAATAT GATCACGACA AAGGATTGTA AGTACCACAG GACAAGTCAT    22320

GCTTGCATGA AAAACGGATA TGTAAAGAAC CAAAATCCTG CTGCTGAAAT AAGCAGTTAT    22380

GATTATCCAA AAATCATGAA TACACATGCA CTTGAGTTTG TTCCAAGAAA AACACAACCA    22440

ACTACTGTCG CAAGTGAAGA TTCAAAAGTG ACTATTGATG TTAATTCTTC CACAAGGTTG    22500

AATAATTTTG TCACTATAGG ATTTAAGACG AAGAAGAAAC AGGCGACAAT TTTGTAAGCA    22560

TAGACCTTCT TATGCAACTA TGAGCTGGTA TGCTATTCAT TTTCTTTACT CGTAAAAATC    22620

GTTGATACTA AAGAATGCCA ATCCAAGTCC TGCTGAATAG GCGCCAGGTG ACTGGTTGCT    22680

GTTAATAATT TTGGGAAACC TACAAGGTCT TAGAAATAAA GTGCACCCAC AAATAAACAA    22740

GCATATGAAA TATACTACAC TGCACCCACA AATAAACAAG CCGAACAAAT TTGAGGAGCA    22800

GTAGGGGCAC ACCTTCAACT AGAAAATAAT AAGCTTCTTC CAATATTGCT CACAAAGATT    22860

GTACAAATCT TTGGGAATCA AATACGTATA TGAAGCACGG AGTAGAAGGT AAAAGATACG    22920

CAACATCTAA ACTTCTAAAC ATTCCCTCTA GCCTCTGAAG ACTACATTAT CTTTACTAGC    22980

TTAAAGAAGG CTTTATCAAG GGGGGAAAAC AATCTTTTGC TGCCCGACGA GGGACAAAGA    23040

AATCAACACG AGTGACTAAA GCAGTGAGTC TGGCAGAACA TGTTAATCCT ATCAAATATC    23100

AATGCTAAAA AAGAGTAAAA TTACCTTGAC AATACTTGTA TTAGTCAAAT TTTACCTAAA    23160

CAAACAAAGT TTAAGCAGCT AGCCGCACAT CTGCCTATAA AACTCATACG AAAATCAACT    23220

GGCGACTACA CAAAAAGAA ATTTTCTACA CAAAGTGAAG AAATCTACAC GAGCAAAAAT    23280

TTTAACATAC ATGTACCAAA TTTTCTATAA ACTGACCTTG AGTTAGTACA CAATATCATT    23340

TTCATTCTTT AGCAGCGAAA TCAACTGTCA ATATACCGAT GTCAACGCAG ATCGCGCAGT    23400

TGATGATGTC AAATGATTGA TTTCTTGATG AAGAATGTGC CAAACCTTGT GAACTAGATG    23460

ATGAGTAAAT GAGTTGCGTA AGTTATCGTA ATGCTTCAGC TTCGACATAT CTGCTAACAA    23520

TAAAAGTAGA TGAAATTATG ATCTTTGGTC AAGAGAATTT GGATCAAGAT ATGAAATGAG    23580

TCATATTTCT ATTTTTCTAA TGATTGCAGG TGAATTTATT CACCATTAAC AAGGTATTAC    23640

CTCTTTGAGT ATCAATGTAC TAAGTTAGTA GCTTCACAGG TAGTCCAACT AGTAAGAAAA    23700

AATAAAAAAT CTCCCAGTAG TAAAAACAAC ATTCATTGTA TAAATTAATG TTGACTATTA    23760

CTCCATTGAT TGTTGCAAAT ATACATTTAT TTTACCTGTT GTAGAAAATT GCTACATTAC    23820

TGATATTGTA AAAGATACAA ATATAATAGC ACACCATGTA CTTGACTCGA CATGCCCATC    23880

TGGAATGGAA AGTTGAATAA GCTTGCTGAA CATAGCGAGA CTGAGAGAGA ATATGAATCT    23940

TTGTACCTAT CGGACAACTA ATCATACACC TTATACACAT TGGTATTGCT TTTGCATTAT    24000

GATTGGTCAT AATATTATGT TATAAGAGAG TTAGTTATGT TGCTCCAACA TGGATGAACA    24060

TATGTGTGGC CTGGGAAGAG TACATCGGAC TTACCAAAGC TCGACAAAAT ATCCTCACAA    24120
```

```
CGATTTTGGT ACTCAGTCAC GTAGGTTACC TGTTCGAGAT TGGCGCTTCA CTCTGCTGCA    24180

GACTCATATC ATTTCTGTTT CAATCGAATT TTCATCTTAT CAGCAAAATG CAACCAATCA    24240

CTTAATTGAT TATTCCTAAA TAACCACGGG TACCATTGTA ATGCTTCACC ATCAAGGTAG    24300

AGCGACACCA CATTAAGCTT TTGATCTTCC TCAAATGTTA TAAAAATCGA AATAATGTAT    24360

AGCTTGAACT ATCCAAGCCT CCTGATTCTC TCCTCGGAAC TGTCATAGTT TGGCAACCAT    24420

AATTGTGTTT CTAGGTTCAA AAGATGTCCG AGCCTTTTCC CCCCGGTTCG AACTCATCAA    24480

CGAAATTTTC AGTTAAGAAT TGATTTTATT CATCAATTTG ATTTTTTATA AAAGCATAAA    24540

TTCAATTAAA ATTAGATGTT CATTCTAGCA CTTGCCAAAC ATTCTCTGTT TGAAATGTAT    24600

GCAACTATGC TTGTGCAATC CTAGTATTAT TCTGAAGAAA ATATCATCAC CAACACTAAG    24660

AATATCCACT GAGAGTAAAT GTCTATTTAT CTCTATTTAG TACTATTATA GTTGATTTTA    24720

AGCATAAGCA TCGATGAAC TTGAGGCCTC AACTATTCCT TAGGGGCCTA ACCACTGAAA    24780

AATTATAGTG ATCTAAACAA ATGAAAGAGT ACCTCAACTT TTTTTAATCC CTGAAGATCT    24840

AGAAGCTCTC CTGTTAATTT CAGTTCTAAA TAAGAATATA ATGTATTAAT ACAAGTATAC    24900

AGAGGTAAGT GAACATTGAG GGCACATTTA ACAGCTAAAA AAGAATTAAT TAACAAACAA    24960

AGGGAAAACT ATATAGACCT TACTCCAGCA TAAACAAAAG GATATATGGA GACGATAACT    25020

CCAAATTTTA GAAGAAACA AGGCACTTGT TAGCGACACC ATTTCAGAAA AAGTGGCCCC     25080

AAAAGATCTG TAGACACAGA ATGTCTCGAA GAATCTGTAG AATCACCCTA AGCTCTTGAA    25140

GTTCCTTACT AGTGTTGGCA ATCTCCTCCA TTCCAAGTGC CTTAAAGCGG AAGCTGGATA    25200

ACCAATTATG CAAAAGAGCC ACTGGACAAG AAGAGCTCAA AAGCTAATGA AGCGTCTAAC    25260

TAGGAAAGAT AAACATGAAT TGTCAAAATG TAGGATTTGT GCAACATTAA GTTATTCTTC    25320

ATATGGCAGA CCAGTAAATT ATTCAAAGAG TTCACTCGAC ATGAATTGTT TAACTATGTT    25380

ATCTCAGTAA ACACTGAAGT TCATTACACT GTTTATTTAT CCCTGGCATT TATCAGAATC    25440

AGCAACACAA TTTTTAAATT AGGATTATTG TTCTTTCTCT TGGAAACTTC TGGTTTTACA    25500

ACTAACAATC AATTTATCTA TTTTATCACA AACACAGTTC ATGTATCCCT TCTCAGAAAA    25560

AAAATACACA GTTAATGTAT CGAGCCATGA TTATTGAAAA CACGCACCAG CAACAGGTAT    25620

CAGATAAGTT CGCTGAAATT TGAACTTGAG TTCTCTCAAT CACTTCATTG ACTTCAAACT    25680

GAGAGTATTG AAAGTTTGAT TAACTTTCTT ATCTCTTTCC TTTATGGCAG ATAAGCAAAG    25740

TTAAAGGTCA CAGTTATCCA CTGAAGTCAA GCTAAATGTC ATTTTAATGT ACTATGCCTA    25800

GAAAGAATTA ATATAACTTG GAAAAATGTT GAATTTCTTT TGTAAGTGTA CAAAGTTAAA    25860

ATTATGAAAA CAAGTATTTG GAGTTTCTAA AATTTTGGAA TATTCTGGCA AAATTTGAGC    25920

GGAGAAATTG GCAGGTTCTT ACATCTTTTT ACTGTTCTAA AAAGATGTCT ACAATTCGTT    25980

TGATCAAAGC CCCGACGGAA CTATTAAGTA GACGAGGTTA GTAAAATAAC AAGCAACCAA    26040

AGCAGTTTAG AGAGATCACT TTTTTCCCAC GGGATTTTTC TAGTAAGATT TTAACCAGGC    26100

ATATTATCTT CTAAATATGT AGCGAGTTAG TATCATTATA CTTTGTCTAC AAATTAAATT    26160

TCGATTACTC TGGGTAAACA AGCCATATAG TATGCTATTA ATTATTTTAG TTGAGAATGA    26220

ATGCCTGTAC AGTCCCAATG TCAGTTGACT GACTGACTTG TTCAAACCTA TTAATTATGC    26280

CATTTTCTTG GTATTTTCTC CTCCACGCAA ACAAAGAACA TACATATAAG ATTTTTCATC    26340

AACTGAAAAG GTTCCATCGT CTCTAATTAC AACTCTGTGT TTAAACTTGT TATCTACATC    26400

AGATCCGGAG AATTACTGTC ATGGAAAGAA GCAACCTACA GGTATCTTAT ATTTACTTGG    26460
```

```
ATCATTATAA GATGAGACTG ATGAAGACTC TCGACTCGCC CAGCTAGATG AGAATGATCA   26520

GAATGTTAAA GACTCTCGAC TCTCCAAGTT AGAGCATTTA CTCTTGAAGA TCGTTCCAAC   26580

TGAACTGGAG GTTATGAACA TATGTTATAC AAATTTGAAA GCTTCAACTT CAGAAGAAGA   26640

TGGACACTTC ATTAAGCAGC TCCTGGAATA TTCTTCGGGA ATATCTTATT CATCTACAAG   26700

AGCATATGAT AACTGTTATT ACCCCTAGCA CTTCAGGAGC ATATGTTCT  TTTTGTTATT   26760

GCGTTGTTGC CTAGGAGAAA TATCTGCATC CCTATATTTT CCAACTGGTA GCATTAACAA   26820

TATCAACTTT TTTGAAGGTG AAACCATCCA ATTTTTTTA  TAGACTCTCA ATTTAATTGC   26880

TAGTATCTTC TAACCTTGGC TTCTTTACTG CAGGAGGTAT AGGATTGATG AGCTTAACAA   26940

AGAAACATTT GTTCAAAAAT ACACGGTGAC GTCTTGGTAG ACAAACACAA ATAGAAAACT   27000

TATGAGGTGA AGTTCAAGCA TAGTAGGTGA CAAACAAGAT GACAATTTCA AACTCAAAAC   27060

TTGTGTTGAA AATGAAGAAA ATAAAATGGA GGATTTTTAT GTTTGATCAA GACTTGGTTA   27120

TCCAAATCTC AACTAAAATA ATCTGAGTTT TTTTTGTTTT TTTTAGCCAA AATTATCACT   27180

TATGTATAAC TTTTTTGAAA TCATATCTTA TGTTAGTAAC TATATAACCA TCTTATTTCA   27240

CATGTTTATA TATTTACGGT GTTATATATG ATGTTCATGT TACTCAGAAA TCACCTTAGT   27300

ATATGTTCTA CTTCGATGTT ACAATTTCTT TAGCATGATC AAAATTTTTA TTGTCGATAT   27360

GAATATGCTT CTAGTTCGAG GTGTAATTGT TGTCATAGGT GGTTTGACCA TTGGGTGAAA   27420

TCGCGGCTTG TGACTCCTTG ATTTTTCTAG AAACTTGAAG AATTGGAGCT CTTGATCAGA   27480

ATTGATCATT AAGGCATCAA AGGCGTTAGA GCACACAACC TTCCTTGATA CTTTATCTTC   27540

ACAATTTATT GTTTGCTCCT TGCCTGTTGG GTTAGTGCAA TCTAATTGTT ACCTGGAGAA   27600

AATAATTTGC TTGGTACTTC AGTCCAGCCT TCCTTATCGT TGTCATTCAA AGTGAAGTCA   27660

TGATCACATG TACCACCAGA TTCGAAAATT TAATCCAAAT TCTCTTCACA CAGTCGCACC   27720

AGGTTTGTCT CTCATACAAC TAAAGGCCGG GAAGAGATGT GCGCAGACAT GGCTGCTGCT   27780

AGGGATTAGG GCGTCCTCTG CTCTCGTAGC AGCCTCTGAA TGTGCTCCTT CTCTCTTAAT   27840

TTTTTAACCG ATTTTAAGAA AATAAATTAA TAGTTAAGGT TTATTTTTGT AATCAAATTT   27900

TTGACTTAGA TTCTTCTCAG TTAAGGTAAT ATATGACATG ATATATGATA GAAATGTGGC   27960

TTTGGTCTTT TGGCAGGTGT CATTTTTTGC TCTTCGCAAG GATGTTGTCC ATGTTGTGGA   28020

TATCATAGAG AAGTTAAAGA ATGAAGAAAA TCAAATAGCT CTTGACGTGG ATCTAATTAG   28080

AGATCTGAAA CTTGTGCTTG CATTAATTTG TGCAAACGTC CTGCTTTCTT ATTCCGATTT   28140

GGAGAAGTTT GAAGATGTAA TGACTTTACT AAGAGAAATG GTTACAGATA TGTGTCAGTT   28200

AATTTTGGTT GATGTTGACA ATAAATTCAA CATGCTTCAA GTCCTTGGTA GCCTCATGGA   28260

TAATATGGAT GATTGTATCA GCTCATGTCC TCATTCTACA TCCATGACTG AGGAGGAGTT   28320

GGACTTCCTC CTCCTGAATC TCTATCATAT ATCTAAGTTT CTTGTTGAGA AGGATTTTCC   28380

ATTAGTGACT GAGTATGAGA TTCTTCAGAA TGTGTGTGGC AACGTAAGAG ATTTCCATGG   28440

GTTGATAGTG AATGGTTGCA TTGAGCACGA GAGTGTTGAA TATGTCTTAC CTCAGTTTCA   28500

ACTCATGGCT GAGAGAGTAG GACACTTCAT TTGGGAGTGT CATACACAAT CTGCACTCTC   28560

TGATTAGACA GATAAACACG ATCACCTCAT CATGTTAGAA CATCTACTCT TGAAGATTGT   28620

TCCAATTGAA TTGGACGTTA TGCACATATG TTATACAAAT TTGAAATCTT CAACTTCAGC   28680

ACAAGTTGGA CGCTTCATTA AACAACTTCT GGAAACCTTT CCAGACATTC TCAGAGAATA   28740

TCTGATTCAT CTACAAGAGC ACATGGTAAC TGTAATCAAC CCAAGCATTT CAGGAATTCG   28800

AAACACTCAT GTCACGATGG AGTTCCTGTT GATTATTCTT ACTGACATGC CTACTCACTT   28860
```

```
GATTCATCAT GCAACATTTT TTGATCTCTT GGCACGTGTT GGAGCACTTA CCAGGGAGGT    28920

ATCAAATCTT ATTTGGGACT TAGAAGAGAA ATCAATGAAG AAAGAGAGTA CCAATGAAAC    28980

AAATCGTACA ACACTAGACT TGCTAAAAGA TATTGACCTC CTCAAGGATG ATCTTAAACA    29040

TGTTTATCTC AAAGTCCCGG ATTCATCTCA ATGTTGCTTC CCCATGAGTG ATGGACCTCT    29100

CTTCATGCAT CTGCTACAGA GACACTTGAA TGATTTGCTG AATTCCAATG CTTATTCAAT    29160

TGCTTTGATA AAGGAACAAA TTGGGTTGGT GAAACAAGAA CTAGAATCAA TAAGATCTTT    29220

TTTCCTGAAT ATTGAGCAAG GATTGTATAA AGATCTCTGG GAACGTGTTT TAAATGTGGC    29280

ATATGAGGCA AAAGATGTCA TTGATTCAAT TATTGTTCGA GATAATGGTC TCTTACATCT    29340

TATTTTCTCA CCTCCCAGTA TCATAAAGAA GATCAAGCTT ATGAAAGAAG AGGTCCCCGA    29400

TTTACATGAG AAGATTCACA AGAATAGAGG TCTAATTGTT GTGAACACTC GCAAGAATCC    29460

AGTTGAGAGC AAGTCATTAA CAACTGGTAA AATAATTGTA GGTTTTGAGA AGGAAACAAA    29520

CTGGATACTT AGAAAGCTCA CCAGAGGACC GACAGGTCTA GATGTTATTT CGATCACTGG    29580

TATGACGGGT TCAGGTAAAA CTACTTTGGC GTTCAAGGTA TACGATGATA AATCAGTTTC    29640

TAGCCATTTC GACCTTCGTG CATGGTGCAC AGTTGACCAA GAATATGACG AGAAGAAGTT    29700

GTAGGACAAA ATTTTCAATC AAGTTAGTGA CTCAGATTCA AAATTGACTA AGAATATTGA    29760

TGTTTCTGAT AAGCTGCGGA ACAGCTGTT TGGAAAGAGG TATCTTATTG TCTTAGATGA    29820

TGTGTGGGAT ACTAATACAT GGATGAGTT AACAAGACCT TTTCCTAATG GTACGAAAGG    29880

AAGTAGAATT ATTTTGACAA CTTGAAGAAA AGAAGTGGCT TTGCATGGAA AGCTCTACAC    29940

TGCTCCGCTT AACCTTCGAT TGCTAAAACC AGAAGAAAGT TGGGAGTTAT TAGAGAAAAG    30000

GGCATTTGGA AACAAGTGTT GCCCTGATGA ACTATTGAAA GTTGGTAAAA AAATAGCCGA    30060

AAATTGTAAA GGGCTTCCTT TGGTGGTGGA TCTGATTGCT GGAGTCATTT CTGGGAGGGA    30120

AAAGAAAAAG AGTGTGTGGA TTGAAGTTTT AAATAATTTG CAATTCTTTA TTTTGAAGAA    30180

TGAAGTGGCT GTGATGAAAG TTATAGAAAT AAGTTATGAG CACTTACCTG ATCACCTGAA    30240

GCCATGCTTG CTGTACTAGA AACTCTGGAA TCTGCCTTTG TCTTTCTCAA ACCTTTGGAA    30300

TCTAGAAACT CTGTTGTTGG ATAACGAAGG ATCAACCTTG GTACTATTGC CGAGAATTTG    30360

GGATCTTGTA AAGTTGCAAG TGCTGGCCAT GAGTAATTGT TCTTTCTTTG ATATGGATGC    30420

AGATAAATCA ATACTGATAG CAGAGGACAC AAAGTTAGAG AACTTGAGAC ATTTACACAA    30480

ACTCGTGCTT TCCTATTCGA AAGATATTTT CAAAAGGCTT CTTAATCTTC AAGTGCTTGG    30540

AGTTGATCTC AAGGAATCAT GGGATTATTC CACAGAGCAA CATTGGTTCC CGAAATTGGA    30600

TTGCCTAACT GAACTAGAAC ACCTCACTGT AAGTTTTGAA AGTTCAAACA CAAATGACAG    30660

TGGGTCCATA AATCGGCCAT GGGATTTTCA CTTCCCTTCG AGTTTGAAAA AATTGTGGTT    30720

GTATGACTTT CCTCTGACAT CCGATTCACT ATCAACAATA GCGATACTGA CCAACCTTGA    30780

AGAGTTGGCA TTTTTTGATA CAATCATTCA AGGGGAGAA TGGAACATGG GAGAGGAAGA    30840

CACCATTGAG AATCTCAAAT TATTGAATTT GTATCAAGTG GCTGTTTCCA AGTGGGAGGT    30900

TGGAGAGGAA TCCTTTAAAA TTGGATGAAT GTTGTGATCT TGAGGATATT CCGCCTAGTT    30960

TTGGGGATAT TATTTCACTC AAACTTGTAG AGAGCCCTCA ACTTGAAGAT TCCGCTAAGA    31020

AGATTAAGAT TTATGCTGAA GATATGAGGG GAGGAGACGA GCTTCAAGTC ATTGGCCGGA    31080

AGAATATCCC GTTATTTAAG TGAAGAGCAT TATTTTGCAA GAACCGGATG TATCCTTGAC    31140

AGAGAGAGGC CTTGTTGCTC CACTTGGTTC TATACTTGTG CTGCCAAATG ACAAATACCG    31200
```

-continued

```
CCTTGGTTGC TATTGCAAAG AACCGTCCTA ACTTGATCCG ATTTTGTTTG TGTTTACTCA     31260

AGCCTCAAAC TTCTGATTAA AAGCTCAATG GTTACTTTTT ATTTAATTTG TTGAAACTCT     31320

TTAATTTGAA GACTAATTAC ATTATGCAAA AGGTTATTAA AAACATGTTC TGTAGACTAT     31380

ATGACAGCAC CAATAGGTTC TTACACCTTT TTACTCTTCT TAAAAAAGAT GTCTACATTA     31440

TGTGTTTGAT CAAAGTCCCA ACTGATCTAC CTATTTCATT CTTTCTTTTA CCAAATTACA     31500

TGATCAACAT TATTTCTCAA ACAACGGTGA AAAGGTAACA TCTTGTTCAA AGTCTCGGAG     31560

AATTCGGACT TTAATTTGAG TTTGGTGATT GAATGCAATG GTCTTCCTAG CAGGTTGTGG     31620

CTTGCTAGGT GTTAGTCCTA GCTTAAGAAT TTGGGTAGTC GTTAGGTCAA GATTTGGAGT     31680

GTTTAGAATC CTATATATTC ATTCTTAACT AGAGCTGAAT TCTCATATGT TTACCTTCTT     31740

TATGACTAAG CATATAATTG ACTATCATCT ATCTATCTAT CTTCTATCAT ATCATCATAT     31800

TATCACCATC TCATATTATT ACTTTGCTTT ATATATATAT ATATATATAT ATATATATAG     31860

AAGAGCCAAG TTGTGGACGA CCAAGGGCAA ATTTGTCATT TCATAAATAT TCTAGAATGT     31920

TTGTTTTTAA AAAAGTGGTA ATAGATTTAT AATAACAATA CAATCAAATA TCTTTTCTTA     31980

AATGTCATGT ATATCCTAAT GATGTGACAT TTAATTTAGA CAGAAATTTT CTGTAGATTT     32040

TTTTTTTGTA GTGTGATACT TTCATTAAAC CAAAAATATC TATTAAACAT TTAGTAATTT     32100

TAATATTATT TAAGGGCGAA ACAATTATTA TATAATTAAT GATGAAAATT TAGAAGAATT     32160

CATACATCTC TGTACTTTTA AATTTGCATA TAAAAGATT TTTTTTATAA TTGTTTTAAA     32220

ATGAAGAGTT TCTATTAATT AGCTTTTTAC AAACAATAAC AAAGTGCTAA GCTTGTCTTG     32280

ACATGTTTTT GAAAGAAAAA TTTGAACTTA TTTAAAATAA AATGTGTTTG AATAGTTAAT     32340

ATTTTATCCT AAAAATACTT TGAAAAATTA TTGCGTAAAC ATGTTTTTAA TATTTGTTAC     32400

AGAATATGAC CAAAATTCGT ATCTTGATTA TTAAAATCAT CTTTAAAATG ATATATCAAA     32460

TTTTTTAATT AATTAACTTT TTAAAAACAA TAATAAAAGC TAAGTTTGTT TTGACATGTT     32520

TTTGAAGGAA ATATTAAACA AATTTAAAAT AAAATGTGTT GAATAGTTAA TATTTTGTTC     32580

CTAAAAACAC TTTAAAGAAT TCTTATGTAA ACATATGTTA ATATTTGTTA CAGAATATGA     32640

CCACTAAATT CGTATCTTCA TTATTGAAAT AATCTTTAAA ATGACGTATC AACATTTTTA     32700

ATTAATTTGA AGAAATATAA AATTACATGA CAAAGAAAAA AACAATGTTT GACTATTAAG     32760

AAATTAATGA TTCGATAATG TATTCATCAA AAGATTAAAA AATAAAAAAA ATCAATTTTA     32820

AATAATAAAT ATTTTCTTGA TATATAATAT GATAAACTAT TTAACAGGGG AAAATTTGAC     32880

AAGAAAAAAT ATTAATATTC AAATTCTAAG GAATATAAAA ATACAAAATA AAGAAATATG     32940

AGTAGTTAAA AAATAAAGAA AATAAAAAAT GAAAATGTCA ATATCAAAGG GCTTGAGAAA     33000

TATAGAGGAA AAAACAAAAT TAAAAAATAA ATAATAACTT GAAAAAGAAA AATAAGTATA     33060

TTGGTTATTT TGTGGGGGTA AGATTCAAAG TTTTCTTTCA CGGCATGATA ATTAGAGTGT     33120

AGTATAAAAT TTTTGATTAA TATATATATA TATATATATA TATATATATA TATATATATA     33180

TATATATATA TATATATATA TAACATTATG TCAATTCTTA TTGTATATAG ATACAAAATT     33240

GCTTTCGTGA TATTTTTTAT TTTTGTGGAG CTAGAAATTG ATATTTAAT AAATATTTTC      33300

AATATTTAAA ATATAACATT ATGATAATTT GTTATTGTAT ACTGAAATAA ATTTGATTTC     33360

ATGATTGTAT TTAGTGTTGT GGAAGTTAAA AATCAAGTTT TTAATAAATA CTTCAATAT      33420

TAATACCAAA ATAAATAAAA GTATTCTATT ATCGAAGACA ATAATGAAAT GTATCAAAAA     33480

ATTCACCAAC AAAGCAAACT ACAAACACAT TATACTTAAG TTGAAGCAAT AGAGATTTTA     33540

AAGGCTTTGA ATCGATCTTT ACGTGGTTGA TCTATGATTA GTATTTTATC AGATACAAAG     33600
```

-continued

```
CTTATGGTAT AAATACTACA AAAAGAAGAT GATAACATTG TAGAAAATAG ATACCGTTTG    33660

CGATAATATA TGAAGATCAT GAACTTTTTC AAAGATATCA ACATTTAATA TATTACTCGA    33720

ATGTGAAATG TTTTAATTCA TAATCTAACG TAATTCTCTA TTTTCTTGTT GCATAGAATG    33780

TTTTTGGAAT TCAACTTCTC AATTTGGGTT GTAAACTACA CATTTATATC GTATGAACAT    33840

TTGAAAAAGG TTATTAAGTA ATATATTGAA GTTGATTACT GGAAAAAGAA AATAGTATAA    33900

TGTATAGAAA TCTCATATAT TTAGAGTCTA ATTACATCAT ATCCCAGAAG TTTTCTCAAT    33960

TACAAAAATC TCGATTGTTT CGTTTTTCTC GAATTATTCA TTGTTTGTTT AATACATTAC    34020

TAATGATATA TATTACTTCA TGAGAGAGAT GTATCCGAGA GGGGATATTA TGTATTCGAG    34080

AGGGGATTAT GATATCTTAA GTTGTGAATT TATGTAATTT TTTCAATAAA ATATATGAAA    34140

TTATATTGGA CCCGAGACAC GGGCCTTAAA TTATCTAGTA CTATATAGAA GAGCCACGTG    34200

GGGGACGACC AATGGCAAAT TAGCAATTAT ATTATTATGC AAGGGTAAGA TGGTAATTAT    34260

GCATGATTGA TATTTTACCA AATCAAGCTT TCTTTTGCTT TCTGTTCTAG ATCCTTCTAG    34320

ATCTCTTTCC TCTACTTACA TATATAATTT ACAATTGCTA ATGTCAAAA GACAAAGTGT    34380

TACAACCTTT CTTTATAAGG TTAACCAATA AACAGAAACA GAAATAAGAT GAAACAGAAA    34440

AAAAAAATAC AAAATAATTT GAGTCTACAA AAACTACCGT GTCTCCTTAG GAAATTTAAT    34500

CCATCACTGT ACCCGAGGTT ATGGATTAAA TTCTCCCAAG ATAAAATGGA TTAATCCTGT    34560

TAAAGAAATA GTGGTACTTC AAACTTCTTT AACTTCAGTG AACTTAAGAA CAACAACAAG    34620

TCACACAAAC TCAGTCGATC GACACTTTGA TTTTGAGAGG AAAATATATG TAGAGTAGGA    34680

AAATTTCAGT GTTAGAAAAA ATGAAAAATA ACTTTCTTTT ATAGCCATTT TCAGCAAGAA    34740

ACGTGTATGT TCAGAAAAAT CTGTTCAGAC CCGTTTTATA CAGAAAGTTG TGTCTTTTGG    34800

AAAAAAATAA CAACTTTTCA AAAAATGTGT CTGTTAGGAA AATAACAGCT TTTCCGAAAG    34860

TAACGACTTT TCGGAAAGAT TAACAACTTT TCGAAATGTT ATCGTTACCC ACGAATTAAT    34920

TCTGTTAATT AACTAATTAA CTAACATTCT GGATTAATTT ATAAGAGATA ATATTAACAT    34980

GATTTATTTG ATTACAAAAT TGATTAAATA AATTTTATCC AAAAATTTTA TCAATCACAT    35040

CATTTGCCAA ATCCAAGTAC AAAGCCGAGG TCAAGGCCGA GCATCGACGA CGACGCGAGG    35100

GGGCACCTCT TCTTAGCTCT TTAAGAAGTA AAGAAAGTGT TTCCTTATAT AAGGACAACA    35160

ATTTCCCTTT CTCTTGCCGA TATGGGAGAA ATGACACTTT CATTTGCACT TTGCAAATGA    35220

CTTTTCATTT TTCCTCCAAA ATAGTTCCCT TACCTTTCAT ATTCTTACTT TTCATATTCT    35280

ATCTTTTCAT ATTCTCTCTT TTCATATTCT TTATTTTCTT TTCTCATTCA CACTTGCTAA    35340

ACCCAACAAT TCCCAACATG AATGGGGAAT GACTATTGTT AATTCATATG CATAAAAAAC    35400

TTGGATGTCT TGTAAATAAA TGTTAATCGC ATCTGGATAA ATAGGTTTCC CTTTAAACTT    35460

TCCGTAGTGA ACATATATCA GATATACTCA GTCAATCGGT AGATTTGATA TCTTTGAACC    35520

GTCGAGCTTT GGTGTATACC GAGACAACAT AAGTCACACA ATCAACCCTT GAACTGTTCT    35580

TAGTTCTCAT TGTTTTGTTC GTTTCAGCCA TGAACACATC TCGGATAGTA AGTGCTTAGA    35640

GAACTGGTCT TACCGAATTC TCCTTAAAGT GGCTTACACT TCACACTCAC ATAGGTGATT    35700

TCTAAATGTG TTATCCCGTA GACACACCTT ATTGTATTGA TGTCTTAAAG CAGGTTGTGG    35760

CTTGCTAGGT GTTAGTCCTA ACTTAAGAAT TTGGGTAGTC GTTGGGTCAA GATTTGGAGT    35820

GTTTAGAATC CTATATATTC ATTCTTAACC ACAACTGAAT TCTCATATGT TTACCTTCTT    35880

TATGACTAAG CATAGAATTG ACTATCATCT ATCTGTCTAT CTATCTTCTA TCATATCATC    35940
```

```
ATAGAAGAGC CAAGTTGAGG ACGACCAAGG GTAAATTTGT CATTTCATAA ATATTCTATA    36000

ATGTTTTTAA AAAAGTGGTA ATAGATTTAT AATAACAATA CAATCATATA TATCTATTCT    36060

TAAATATCAT GTGTATCCTA CTGATGTGAC ATTTAATTTA GACAGAATTT TTCTATAGAT    36120

TTTTTTTTGT AGTGTGATAT TTTCATTAAA CCAAAAATAT CTATTAAACA TTTAGTAATT    36180

TTAATATTTT TTAAGGGCGA AATAATAATT GTATAATTAA TGATGAAAAT TTAGAAGAAT    36240

TCATACATGT CTGTACTTTT AAAATTGACA TATGAAGACT TTTTCATAAT AGTTTTAAAA    36300

TGAAGANTTT CTATTAATTA GCTTTTTACA AACAATAACA AGTGCTAAGC TTGTCATGAC    36360

ATGTTTTTGA AAGAAAAATT TGAACTTATT TAAAATAAAA TGTGTTTGAA TAGTTAATAT    36420

TTTATCCTAA AAATACTTTG AAAAATTATT GCGTAAACAT ATTTTTAATA TTTGTTACAG    36480

AATATGACCA AAATTCGTAT CTTGATTATT AAAATCACAT CAAATTTTAA TTAATTAACT    36540

TTTTAAGTGA ATAGGTTCTT TTGCTCTTCT GATTCTTGTT AAAAGACGTC TACAATGTGT    36600

CTGTTTTTAA ATACTATATT ATTGCACCTC ATGATTGTTA TAAACATTCA GGGGATTATA    36660

TGATGATATA CATCTGCCCC TGACCTATAA CTTAATATTT GTAAAATACC GTCATCATAA    36720

TCATGTGAAA ACTCATCTGC AGGTAATAAA TTTACTGGGA AATTCCAATG CAGCAACAAG    36780

TGGGATATTC GTGTCCAAAG AGTTCGAATT GTTGAATTTA TGCGCACCTA GAATCAACCA    36840

TCGACACAGT GTTTGTGATA AGTTATTTAG TACTTTATGA TTCCAATCTA ATATCCATAT    36900

TGTAGTATTT TCTCCAACGT TTTGGCCTCA CGATGCAACA CTATTGTGTT GTGTTTTTTT    36960

TTTTTCAGAA AGAATTGAGA AATTGAAAAT GTAGTGTGGC AGTGTGGGGA CAGAACAAAA    37020

CAGTGGCTTT TTTTTTTAAA AAAAAAAATT TAAGTGATTT CTTAGAACAC TGTATTTGTA    37080

ATTTTTAAGA TCCAATAAAA TCGTTTTGTC TTAATCTTCT TAAAATAGGT ATGTATTATA    37140

GATCATCTTT CTTTATGTTT ATATTTTTTT CGTTTTAATT TATATGATAT AATATAAAGA    37200

TGTTTTTTTG AATTAAATAA TTTCTTTTTG CACATGTCCT AAACTAACAA AATAACAATA    37260

GAAATGACAA GAACTTATGC CCAAACATAA CAAAATACAA CTGAAAAAAA CAAAGAGGCA    37320

TATCGCCCAA TTTCTTCAAC TCCTCCACTC GCTTCGAATT TTGCCCCCAA GGTCTGTTCA    37380

TCGGCTTTTA TGGGTTGACT CGATGAAGGA AATTTGAGCC TTCATGGCTC TCCGAGATGC    37440

AAAGGGAAGG TAAGAGTTCA TAGTAAAGCT CGACAGTTTT CACATGTAAA AAAAAAAAGC    37500

AAGAAAATGA GCATTAATAC TAAAAAATGA CAACATAACA TTGCAAAAAA TGAAACTATA    37560

GGACTTATGG TGAAAAGAAT TATTGCAATA AATAAAAAGG GGCGAGGCCT ATGATAAACT    37620

AGGCAGGGAA GGATAGGTAT CAAGAGTTCT ACTACACTCA ATTGAATCCT GACAAAACAA    37680

ATACATTTCA ACCAATATAG CTTTTACCTC TAACAAATAC GATAGATATA AGATTTAAAT    37740

TTCTATCTTT GTTTAGAGAG GTGCACCCAT TATTATATGC TACTTTTGAT ATAGATGTCA    37800

CTTCTATATT TAAATACTAT TTGGAAAATA TAAATTACAA CGTATAATAC GCACAACAAA    37860

GTCACAAACT AATTACATAT AGATTAACGT AGAAGAAGGT AACAAGAAGG GAATGAGATA    37920

CTAGAACAGA GAAAGGAGAT GAGAAGTAAG TCAAAGCCAA AATTTCGACA TAATTTTCAT    37980

AACCGTTCTT CTAACTCCTA ATGTTATTTA ACAAATAGTT ATTGGGCCTA GATCTCAAAT    38040

AAAAGTCTCT AATAGCCCAT AGGCCCTTAC AGAGTCAACT TGATTCACAA CATACAACTC    38100

TTTTATGTTA TGCAACATAT GAAAGTAACG TCTACTCAGA AGAGCATTAT GAAATCTTTT    38160

TATCACACAA GACTCCGAAG GCAAGACTAG CTCCATTTCA TCCACGTTGT GTCAATACAA    38220

TGTGTGACAA ATATATATAA ATTCAAATAT GTTAATCTTA ATACACATCT TAATATTCAA    38280

ATTCACTAGT TATTTAATAT AGAAATCCCT TAACCATAGT TTGAGCAAAC ACATCATTGT    38340
```

-continued

```
GTTCGAGTTT TCTTAGAAAT TAGAATCAAA ACAATGTTTC ATCATTTTGT TTCGCAAAGC    38400

TTAACAGAAC AGGCAAAAAA GACTTTTGAA ACTTGTGATG GTAAACATAT ATAATAGTAT    38460

TTGCGGAGAA ATAAAAGCTT TAAGTTAAGA AATTATATTT TAAAAACATG TTAATATTAT    38520

ATCTGGATTA AATAATTAAA AAAAATGGTG TCAATAAAA ATGAAAAGTA AAAGTAATAT     38580

AAAGTGAGCA GAGTATTATT CTGATGGGAA ATTTGGATTA GCTTTCTATT AAATTAATCT    38640

ATCTAAACCT AATTATGAAT TTGGACTTTG TAGTAGACAA TTAAGGGCCC GTTTGGATGG    38700

GCTTAATAAA AGCAGCTTTA AAAAAGTACT TTTGAAAGTG CTGAAACTTA TTTTTAAAAT    38760

AAGCAGCTAT GCGTTTGGAT AAAAGTGCTG AAGTTGTTAT GCCAAACATG AAAAGGGAAA    38820

AATAGAAGAA AGAGATGTTA GAGTTATATG GGTAATTTGG AGATTGTATA ACAATATTAA    38880

GGGAAAACAC ATAAAAATGT GGTCAACTTA AAACAGCTTA TAAGCTAAAA AAAAAAAGCA    38940

CCCCTACCCC AGCTTTTAAC TTTTAGCTTA AAATAAGTTT TTTTTAACTT AAAATAAGCT    39000

ATTTTGAGCA TTGCCAAACA GTTAAATAAG TCAAAAACCA GCTTTTAAGT CAGTTTGACC    39060

AGCTTTTAAG CTGAGCCAAA CAGGCTCTAA GTGATTCATG CTTTTGCTTT TTAGTAGCAC    39120

TAACTTATCT TTATAATTTT TTTAATACAA TATAATTATG CATGATTTCC TGTATTAATT    39180

TTTTAATATA CTGAGATCTT TTCTCCACTA ACCCCAATCA CAAAAAAAAG TCTTTTTTAA    39240

GCATTAAACC CAATTTGTGT CATTAGTTAT ACCAATTAGG AGAGAGATAT TTTTTTTTCT    39300

CCATCAAGTA AAAAGGTTAG TTAACTCATC TACTCTATTG AAGAACATGA CAAAAATATT    39360

TGATAGTAAG TTCAATCTAG ATCTTAAGTT GGATTTTGTT TATGAGAAAG TAGAAAAATG    39420

AAGATTTTTA AAATCCATTG AATAAATAAT GTGACCTTGT GAAATTCGGA TACATATGCT    39480

GCCCAATCAG TAGGCTGAAA CTTATTCCTT ACTACTGCTA TGAAAAAATG AAATTGTGAA    39540

GTTAAAAATA TTTTTAAAAA CTAAACTTAA ACTTTTTAGG GGTATAGGTG GGTGGGTTGG    39600

GGACTAGTAG AATGGGGTGG GTAGGGGAGG TTAGAAAAGA GTTTTGGAAA ATGTTTTCCT    39660

TAAGTTTGGA AGGGAAGTCA ATTTCCTTAA ATTTGAGGAA AATGATTTGA TTTGAAAAT    39720

ATTTGACCCA ATCAAATATG AGAAAACTGA AAACTTCATA CTAAAGACAC CCTCATTTTA    39780

AAATAAAAAA CAATTATGAT CTTTTTCTTT TATTTCTGCA AAATTAAATA TTTAAGTACT    39840

TTGCTACTGG TTGAATGACT TACTGACAGC TATGTGTGGC AGTGGAACCG GTACCTACCG    39900

GTTCCCGGTC CGGTTCGGTA CCGGTTAGGA CCAAAATTTT CCGGTTCCAG GACAGGAACC    39960

GGGACGGAAT TAGGTAAAAT CCGGAATTTA CCGGTTCCGA TAATTACCGA TCCGGTCCGG    40020

TTAATTATTT TTTTTTAATA CAGCCGTTAC TAGCCGTTGG GTTATGGCTA GTGCCCCCCC    40080

CCCAACGGCT AGTTGAAGAG AAATTCATCC AATAGGGCCC CTACCCCACC CCTAACTTTT    40140

TTAATACCCT AAAGTTTTAA AAATTATACT TTAACCCATT TTTTTACTTA TAAATACCCC    40200

TAAATTTCAT TCTTTTAAAT CACAATATCA TCTATTCATC TTCTACTCTC TCAACTCTCT    40260

ACTCTCTATC TCTAATCTCT ATTTCTATAA TATATAATAT CTTAAATTCC GGTGTTGCCT    40320

TACTTGGTCT TTGAAATTAA ATTTGGAGCT TCAAAATTCA ATTTTCAACT TTCCACGTTC    40380

GGCTTTCGGC GGTCATAAAC GTCTACTTTT AAGTAGACGT TCGGTACATT CGTTCTAACT    40440

TTTATTTTAC GTTTCGTTTA TATTTAAATA ATTATTTATT TATTTGTGAT TTATTATTTG    40500

CATAATTGCA TAACATTTTT CGTATTATAT TTAATCTCAC GTTAATTTT TAATATGGA     40560

TTTCGGAAAA AATATCTTTA AAAAAGGAA AGGGGAAAAA AAGTGCATTA GAGCGTGTAA     40620

GAAATGTTTG TAACTTTACA TCCTCCGATA ATGCAAAAAC CGGTAGTTCT TCTAAATCAA    40680
```

```
AAACTAAAAA ATCTACTATA TTAAGAATAA ATACGGATGA TTATACACAT GTTGATGATA    40740

CGGTTTTTAA TATTGATAGT AATTCAGGAT TAGATCCTTA TCATGAACAT TTACAACGTC    40800

GCTTTGGTAA TTTTGATGAG GATTTGCCTA GTGATAATGA TAATGATAAT GATATTGATA    40860

ATTATACTGA TACGCCTATT TTTGATAATG AAACTCAGCC ACCTACGGCT ACTACTACTC    40920

CTAGTCCCGC TCCCTTTCGT TGTCCTGCCC CAGTTCCCCC AGTACATCCT AGGCCTAAGG    40980

TAGAACGTGT TAAAAAATCG GTTGTTTGGC AATTTATGAC ACAAAACGAA GATAAAACAC    41040

AAGCTATTTG TAATAAATGT AAACGTATAT TAAATCATAA AACTGTGGGC AAATCTGGCG    41100

GGATGGGACA TTTGAGTAGT CATTTAATGT CTTGTTGTAA AAATGAATTT TTGCATGCTA    41160

AAGCGGTAGC GGAAACTAAA AAAAACGGTA CCCCCCTTCC TGAAAATGTA GGAGTAGGCG    41220

GCTCTAAAAT GGTACAAACA CAATTAAATC CGTCTAATGT TTCTGGCTCT AATTTACTAC    41280

CTTCATATAG TAGAGAGAAA GATCTTGAAG AACTAGCTAA AATGATATGT GTTATGGGTT    41340

TGCCATTTAG TTTTGCTGAA AATCCCGGTT TTATACATTA TATTCAAATT GTATATAATC    41400

CAAATTTTAA AGTTTTGCTA GAAATACAAT AAAAAAAGGT TGTATTTGAT TATCATGCAC    41460

AACATTTTCA ATATCTTCGT TGTTCATTTT ATTATAATAC TTGTAAAATA GCTATTACTT    41520

CTGATATGGG TCGTAGTGTA AATGGTAACA ATTATTTGAC TGTTACTGCA CATTGGATTG    41580

ATGAAAATTG GTATATGCAA AAAAGAATTT TAGGTTATAA ATGTTGTCAA ATGCAAAAAA    41640

AACGGTAGTT ATATTGCTCA AACTATTTTA GATATTTTAC AAAGTTATGG AATATGTGAT    41700

AAAATAAGTA GTATAACCTT AGATAATGCT TTAAGTAATA ATTCTGCTGT TCAATATTTA    41760

AAAACTACAC TTTGTCCTTT CTATGGTGAT AATTATCATA TTAGGTGTAC TGCACATATA    41820

TATAGTTTGA TGGTTAGAGA TGGTGTAAAT ATGTATGATA ACGGATGTAC GAAAGTTGAA    41880

AATGCATGTC ATTTTATATT TAAATGTCAA GTTAAGTCTC GGCGTAAAGA TTTTCAAAAT    41940

CGTTGTTTTG AAAATAATCT TCCACCTAGA AAAATTCCAA AAACAGTGGC TACTAGATGG    42000

AATGCTTTAT ATGAAATGCT TGTAGTCGCT TATGAATATC GAATACCCTT ACAAATGGTT    42060

TGGAATGCTC ATAATTCTGA TATGACATAT AGATTAGATG ATAATGATTG GCGTGATATA    42120

AATGAACATA TAGATTTCCT AAAAGTTTTT TACTTAACTA CAAAAAGAAT TTCTGTACTT    42180

TATAGTCCAT CAATTTGTAC TGTTTTGCCT GATATTTGTA TGATTTCTTC TAAATTATAT    42240

AAATTTAAAA ATAAACCAAG ATTTCAACAA ACCATTGAAA AAATGATTAT AAAATTTAAA    42300

AAATATTATA TTCCTATTCC TCAAATTTAT TTAACTGCAT GTTTGTTACA CCCTCAGTAT    42360

AAAGATTTCG GTTCATCAAG AATGGTTGAA AAATATATTT TAACTTAGAT ATTAATGATG    42420

AATTAGAAGA AATTCCTAGT TGTCAACAAG TTAAAGATAG CATAAAAATT GAAGCAAGAA    42480

AATTGTATGA TTTATATAAT GCTAATAAAA ATTTATCAAG TGAAATGAA CCTGAAAGCT    42540

CTAGGGTTAG ATTTGATGAA AATAATATTG ATAATTATTT AGAGGATTAT CTTGAACTTT    42600

CTCACGATAA TAGAAATGAT TTTGATGCAT ATATTAATCA AATTACAGAA CCTACTGAAG    42660

ATGTTCTCAA ATGGTGGAGA GATCGCACCA AAGGATTTCC AAAACTAGTA ACGATGGTTC    42720

GAGATATATT AGCAATGCAA GCGTCGTCGG TAGCATCGGA AGGCGTCTTT AGTACAGCAA    42780

GGTTTCAACT TGGAGAACAT AGGCATTCAC TAGCAGCCAA CAGCTCGGAG ATATCGGTAT    42840

TATTTTGAGA TTGGATTAAT GCCGAGAGAA GAAATTTGGG TCGTAAACCA CTACCGACCA    42900

AATTTCAAGA TGACGTTGAT GAAGTAATGC AGGATTATGT GACGACGGGA TTGAAGCAAT    42960

GGAAGATCTT TCTATTCAAC CTATTCCCGA ACATGTTACT AAAGAAATGT TGAATGATTT    43020

ACGAAGGGAT TTATATGGTG GCACCAACTA TTAATTCAAA CTAATATTTT TGTAAATGTA    43080
```

```
ATTGTAATAT CAAATATATA TTAATAAAAA TATAGGCTAT TCGCCTTAAT TTATTTTTTA    43140

ATATTGTTGT ATTAAATTTA ATTTTTGATA TAGTCAATTT TAAATTTTAT AACTTTAAAG    43200

TTTAAATTCA AAAATTTCAA ACTTTAAGAG TTTGAAATTA AAATTTTATA ACTTTAAAAT    43260

TTGAATTTAA AATTTTCAAA CTTTAAAAGT TTGAATTTAA AGTTTGAAAA TTTAAATTTG    43320

AAACTTTAAA ATTTTGAAAA TTTTAAATTA AAACTTTAAA GTTTATATTA ACTTTAAAGT    43380

TTGAAATTTA AATTTAACTT TAAAATTTGA ATTTAAAATT TTCAAATTAG TTGGAATTTA    43440

AAGTTTGAAA ATTTAAATTT ATGACTTTAA AGTTTGAAAT TTAAATTTTT AAATTGCTTA    43500

ATTATTATAA TAAAAATTAG ATTCAATTAA TTTTTTTTTT AAAATCCGTT TCGTCCCAGA    43560

TACCGNTCCG GTCCGGTATA CTACCGGTTT ACTACCGGAG CGGGACGGAA CAATATTTAT    43620

TTTACCGATT TCCCGGACCG GGCCGTTCCG GTTCTGGAAC TTTACCGGTA NACACAGTAC    43680

CGGTTCCGGT AATAACTTAT CCGGTTTTCC CGATTCCGAT ACCACTGCCA GCATACTGA    43740

CAGCAGAGGC GAATTTAGGA ATTATAGTCA NTGGGTGCCA ACCAGAGCCT AACCCACATG    43800

ATTTGATAGA GGTGCACGTG CATCCGTTAA NTTCAAAAAA ATTACATGTA TATATGTATA    43860

TCTATCGTGA GATACTGACA TAAAGTAGAA TATAATCAAC AGTGCACCCT CACGGGTGGC    43920

GTGGCATCCT CACGGGCCTT GATAGATCCG CCGCTGGCTG ACAACACTAT TTTTCTCAAT    43980

TTTTTTCATT CTATTTTTTC ATATTGTGGT ATGTTTTTTT TCTTCATTAA TTTATACTTT    44040

GACATTAATT ATTGTTTTTG ATTACATATT TTAAACTCTG TTGTTTATTT TTCTGTAAAA    44100

AATTTTCCAG TTATATTGAA CATGTACACA TATAATCAT ATATTCATTA TGCAAAAAAT    44160

AATTATTATA CTCCATTTTA AGAATTCATG TTTTGATATT CTATAATGTA GAAATTGCCA    44220

ATGTCTACAA TGTGTTTGAT GAAATGACAA CCACTTGTTT TTATCTTCGT CAGTATAAAA    44280

ATTGGATTTG CTTCATTTAG ATTAAATAAA TATTTTACAG GTCACATATT ATATTTATAT    44340

TGTGAAAGAC AAGAGACATT GATTAAAAAA AGACTTGAGA AGTCAATGGG TTTGTATTTT    44400

AATATTTCAT TACTAAAAGA CTTGTATTGT ATATTTCAAC TACTACACTT GTTTTTTTCT    44460

CCAATAGGTT CATCATTATT TCTCAAACAA AGGCTTCTCT AGCTAAACTT CAGCCTCTGT    44520

AAAGGTACCA TCTTCTTCTT TGCTATACTT CATTCGAAGC AGAAAAACAT GAAAATGATG    44580

ATTAAGTCAG CACTTTTGGT ATTTAAAGGC CTTGTGATTA GTCTTTGTTT GAATTCTAGA    44640

TCTACCTATT TGATTAGTCT TTTTGTTGTT TGCCTTTCAA CCAAACTACT TCTTCGATCT    44700

CTTACTTCAA CAAAATATGT CAAAAGGTA TGAACATGCT TAATCGGAGC TCTCTATTGA    44760

TTCTACTTCA GCTACTCTCA CAAAAAATCT TATTATTATT TTTTATCAAA ATAAAAAGTG    44820

TAATCTTTTT TCATTAGCCC AAGGAGATAG GAGAAAAATA TTATTAGAGA GATCATTAAT    44880

TTAATGACAT TTTACTTAAC AGTTGTGAGA TTTTATGTTT GTGATTTCAT GTCATAAACA    44940

TTTTGATGTG TGATTAAGAT TGACATTTCC AATTGTGCGA ATCTAAAATT ACTATATGTG    45000

AAAATAGTGA TATTATTGAT TATTCTTATC TTTTCATCTT CTTTCTCCTG TTAAAGTTTT    45060

ATCTACTTCT TATTCATCAG GTCTTGAGAA AAAGTAGAAT CATGGAAAAA CGAAAAGATA    45120

ATGAAGAAGC AAACAACTCA TTGGTATGTT ATTTTATAGA GTAAACTGTA AGTATTAAA    45180

TTATAGATAT GTGACTTTAA AATGTATTAT TTTGGCAGGT GTTATTTTCT GCTCTTAGCA    45240

AGGACATTGC CGATGTTCTG GTTTTCCTAG AGAATGAGGA AAATCAAAAA GCTCTTGACA    45300

AAGATCAAGT TGAAAAGATA AAATTGAAAA TGGCATTTAT TTGTACATAT GTTCAGCTTT    45360

CTTGTTCCGA TTTTGAGCAG TTTGAAGATA TAATGACTAG AAAAAGACAA GAGGTTGAGA    45420
```

```
ATCTGCTTCA ACCACTTTTG GATGATGATG TCTTTACTAG CCTCACCAGT AATATGGATG    45480

ACTGTATCAG CTTGTATCAT CGTTCTTATA AATCAGATGC CATCATGATG GATGAGCAAT    45540

TGGACTTCCT CCTCTTGAAT CTCTATCATC TATCCAAGCA TCACGCTGAA AAGATATTTC    45600

CTGGAGTGAC TCAATATGAA GTTCTTCAGA ATATATGTGG CAACATAAGA GATTTCCATG    45660

GGTTGATAGT GAATGGTTGC ATTAAGCATG AGATGGTTGA GAATGTCTTA CCTCTGTTTC    45720

AACTCATGGC TGACAGAGTA GGACACTTCC TTTGGGATGA TCAGACTGAT GAAGACTCTC    45780

GACTCTCCGA GCTAGATGAG GATGAACAAA ATGATAGAGA CTCTCGACTT TTCAAGCTAG    45840

CACATCTACT CTTGAAGATC GTTCCGGTTG AACTGGAGGT TATACACATA TGTTATACAA    45900

ACTTGAAAGC TTCAACTTCA GCTGAAGTTG GACTCTTCAT TAAGCAGCTT CTAGAAACCT    45960

CTCCAGATAT TCTGAGGGAA TATCTAATTC CTCTGCAAGA GCACATGGTA ACTGTTATTA    46020

CCCCTAGCAC TTCAGGGGCT CGAAACATTC ATGTCATGAT GGAATTCCTA TTACTTATTC    46080

TTTCTGATAT GCCCAAGGAC TTTATTCATC ATGACAAACT TTTTGATCTC TTGGATCGTG    46140

TCGGAGTACT TACCAGGGAG GTATCAACTC TTGTACGTGA CTTGGAAGAG GAACCAAGGA    46200

ATAAAGAGGG TAATAACCAA ACAAATTGTG CAACCCTAGA CTTGCTGGAA AATATTGAAC    46260

TCCTCAAGAA AGATCTCAAA CATGTTTATC TGAAAGCCCT GGATTCATCT CAATGTTGCT    46320

TCCCCATGAG TGATGGACCA CTCTTCATGC ATCTTCTACA CATACACTTA AATGATTTGT    46380

TAGATTCTAA TGCTTATTCA ATTGCTTTGA TAAAGGAAGA AATCGAGCTG GTGAAGCAAG    46440

ACCTGAAATT CATAAGATCA TTCTTTGTGG ATGCTGAGCA AGGATTGTAT AAAGATCTCT    46500

GGGCACGTGT TCTAGATGTG GCTTATGAGG CAAAAGATGT CATAGATTCA ATTATTGTTC    46560

GAGATAATGG TCTCTTACAT CTTATTTTCT CACTTCCCAT TACCATAAAG AAGATCAAAC    46620

TTATCAAAGA AGAGATCTCT GCTTTAGATG AGAACATTCC CAAGGACAGA GGTCTAATCG    46680

TTGTGAACTC TCCCAAGAAA CCAGTTGAGA GAAAGTCATT GACAACTGAT AAAATAACTG    46740

TAGGTTTTGA GGAGGAAACA AACTTGATAC TTAGAAAGCT CACCAGTGGA TCGGCAGATC    46800

TAGATGTCAT TTCGATCACT GGTATGCCGG GTTCAGGTAA AACTACTTTG GCATACAAAG    46860

TATACAATGA TAAGTCAGTT TCTAGCCGTT TCGACCTTCG TGCATGGTGC ACGGTCGACC    46920

AAGGATGTGA TGAAGAAGAG TTGTTGAATA CAATTTTCAG TCAAGTTAGT GACTCAGATT    46980

CAAAATTGAG TGAGAATATT GATGTTGCTG ATAAATTACG GAAACAACTG TTTGGAAAGA    47040

GGTATCTTAT TGTCTTAGAT GACGTGTGGG ATACTACTAC ATGGGATGAG TTAACAAGAC    47100

CTTTTCCTGA ATCAAGAAA GGAAGTAGGA TTATTTTGAC AACTCGGGAA AAGGAAGTGG    47160

CTTTGCATGG AAAGCTGAAC ACTGATCCTC TTGACCTTCG ATTGCTAAGA CCAGATGAAA    47220

GTTGGGAACT ATTAGAGAAA AGGGCATTTG GGAATGAGAG TTGCCCTGAT GAACTATTAG    47280

ATGTCGGTAA AGAAATAGCC GAAAATTGTA AAGGGCTTCC TTTGGTGGCT GATCTGATTG    47340

CTGGAGTCAT TGCTGGGAGG GAAAAGAAAA GGAGTGTGTG GCTTGAAGTT CAAAGTAGTT    47400

TGAGTTCTTT TATTTTGAAC AGTGAAGTGG AAGTGATGAA AGTTATAGAA TTAAGTTATG    47460

ACCATTTACC ACATCACCTC AAGCCATGCT TGCTGTATTT TGCAAGTTTT CCGAAGGACA    47520

CTTCATTGAC AATCTATGAG TTGAATGTTT ATTTCGGTGC TGAAGGATTT GTGGGAAAGA    47580

CGGAGATGAA CAGTATGGAA GAAGTGGTGA AGATTTATAT GGATGATTTA ATTTACAGTA    47640

GCTTGGTAAT TTGTTTCAAT GAGATAGGTT ATGCACTGAA TTTCCAAATT CATGATCTTG    47700

TGCATGACTT TTGTTTGATA AAAGCAAGAA AGGAAAATTT GTTTGATCAG ATAAGATCAA    47760

GTGCTCCATC AGATTTGTTG CCTCGTCAAA TTACCATTGA TTGTGATGAG GAGGAGCACT    47820
```

```
TTGGGCTTAA TTTTGTCATG TTCGATTCAA ATAAGAAAAG GCATTCTGGT AAACACCTCT    47880

ATTCTTTGAG GATAATTGGA GACCAGCTGG ATGACAGTGT TTCTGATGCA TTTCACCTAA    47940

GACACTTGAG GCTTCTTAGA GTGTTGGACC TGCATACGTC TTTTATCATG GTGAAAGATT    48000

CTTTGCTGAA TGAAATATGC ATGTTGAATC ATTTGAGGTA CTTATCCATT GACACACAAG    48060

TTAAATATCT GCCTTTGTCT TTCTCAAACC TCTGGAATCT AGAAAGCCTG TTTGTGTCTA    48120

CCAACAGATC AATCTTGGTA CTATTACCGA GAATTTTGGA TCTTGTAAAG TTGCGAGTGC    48180

TGTCCGTGGA TGCTTGTTCT TTCTTTGATA TGGATGCAGA TGAATCAATA TTGATAGCAG    48240

AGGACACAAA GTTAGAGAAC TTGAGAATAT TAACGGAACT GTTGATTTCC TATTCGAAAG    48300

ATACAAAGAA TATTTTCAAA AGGTTTCCCA ATCTTCAGTT GCTTTCATTT GAACTCAAGG    48360

AGTCATGGGA TTATTCAACA GAGCAACATT GGTTCTCGGA ATTGGATTTC CTAACTGAAC    48420

TAGAAACACT CTCTGTAGGT TTTAAAAGTT CAAACACAAA CGATAGTGGG TCCTCTGTAG    48480

CGACAAATCG GCCGTGGGAT TTTCACTTCC CTTCAAATTT GAAAATACTG TGGTTGCGTG    48540

AATTTCCGCT GACATCCGAT TCACTATCAA CAATAGCGAG ACTGCCCAAC CTTGAAGAGT    48600

TGTCCCTTTA TCATACAATC ATCCATGGAG AAGAATGGAA CATGGGGAG GAAGACACCT     48660

TTGAGAATCT CAAATTTTTG AACTTCAATC AAGTTAGTAT TTCCAAGTGG GAGGTTGGAG    48720

AGGAATCCTT CCCCAATCTT GAGAAATTAA AACTGCGGGG ATGTCATAAG CTAGAGGAGA    48780

TTCCACCTAG TTTTGGAGAT ATTTATTCAT TGAAATCTAT CAAAATTGTA AAGAGTCCTC    48840

AACTTGAAGA TTCTGCTCTC AAAATTAAGG AATACGCTGA AGATATGAGG GGAGGGACG     48900

AGCTTCAGAT CCTTGGCCAA AAGAATATCC CCTTATTTAA GTAGCATTAT GGTTGAAAAG    48960

TAGATTGTAC TTTGCTGGGT AGATTGTATA TGATTAAGAA AATTTTGTTG CAGTTATGAA    49020

ATATTTTGT GGATTTCTCA AAGTTTCTGC AACAAAAATT ATAATTTTA TAAATGCACG      49080

TATCATWWRT TGATTTGTCC ATTTCTTTTA TCACAAGCAC ACATGTGAGT ATAGATTTGA    49140

CATAATACAT AAACATAACC TTTTAACTTT GGATTTGCAC GAGTAGGTAT AAAATTGAGA    49200

AAATGAACAG TCATCATACC TATGTAAGTG TTTGTTTATC AGACTGACTC GTACTAGAAC    49260

AATAAAATAC CTTCTTCTAA ACGTTCAACA AATTAAATGG GATTTCAGCA CGCAAATGAA    49320

TGAGAAAGGT TCACATTTAT CTTCAAGGAG AATTACAACA ATACAGGACC ACAAGTACAT    49380

TGACAGCATC ATTTCAACAG AAAAAACAAC AAGAGTTGAA AATACAATAG TTATCCTTAC    49440

TGATATAGCA CAAGAAACAA GAGTTTAAAN NNNNTATTTG TAATAAATTG ATGCAAAGTC    49500

ACTCAACAAA TGGTCAAATC GATGGCACAC GGGCTTCACC GCCACCATAA CCAGCACTGC    49560

AACCACACAA GGCTCAAGCA AGTAAATGCA GGTGAAAGAT CAGCATAGAA CTAATACCTG    49620

AAGTCTTCCT AAGAAGAAGC CAAAGAGCAA TCCCCATTGC TATATGGAGT CGATGTTGCA    49680

TCTTCATCAA TAATCCAAAC AAAACCAGGA GTGTCGAACC TCCTTCCTGA CACTGTCCTG    49740

TATATATAAA GTTTCTCAAC AGGGCAACTT TCTGATCTCC TATCCGGATG ACCCCTCTCG    49800

TCTATAACAT CAACATTAAG CCATGGCAAC TTCTAGGCTA GCAGCTTTCA TGCTTCAAAA    49860

CTTACTGAAC AATTAGACAT CCAAAGGGAT CGCATTGTCT CCAGCTTTGC AGCATTAGCC    49920

AACAGAGCCT CATCGCCAAA AGGGCAGTCT CTAGTCTCCA ACTTACGGAG GCTCTCAAAA    49980

CCAGAGAGAA CATAGAGGAG GCCTATATCA CTATCTCCCG CAAAAGCTAA GGAAAGCATC    50040

TCTAACTTCT TAGCATGGAC CCCGATGTAC TCAAACACAC GATCTGTAAG GAGACCAGAA    50100

AGAGAAAGTC GCTGCACTTC CTTGCAGTGT TGCACAATGG CCCCAAAACC AGTATCAAGT    50160
```

| | | | | |
|---|---|---|---|---|
| GGTTCAAGGA | TTAAGTAGTC | AGGAGTTTGA | GGCTCGATAA | TACACAAACA AAATCGGATC | 50220 |
| ATGTTAGAAC | GGTTCCTTGC | AATACTAACT | AAGGCGTCAT | TTGTCATTTG GCGGCAGAAG | 50280 |
| TATAAAACTG | ACTGAAGCTT | AGGGCAGCCC | ATTGAGACAG | CTACAAGGCC TTGCTCTGTC | 50340 |
| AAGGATACAT | TAGGTCGTGG | AGCAAATAGA | TCAAAAGGAA | ACACCCTAAG CTCTTGAAGT | 50400 |
| TCCTTACAAG | TGTTGGCAAT | CTCCTCAAGA | CCGCTATCTT | CAATATAATC TAGCACCTGC | 50460 |
| AATCACATCC | ATTCCAAGTG | CCTTAAAGTG | TAAGCTGGAT | AACTAATTGT GCAGCAGATC | 50520 |
| CACTGGACAA | GAAAAGCCTA | AAAACTAATG | GAAGCGTCTA | ACCCGGAAAG ATATACATGA | 50580 |
| ATTGTCAAAG | TGTAGGATTC | ATGCAACACT | AAGATTCAAC | ATTAACTTAT TCTTTGTATG | 50640 |
| GCAGACCAAC | AAAATTATTC | AAAGAGTTCA | CTCGACATTA | ATTGTTTAGC TATGTTATCT | 50700 |
| CAGTAAACAC | TGAAGTTCAT | TACGCTGTTT | ATTTATCCCT | GGCGTTATCA GAATTAGCAA | 50760 |
| GACAATTAAT | AAGTTAGGAT | AATTGTTCTT | CTCTTGGAAA | CTTGTGTGTT TACAACTAAT | 50820 |
| AATCAACTTA | TCTATTTTAT | CACAAACAAA | GTTGATGTAT | TGAGCCATGA CTATTGAAAA | 50880 |
| CACTCAATAA | GTATACAAAA | GTAAAACACA | AGGTAGAACC | TACCCACAAA TGCTGCAAAT | 50940 |
| TGAAACAATT | GCCAATGAGC | TTGCAAAGAT | CAGGTATTTG | AATGGTAGCA TAGCTTAAAG | 51000 |
| TCAAAGAGGT | GAGTTTGGAG | TGGACTGGAT | AAATAGTTTG | AAAGTAGGCT GGCACAGCAT | 51060 |
| CCCAAAACCC | ACTCAAGCCT | TTGAGTTGAT | TACAGCCTGA | AAACGCTTGA GATACATTTA | 51120 |
| CAAAAACTTC | AGAACATCA | TCCTGCAAGT | CAGCAGAGTA | GGATCCTGTA CCAAATTCAA | 51180 |
| CCAACTTCGA | AGCATGACGA | AGTATCTTTG | GAAATTTCTC | AATGGGAACA GCACGATTGA | 51240 |
| GCCGAAGAGT | CCTCAAATGA | GGAGAGCGAG | CAACTAGACG | CTCCAAAGCT GAGAAGCTGA | 51300 |
| CCTCAGAAGC | CAAACAAGCA | ATGTTAAATG | ACACAAGCGA | TGTATAACTA TCAGGAAAAT | 51360 |
| GACTAAGCCA | ATGGCCACTC | AGGTCTTCTG | CTTCACTTTC | TCCCAGGTCC AGTTCTCTCA | 51420 |
| GGTTCCTGCA | GCAAATATCG | AGTTACATTG | CTTCTATAGT | TTTTATTCCC AGCCCTAAAC | 51480 |
| AAGAATAGCA | GCAAAAGAAG | GTCCAAATAT | AAGAGGAGTT | GTCATAAATC AAATGGAAAG | 51540 |
| AGATAAAAAT | GCAACATTAA | TTTGATAACC | ATGTTACAAG | ATGTTCAACC CTTTCAATAA | 51600 |
| TTCAAATTCA | TTGAACTACT | TATAATATTA | TTTACTTTTT | TTCTGGAATA ATGTCCATTT | 51660 |
| CATTTGAAAA | CCAGTGTTTG | TATATGAAAA | GTTCGAAGCC | GACTTGAAGT TGTAAATCAA | 51720 |
| ATTTGGAAAA | CAACTTATAA | CATGTTTTCC | AACTCGCTTT | CGAATGTTGA ATTATATTTT | 51780 |
| ATTWTCAAAT | GTACCCTAAT | TTTTTGGTTA | TAACAACCCC | AACTTTAATA TCAGCGACCA | 51840 |
| ACCAGAGATA | GAGATTAACA | ATGTTGCTTC | ATCTTCTAAG | TCAGATGATG GGAAAACACA | 51900 |
| TGCTCGACGA | GAAGAGACTG | TTCACACAAT | GTGGGAGGGA | TATCTCAAGG GC | 51952 |

(2) INFORMATION FOR SEQ ID NO:2:

(i) SEQUENCE CHARACTERISTICS:
        (A) LENGTH: 3997 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 85..3852
        (D) OTHER INFORMATION: /note= "Copy 1 cDNA for M1 nematode
            resistance gene of tomato"

(xi) SEQUENCE DESCRIPTION: SEQ ID NO:2:

-continued

```
CAATAGGTTC ATCATTATTT CTCAAACAAA GGCTTCTCTA GCTAAACTTC AGCCTCTGTA        60

AAGGTCTTGA GAGAAAGTAG AATC ATG GAA AAA CGA AAA GAT AAT GAA GAA          111
                           Met Glu Lys Arg Lys Asp Asn Glu Glu
                             1               5

GCA AAC AAC TCA TTG GTG CTA TTT TCT GCT CTT AGC AAG GAC ATT GCC         159
Ala Asn Asn Ser Leu Val Leu Phe Ser Ala Leu Ser Lys Asp Ile Ala
 10              15                  20                  25

GAT GTT CTG GTT TTC CTA GAG AAT GAG GAA AAT CAA AAA GCT CTT GAC         207
Asp Val Leu Val Phe Leu Glu Asn Glu Glu Asn Gln Lys Ala Leu Asp
                 30                  35                  40

AAA GAT CAA GTT GAA AAG ATA AAA TTG AAA ATG GCA TTT ATT TGT ACA         255
Lys Asp Gln Val Glu Lys Ile Lys Leu Lys Met Ala Phe Ile Cys Thr
             45                  50                  55

TAT GTT CAG CTT TCT TGT TCC GAT TTT GAG CAG TTT GAA GAT ATA ATG         303
Tyr Val Gln Leu Ser Cys Ser Asp Phe Glu Gln Phe Glu Asp Ile Met
         60                  65                  70

ACT AGA AAA AGA CAA GAG GTT GAG AAT CTG CTT CAA CCA CTT TTG GAT         351
Thr Arg Lys Arg Gln Glu Val Glu Asn Leu Leu Gln Pro Leu Leu Asp
     75                  80                  85

GAT GAT GTC TTT ACT AGC CTC ACC AGT AAT ATG GAT GAC TGT ATC AGC         399
Asp Asp Val Phe Thr Ser Leu Thr Ser Asn Met Asp Asp Cys Ile Ser
 90                  95                 100                 105

TTG TAT CAT CGT TCT TAT AAA TCA GAT GCC ATC ATG ATG GAT GAG CAA         447
Leu Tyr His Arg Ser Tyr Lys Ser Asp Ala Ile Met Met Asp Glu Gln
                110                 115                 120

TTG GAC TTC CTC CTC TTG AAT CTC TAT CAT CTA TCC AAG CAT CAC GCT         495
Leu Asp Phe Leu Leu Leu Asn Leu Tyr His Leu Ser Lys His His Ala
            125                 130                 135

GAA AAG ATA TTT CCT GGA GTG ACT CAA TAT GAA GTT CTT CAG AAT ATA         543
Glu Lys Ile Phe Pro Gly Val Thr Gln Tyr Glu Val Leu Gln Asn Ile
        140                 145                 150

TGT GGC AAC ATA AGA GAT TTC CAT GGG TTG ATA GTG AAT GGT TGC ATT         591
Cys Gly Asn Ile Arg Asp Phe His Gly Leu Ile Val Asn Gly Cys Ile
    155                 160                 165

AAG CAT GAG ATG GTT GAG AAT GTC TTR CCT CTG TTT CAA CTC ATG GCT         639
Lys His Glu Met Val Glu Asn Val Leu Pro Leu Phe Gln Leu Met Ala
170                 175                 180                 185

GAC AGA GTA GGA CAC TTC CTT TGG GAT GAT CAG ACT GAT GAA GAC TCT         687
Asp Arg Val Gly His Phe Leu Trp Asp Asp Gln Thr Asp Glu Asp Ser
                190                 195                 200

CGA CTC TCC GAG CTA GAT GAG GAT GAA CAA AAT GAT AGA GAC TCT CGA         735
Arg Leu Ser Glu Leu Asp Glu Asp Glu Gln Asn Asp Arg Asp Ser Arg
            205                 210                 215

CTT TTC AAG CTA GCA CAT CTA CTC TTG AAG ATC GTT CCG GTT GAA CTG         783
Leu Phe Lys Leu Ala His Leu Leu Leu Lys Ile Val Pro Val Glu Leu
        220                 225                 230

GAG GTT ATA CAC ATA TGT TAT ACA AAC TTG AAA GCT TCA ACT TCA GCT         831
Glu Val Ile His Ile Cys Tyr Thr Asn Leu Lys Ala Ser Thr Ser Ala
    235                 240                 245

GAA GTT GGA CTC TTC ATT AAG CAG CTT CTA GAA ACC TCT CCA GAT ATT         879
Glu Val Gly Leu Phe Ile Lys Gln Leu Leu Glu Thr Ser Pro Asp Ile
250                 255                 260                 265

CTG AGG GAA TAT CTA ATT CCT CTG CAA GAG CAC ATG GTA ACT GTT ATT         927
Leu Arg Glu Tyr Leu Ile Pro Leu Gln Glu His Met Val Thr Val Ile
                270                 275                 280

ACC CCT AGC ACT TCA GGG GCT CGA AAC ATT CAT GTC ATG ATG GAA TTC         975
Thr Pro Ser Thr Ser Gly Ala Arg Asn Ile His Val Met Met Glu Phe
            285                 290                 295

CTA TTA CTT ATT CTT TCT GAT ATG CCC AAG GAC TTT ATT CAT CAT GAC        1023
```

```
                                                       -continued

Leu Leu Leu Ile Leu Ser Asp Met Pro Lys Asp Phe Ile His His Asp
            300                 305                 310

AAA CTT TTT GAT CTC TTG GAT CGT GTC GGA GTA CTT ACC AGG GAG GTA        1071
Lys Leu Phe Asp Leu Leu Asp Arg Val Gly Val Leu Thr Arg Glu Val
        315                 320                 325

TCA ACT CTT GTA CGT GAC TTG GAA GAG GAA CCA AGG AAT AAA GAG GGT        1119
Ser Thr Leu Val Arg Asp Leu Glu Glu Glu Pro Arg Asn Lys Glu Gly
330                 335                 340                 345

AAT AAC CAA ACA AAT TGT GCA ACC CTA GAC TTG CTG GAA AAT ATT GAA        1167
Asn Asn Gln Thr Asn Cys Ala Thr Leu Asp Leu Leu Glu Asn Ile Glu
                350                 355                 360

CTC CTC AAG AAA GAT CTC AAA CAT GTT TAT CTG AAA GCC CTG GAT TCA        1215
Leu Leu Lys Lys Asp Leu Lys His Val Tyr Leu Lys Ala Leu Asp Ser
            365                 370                 375

TCT CAA TGT TGC TTC CCC ATG AGT GAT GGA CCA CTC TTC ATG CAT CTT        1263
Ser Gln Cys Cys Phe Pro Met Ser Asp Gly Pro Leu Phe Met His Leu
        380                 385                 390

CTA CAC ATA CAC TTA AAT GAT TTG TTA GAT TCT AAT GCT TAT TCA ATT        1311
Leu His Ile His Leu Asn Asp Leu Leu Asp Ser Asn Ala Tyr Ser Ile
395                 400                 405

GCT TTG ATA AAG GAA GAA ATC GAG CTG GTG AAG CAA GAC CTG AAA TTC        1359
Ala Leu Ile Lys Glu Glu Ile Glu Leu Val Lys Gln Asp Leu Lys Phe
410                 415                 420                 425

ATA AGA TCA TTC TTT GTG GAT GCT GAG CAA GGA TTG TAT AAA GAT CTC        1407
Ile Arg Ser Phe Phe Val Asp Ala Glu Gln Gly Leu Tyr Lys Asp Leu
                430                 435                 440

TGG GCA CGT GTT CTA GAT GTG GCT TAT GAG GCA AAA GAT GTC ATA GAT        1455
Trp Ala Arg Val Leu Asp Val Ala Tyr Glu Ala Lys Asp Val Ile Asp
            445                 450                 455

TCA ATT ATT GTT CGA GAT AAT GGT CTC TTA CAT CTT ATT TTC TCA CTT        1503
Ser Ile Ile Val Arg Asp Asn Gly Leu Leu His Leu Ile Phe Ser Leu
        460                 465                 470

CCC ATT ACC ATA AAG AAG ATC AAA CTT ATC AAA GAA GAG ATC TCT GCT        1551
Pro Ile Thr Ile Lys Lys Ile Lys Leu Ile Lys Glu Glu Ile Ser Ala
475                 480                 485

TTA GAT GAG AAC ATT CCC AAG GAC AGA GGT CTA ATC GTT GTG AAC TCT        1599
Leu Asp Glu Asn Ile Pro Lys Asp Arg Gly Leu Ile Val Val Asn Ser
490                 495                 500                 505

CCC AAG AAA CCA GTT GAG AGA AAG TCA TTG ACA ACT GAT AAA ATA ACT        1647
Pro Lys Lys Pro Val Glu Arg Lys Ser Leu Thr Thr Asp Lys Ile Thr
                510                 515                 520

GTA GGT TTT GAG GAG GAA ACA AAC TTG ATA CTT AGA AAG CTC ACC AGT        1695
Val Gly Phe Glu Glu Glu Thr Asn Leu Ile Leu Arg Lys Leu Thr Ser
            525                 530                 535

GGA TCG GCA GAT CTA GAT GTC ATT TCG ATC ACT GGT ATG CCG GGT TCA        1743
Gly Ser Ala Asp Leu Asp Val Ile Ser Ile Thr Gly Met Pro Gly Ser
        540                 545                 550

GGT AAA ACT ACT TTG GCA TAC AAA GTA TAC AAT GAT AAG TCA GTT TCT        1791
Gly Lys Thr Thr Leu Ala Tyr Lys Val Tyr Asn Asp Lys Ser Val Ser
555                 560                 565

AGC CGT TTC GAC CTT CGT GCA TGG TGC ACG GTC GAC CAA GGA TGT GAT        1839
Ser Arg Phe Asp Leu Arg Ala Trp Cys Thr Val Asp Gln Gly Cys Asp
570                 575                 580                 585

GAG AAG AAG TTG TTG AAT ACA ATT TTC AGT CAA GTT AGT GAC TCA GAT        1887
Glu Lys Lys Leu Leu Asn Thr Ile Phe Ser Gln Val Ser Asp Ser Asp
                590                 595                 600

TCA AAA TTG AGT GAG AAT ATT GAT GTT GCT GAT AAA TTA CGG AAA CAA        1935
Ser Lys Leu Ser Glu Asn Ile Asp Val Ala Asp Lys Leu Arg Lys Gln
            605                 610                 615
```

-continued

| | |
|---|---|
| CTG TTT GGA AAG AGG TAT CTT ATT GTC TTA GAT GAC GTG TGG GAT ACT<br>Leu Phe Gly Lys Arg Tyr Leu Ile Val Leu Asp Asp Val Trp Asp Thr<br>620                    625                      630 | 1983 |
| ACT ACA TGG GAT GAG TTA ACA AGA CCT TTT CCT GAA TCT AAG AAA GGA<br>Thr Thr Trp Asp Glu Leu Thr Arg Pro Phe Pro Glu Ser Lys Lys Gly<br>     635                   640                   645 | 2031 |
| AGT AGG ATT ATT TTG ACA ACT CGG GAA AAG GAA GTG GCT TTG CAT GGA<br>Ser Arg Ile Ile Leu Thr Thr Arg Glu Lys Glu Val Ala Leu His Gly<br>650                    655                      660                   665 | 2079 |
| AAG CTG AAC ACT GAT CCT CTT GAC CTT CGA TTG CTA AGA CCA GAT GAA<br>Lys Leu Asn Thr Asp Pro Leu Asp Leu Arg Leu Leu Arg Pro Asp Glu<br>               670                    675                   680 | 2127 |
| AGT TGG GAA CTA TTA GAG AAA AGG GCA TTT GGG AAT GAG AGT TGC CCT<br>Ser Trp Glu Leu Leu Glu Lys Arg Ala Phe Gly Asn Glu Ser Cys Pro<br>                    685                   690                      695 | 2175 |
| GAT GAA CTA TTA GAT GTC GGT AAA GAA ATA GCC GAA AAT TGT AAA GGG<br>Asp Glu Leu Leu Asp Val Gly Lys Glu Ile Ala Glu Asn Cys Lys Gly<br>700                    705                      710 | 2223 |
| CTT CCT TTG GTG GCT GAT CTG ATT GCT GGA GTC ATT GCT GGG AGG GAA<br>Leu Pro Leu Val Ala Asp Leu Ile Ala Gly Val Ile Ala Gly Arg Glu<br>     715                   720                   725 | 2271 |
| AAG AAA AGG AGT GTG TGG CTT GAA GTT CAA AGT AGT TTG AGT TCT TTT<br>Lys Lys Arg Ser Val Trp Leu Glu Val Gln Ser Ser Leu Ser Ser Phe<br>730                    735                      740                   745 | 2319 |
| ATT TTG AAC AGT GAA GTG GAA GTG ATG AAA GTT ATA GAA TTA AGT TAT<br>Ile Leu Asn Ser Glu Val Glu Val Met Lys Val Ile Glu Leu Ser Tyr<br>               750                    755                   760 | 2367 |
| GAC CAT TTA CCA CAT CAC CTC AAG CCA TGC TTG CTG TAT TTT GCA AGT<br>Asp His Leu Pro His His Leu Lys Pro Cys Leu Leu Tyr Phe Ala Ser<br>765                    770                      775 | 2415 |
| TTT CCG AAG GAC ACT TCA TTG ACA ATC TAT GAG TTG AAT GTT TAT TTC<br>Phe Pro Lys Asp Thr Ser Leu Thr Ile Tyr Glu Leu Asn Val Tyr Phe<br>     780                   785                      790 | 2463 |
| GGT GCT GAA GGA TTT GTG GGA AAG ACG GAG ATG AAC AGT ATG GAA GAA<br>Gly Ala Glu Gly Phe Val Gly Lys Thr Glu Met Asn Ser Met Glu Glu<br>795                    800                      805 | 2511 |
| GTG GTG AAG ATT TAT ATG GAT GAT TTA ATT TAC AGT AGC TTG GTA ATT<br>Val Val Lys Ile Tyr Met Asp Asp Leu Ile Tyr Ser Ser Leu Val Ile<br>810                    815                    820                   825 | 2559 |
| TGT TTC AAT GAG ATA GGT TAT GCA CTG AAT TTC CAA ATT CAT GAT CTT<br>Cys Phe Asn Glu Ile Gly Tyr Ala Leu Asn Phe Gln Ile His Asp Leu<br>               830                    835                   840 | 2607 |
| GTG CAT GAC TTT TGT TTG ATA AAA GCA AGA AAG GAA AAT TTG TTT GAT<br>Val His Asp Phe Cys Leu Ile Lys Ala Arg Lys Glu Asn Leu Phe Asp<br>                    845                   850                   855 | 2655 |
| CAG ATA AGA TCA AGT GCT CCA TCA GAT TTG TTG CCT CGT CAA ATT ACC<br>Gln Ile Arg Ser Ser Ala Pro Ser Asp Leu Leu Pro Arg Gln Ile Thr<br>               860                    865                   870 | 2703 |
| ATT GAT TGT GAT GAG GAG GAG CAC TTT GGG CTT AAT TTT GTC ATG TTC<br>Ile Asp Cys Asp Glu Glu Glu His Phe Gly Leu Asn Phe Val Met Phe<br>875                    880                      885 | 2751 |
| GAT TCA AAT AAG AAA AGG CAT TCT GGT AAA CAC CTC TAT TCT TTG AGG<br>Asp Ser Asn Lys Lys Arg His Ser Gly Lys His Leu Tyr Ser Leu Arg<br>890                    895                      900                   905 | 2799 |
| ATA ATT GGA GAC CAG CTG GAT GAC AGT GTT TCT GAT GCA TTT CAC CTA<br>Ile Ile Gly Asp Gln Leu Asp Asp Ser Val Ser Asp Ala Phe His Leu<br>               910                    915                   920 | 2847 |
| AGA CAC TTG AGG CTT CTT AGA GTG TTG GAC CTG CAT ACG TCT TTT ATC<br>Arg His Leu Arg Leu Leu Arg Val Leu Asp Leu His Thr Ser Phe Ile<br>                    925                   930                   935 | 2895 |

```
                                                      -continued

ATG GTG AAA GAT TCT TTG CTG AAT GAA ATA TGC ATG TTG AAT CAT TTG          2943
Met Val Lys Asp Ser Leu Leu Asn Glu Ile Cys Met Leu Asn His Leu
        940                 945                 950

AGG TAC TTA TCC ATT GAC ACA CAA GTT AAA TAT CTG CCT TTG TCT TTC          2991
Arg Tyr Leu Ser Ile Asp Thr Gln Val Lys Tyr Leu Pro Leu Ser Phe
955                 960                 965

TCA AAC CTC TGG AAT CTA GAA AGC CTG TTT GTG TCT ACC AAC AGA TCA          3039
Ser Asn Leu Trp Asn Leu Glu Ser Leu Phe Val Ser Thr Asn Arg Ser
970                 975                 980                 985

ATC TTG GTA CTA TTA CCG AGA ATT TTG GAT CTT GTA AAG TTG CGA GTG          3087
Ile Leu Val Leu Leu Pro Arg Ile Leu Asp Leu Val Lys Leu Arg Val
                990                 995                 1000

CTG TCC GTG GAT GCT TGT TCT TTC TTT GAT ATG GAT GCA GAT GAA TCA          3135
Leu Ser Val Asp Ala Cys Ser Phe Phe Asp Met Asp Ala Asp Glu Ser
            1005                1010                1015

ATA TTG ATA GCA GAG GAC ACA AAG TTA GAG AAC TTG AGA ATA TTA ACG          3183
Ile Leu Ile Ala Glu Asp Thr Lys Leu Glu Asn Leu Arg Ile Leu Thr
        1020                1025                1030

GAA CTG TTG ATT TCC TAT TCG AAA GAT ACA AAG AAT ATT TTC AAA AGG          3231
Glu Leu Leu Ile Ser Tyr Ser Lys Asp Thr Lys Asn Ile Phe Lys Arg
    1035                1040                1045

TTT CCC AAT CTT CAG TTG CTT TCA TTT GAA CTC AAG GAG TCA TGG GAT          3279
Phe Pro Asn Leu Gln Leu Leu Ser Phe Glu Leu Lys Glu Ser Trp Asp
1050                1055                1060                1065

TAT TCA ACA GAG CAA CAT TGG TTC TCG GAA TTG GAT TTC CTA ACT GAA          3327
Tyr Ser Thr Glu Gln His Trp Phe Ser Glu Leu Asp Phe Leu Thr Glu
                1070                1075                1080

CTA GAA ACA CTC TCT GTA GGT TTT AAA AGT TCA AAC ACA AAC GAT AGT          3375
Leu Glu Thr Leu Ser Val Gly Phe Lys Ser Ser Asn Thr Asn Asp Ser
            1085                1090                1095

GGG TCC TCT GTA GCG ACA AAT CGG CCG TGG GAT TTT CAC TTC CCT TCA          3423
Gly Ser Ser Val Ala Thr Asn Arg Pro Trp Asp Phe His Phe Pro Ser
        1100                1105                1110

AAT TTG AAA ATA CTG TGG TTG CGT GAA TTT CCG CTG ACA TCC GAT TCA          3471
Asn Leu Lys Ile Leu Trp Leu Arg Glu Phe Pro Leu Thr Ser Asp Ser
    1115                1120                1125

CTA TCA ACA ATA GCG AGA CTG CCC AAC CTT GAA GAG TTG TCC CTT TAT          3519
Leu Ser Thr Ile Ala Arg Leu Pro Asn Leu Glu Glu Leu Ser Leu Tyr
1130                1135                1140                1145

CAT ACA ATC ATC CAT GGA GAA GAA TGG AAC ATG GGG GAG GAA GAC ACC          3567
His Thr Ile Ile His Gly Glu Glu Trp Asn Met Gly Glu Glu Asp Thr
                1150                1155                1160

TTT GAG AAT CTC AAA TTT TTG AAC TTC AAT CAA GTT AGT ATT TCC AAG          3615
Phe Glu Asn Leu Lys Phe Leu Asn Phe Asn Gln Val Ser Ile Ser Lys
            1165                1170                1175

TGG GAG GTT GGA GAG GAA TCC TTC CCC AAT CTT GAG AAA TTA AAA CTG          3663
Trp Glu Val Gly Glu Glu Ser Phe Pro Asn Leu Glu Lys Leu Lys Leu
        1180                1185                1190

CGG GGA TGT CAT AAG CTA GAG GAG ATT CCA CCT AGT TTT GGA GAT ATT          3711
Arg Gly Cys His Lys Leu Glu Glu Ile Pro Pro Ser Phe Gly Asp Ile
    1195                1200                1205

TAT TCA TTG AAA TCT ATC AAA ATT GTA AAG AGT CCT CAA CTT GAA GAT          3759
Tyr Ser Leu Lys Ser Ile Lys Ile Val Lys Ser Pro Gln Leu Glu Asp
1210                1215                1220                1225

TCT GCT CTC AAA ATT AAG GAA TAC GCT GAA GAT ATG AGG GGA GGG GAC          3807
Ser Ala Leu Lys Ile Lys Glu Tyr Ala Glu Asp Met Arg Gly Gly Asp
                1230                1235                1240

GAG CTT CAG ATC CTT GGC CAA AAG AAT ATC CCC TTA TTT AAG                  3849
Glu Leu Gln Ile Leu Gly Gln Lys Asn Ile Pro Leu Phe Lys
```

```
                    1245            1250            1255
TAGCATTATG GTTGAAAAGT AGATTGTACT TTGCTGGGTA GATTGTATAT GATTAAGAAA      3909

ATTTTGTTGC AGTTATGAAA TATTTTTGTG GATTTCTCAA AGTTTCTGCA ACAAAAATTA      3969

TAATTTTTAT AAAAAAAAAA AAAAAAA                                         3997

(2) INFORMATION FOR SEQ ID NO:3:

(i) SEQUENCE CHARACTERISTICS:
        (A) LENGTH: 1255 amino acids
        (B) TYPE: amino acid
        (D) TOPOLOGY: linear (ii) MOLECULE TYPE: protein (xi) SEQUENCE DESCRIPTION: SEQ ID NO:3:

Met Glu Lys Arg Lys Asp Asn Glu Glu Ala Asn Asn Ser Leu Val Leu
 1               5                  10                  15

Phe Ser Ala Leu Ser Lys Asp Ile Ala Asp Val Leu Val Phe Leu Glu
                20                  25                  30

Asn Glu Glu Asn Gln Lys Ala Leu Asp Lys Asp Gln Val Glu Lys Ile
            35                  40                  45

Lys Leu Lys Met Ala Phe Ile Cys Thr Tyr Val Gln Leu Ser Cys Ser
 50                  55                  60

Asp Phe Glu Gln Phe Glu Asp Ile Met Thr Arg Lys Arg Gln Glu Val
 65                  70                  75                  80

Glu Asn Leu Leu Gln Pro Leu Asp Asp Asp Val Phe Thr Ser Leu
                85                  90                  95

Thr Ser Asn Met Asp Asp Cys Ile Ser Leu Tyr His Arg Ser Tyr Lys
                100                 105                 110

Ser Asp Ala Ile Met Met Asp Glu Gln Leu Asp Phe Leu Leu Leu Asn
            115                 120                 125

Leu Tyr His Leu Ser Lys His His Ala Glu Lys Ile Phe Pro Gly Val
130                 135                 140

Thr Gln Tyr Glu Val Leu Gln Asn Ile Cys Gly Asn Ile Arg Asp Phe
145                 150                 155                 160

His Gly Leu Ile Val Asn Gly Cys Ile Lys His Glu Met Val Glu Asn
                165                 170                 175

Val Leu Pro Leu Phe Gln Leu Met Ala Asp Arg Val Gly His Phe Leu
                180                 185                 190

Trp Asp Gln Thr Asp Glu Asp Ser Arg Leu Ser Glu Leu Asp Glu
            195                 200                 205

Asp Glu Gln Asn Asp Arg Asp Ser Arg Leu Phe Lys Leu Ala His Leu
210                 215                 220

Leu Leu Lys Ile Val Pro Val Glu Leu Glu Val Ile His Ile Cys Tyr
225                 230                 235                 240

Thr Asn Leu Lys Ala Ser Thr Ser Ala Glu Val Gly Leu Phe Ile Lys
                245                 250                 255

Gln Leu Leu Glu Thr Ser Pro Asp Ile Leu Arg Glu Tyr Leu Ile Pro
            260                 265                 270

Leu Gln Glu His Met Val Thr Val Ile Thr Pro Ser Thr Ser Gly Ala
            275                 280                 285

Arg Asn Ile His Val Met Met Glu Phe Leu Leu Ile Leu Ser Asp
            290                 295                 300

Met Pro Lys Asp Phe Ile His His Asp Lys Leu Phe Asp Leu Leu Asp
305                 310                 315                 320
```

-continued

```
Arg Val Gly Val Leu Thr Arg Glu Val Ser Thr Leu Val Arg Asp Leu
                325                 330                 335

Glu Glu Glu Pro Arg Asn Lys Glu Gly Asn Asn Gln Thr Asn Cys Ala
            340                 345                 350

Thr Leu Asp Leu Leu Glu Asn Ile Glu Leu Leu Lys Lys Asp Leu Lys
        355                 360                 365

His Val Tyr Leu Lys Ala Leu Asp Ser Ser Gln Cys Cys Phe Pro Met
    370                 375                 380

Ser Asp Gly Pro Leu Phe Met His Leu Leu His Ile His Leu Asn Asp
385                 390                 395                 400

Leu Leu Asp Ser Asn Ala Tyr Ser Ile Ala Leu Ile Lys Glu Glu Ile
                405                 410                 415

Glu Leu Val Lys Gln Asp Leu Lys Phe Ile Arg Ser Phe Phe Val Asp
            420                 425                 430

Ala Glu Gln Gly Leu Tyr Lys Asp Leu Trp Ala Arg Val Leu Asp Val
        435                 440                 445

Ala Tyr Glu Ala Lys Asp Val Ile Asp Ser Ile Ile Val Arg Asp Asn
    450                 455                 460

Gly Leu Leu His Leu Ile Phe Ser Leu Pro Ile Thr Ile Lys Lys Ile
465                 470                 475                 480

Lys Leu Ile Lys Glu Glu Ile Ser Ala Leu Asp Glu Asn Ile Pro Lys
                485                 490                 495

Asp Arg Gly Leu Ile Val Val Asn Ser Pro Lys Lys Pro Val Glu Arg
            500                 505                 510

Lys Ser Leu Thr Thr Asp Lys Ile Thr Val Gly Phe Glu Glu Glu Thr
        515                 520                 525

Asn Leu Ile Leu Arg Lys Leu Thr Ser Gly Ser Ala Asp Leu Asp Val
    530                 535                 540

Ile Ser Ile Thr Gly Met Pro Gly Ser Gly Lys Thr Thr Leu Ala Tyr
545                 550                 555                 560

Lys Val Tyr Asn Asp Lys Ser Val Ser Ser Arg Phe Asp Leu Arg Ala
                565                 570                 575

Trp Cys Thr Val Asp Gln Gly Cys Asp Glu Lys Lys Leu Leu Asn Thr
            580                 585                 590

Ile Phe Ser Gln Val Ser Asp Ser Asp Ser Lys Leu Ser Glu Asn Ile
        595                 600                 605

Asp Val Ala Asp Lys Leu Arg Lys Gln Leu Phe Gly Lys Arg Tyr Leu
    610                 615                 620

Ile Val Leu Asp Asp Val Trp Asp Thr Thr Thr Trp Asp Glu Leu Thr
625                 630                 635                 640

Arg Pro Phe Pro Glu Ser Lys Lys Gly Ser Arg Ile Ile Leu Thr Thr
                645                 650                 655

Arg Glu Lys Glu Val Ala Leu His Gly Lys Leu Asn Thr Asp Pro Leu
            660                 665                 670

Asp Leu Arg Leu Leu Arg Pro Asp Glu Ser Trp Glu Leu Leu Glu Lys
        675                 680                 685

Arg Ala Phe Gly Asn Glu Ser Cys Pro Asp Glu Leu Leu Asp Val Gly
    690                 695                 700

Lys Glu Ile Ala Glu Asn Cys Lys Gly Leu Pro Leu Val Ala Asp Leu
705                 710                 715                 720

Ile Ala Gly Val Ile Ala Gly Arg Glu Lys Arg Ser Val Trp Leu
                725                 730                 735
```

-continued

```
Glu Val Gln Ser Ser Leu Ser Ser Phe Ile Leu Asn Ser Glu Val Glu
            740                 745                 750
Val Met Lys Val Ile Glu Leu Ser Tyr Asp His Leu Pro His His Leu
        755                 760                 765
Lys Pro Cys Leu Leu Tyr Phe Ala Ser Phe Pro Lys Asp Thr Ser Leu
    770                 775                 780
Thr Ile Tyr Glu Leu Asn Val Tyr Phe Gly Ala Glu Gly Phe Val Gly
785                 790                 795                 800
Lys Thr Glu Met Asn Ser Met Glu Val Val Lys Ile Tyr Met Asp
            805                 810                 815
Asp Leu Ile Tyr Ser Ser Leu Val Ile Cys Phe Asn Glu Ile Gly Tyr
            820                 825                 830
Ala Leu Asn Phe Gln Ile His Asp Leu Val His Asp Phe Cys Leu Ile
        835                 840                 845
Lys Ala Arg Lys Glu Asn Leu Phe Asp Gln Ile Arg Ser Ser Ala Pro
    850                 855                 860
Ser Asp Leu Leu Pro Arg Gln Ile Thr Ile Asp Cys Asp Glu Glu Glu
865                 870                 875                 880
His Phe Gly Leu Asn Phe Val Met Phe Asp Ser Asn Lys Lys Arg His
            885                 890                 895
Ser Gly Lys His Leu Tyr Ser Leu Arg Ile Ile Gly Asp Gln Leu Asp
            900                 905                 910
Asp Ser Val Ser Asp Ala Phe His Leu Arg His Leu Arg Leu Leu Arg
        915                 920                 925
Val Leu Asp Leu His Thr Ser Phe Ile Met Val Lys Asp Ser Leu Leu
    930                 935                 940
Asn Glu Ile Cys Met Leu Asn His Leu Arg Tyr Leu Ser Ile Asp Thr
945                 950                 955                 960
Gln Val Lys Tyr Leu Pro Leu Ser Phe Ser Asn Leu Trp Asn Leu Glu
            965                 970                 975
Ser Leu Phe Val Ser Thr Asn Arg Ser Ile Leu Val Leu Leu Pro Arg
            980                 985                 990
Ile Leu Asp Leu Val Lys Leu Arg Val Leu Ser Val Asp Ala Cys Ser
        995                 1000                1005
Phe Phe Asp Met Asp Ala Asp Glu Ser Ile Leu Ile Ala Glu Asp Thr
    1010                1015                1020
Lys Leu Glu Asn Leu Arg Ile Leu Thr Glu Leu Leu Ile Ser Tyr Ser
1025                1030                1035                1040
Lys Asp Thr Lys Asn Ile Phe Lys Arg Phe Pro Asn Leu Gln Leu Leu
            1045                1050                1055
Ser Phe Glu Leu Lys Glu Ser Trp Asp Tyr Ser Thr Glu Gln His Trp
            1060                1065                1070
Phe Ser Glu Leu Asp Phe Leu Thr Glu Leu Glu Thr Leu Ser Val Gly
        1075                1080                1085
Phe Lys Ser Ser Asn Thr Asn Asp Ser Gly Ser Ser Val Ala Thr Asn
    1090                1095                1100
Arg Pro Trp Asp Phe His Phe Pro Ser Asn Leu Lys Ile Leu Trp Leu
1105                1110                1115                1120
Arg Glu Phe Pro Leu Thr Ser Asp Ser Leu Ser Thr Ile Ala Arg Leu
            1125                1130                1135
Pro Asn Leu Glu Glu Leu Ser Leu Tyr His Thr Ile Ile His Gly Glu
            1140                1145                1150
Glu Trp Asn Met Gly Glu Glu Asp Thr Phe Glu Asn Leu Lys Phe Leu
```

-continued

```
            1155                1160                1165
Asn Phe Asn Gln Val Ser Ile Ser Lys Trp Glu Val Gly Glu Glu Ser
    1170                1175                1180

Phe Pro Asn Leu Glu Lys Leu Lys Leu Arg Gly Cys His Lys Leu Glu
1185                1190                1195                1200

Glu Ile Pro Pro Ser Phe Gly Asp Ile Tyr Ser Leu Lys Ser Ile Lys
            1205                1210                1215

Ile Val Lys Ser Pro Gln Leu Glu Asp Ser Ala Leu Lys Ile Lys Glu
            1220                1225                1230

Tyr Ala Glu Asp Met Arg Gly Gly Asp Glu Leu Gln Ile Leu Gly Gln
            1235                1240                1245

Lys Asn Ile Pro Leu Phe Lys
            1250                1255
```

(2) INFORMATION FOR SEQ ID NO:4:

(i) SEQUENCE CHARACTERISTICS:
        (A) LENGTH: 3982 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 87..3860
        (D) OTHER INFORMATION: /note= "Copy 2 cDNA for M1 nematode
            resistance gene of tomato"

(xi) SEQUENCE DESCRIPTION: SEQ ID NO:4:

```
TCCAATAGCT TCAACATTAT TTCTCAAACA AAGGGTTCTC TAGCTAAACT TCAGCCAGTG        60

TAAAGGTCTT GAGAAAAAGT AGAATC ATG GAA AAA CGA AAA GAT ATT GAA GAA       113
                            Met Glu Lys Arg Lys Asp Ile Glu Glu
                              1               5

GCA AAC AAC TCA TTG GTG TTA TTT TCT GCT CTT AGC AAG GAC ATT GCC       161
Ala Asn Asn Ser Leu Val Leu Phe Ser Ala Leu Ser Lys Asp Ile Ala
 10              15                  20                  25

AAT GTT CTA ATT TTC CTA GAG AAT GAG GAA AAT CAA AAA GCT CTT GAC       209
Asn Val Leu Ile Phe Leu Glu Asn Glu Glu Asn Gln Lys Ala Leu Asp
             30                  35                  40

AAA GAT CAA GTT GAA AAG CTA AAA TTG AAA ATG GCA TTT ATT TGT ACA       257
Lys Asp Gln Val Glu Lys Leu Lys Leu Lys Met Ala Phe Ile Cys Thr
         45                  50                  55

TAT GTT CAG CTT TCT TAT TCC GAT TTT GAG CAG TTT GAA GAT ATA ATG       305
Tyr Val Gln Leu Ser Tyr Ser Asp Phe Glu Gln Phe Glu Asp Ile Met
     60                  65                  70

ACT AGA AAT AGA CAA GAG GTT GAG AAT CTG CTT CAA TCA CTT TTG GAT       353
Thr Arg Asn Arg Gln Glu Val Glu Asn Leu Leu Gln Ser Leu Leu Asp
 75                  80                  85

GAT GAT GTC CTT ACT AGC CTC ACC AGT AAT ATG GAT GAC TGT ATC AGC       401
Asp Asp Val Leu Thr Ser Leu Thr Ser Asn Met Asp Asp Cys Ile Ser
 90                  95                 100                 105

TTG TAT CAT CGT TCT TAT AAA TCA GAT GCC ATC ATG ATG GAT GAG CAA       449
Leu Tyr His Arg Ser Tyr Lys Ser Asp Ala Ile Met Met Asp Glu Gln
            110                 115                 120

TTG GAC TTC CTC CTC TTG AAT CTG TAT CAT CTA TCC AAG CAT CAC GCT       497
Leu Asp Phe Leu Leu Leu Asn Leu Tyr His Leu Ser Lys His His Ala
        125                 130                 135

GAA AAG ATA TTT CCT GGA GTG ACT CAA TAT GAA GTT CTT CAG AAT GTA       545
Glu Lys Ile Phe Pro Gly Val Thr Gln Tyr Glu Val Leu Gln Asn Val
```

```
                  140                 145                 150
TGT GGC AAC ATA AGA GAT TTC CAT GGG TTG ATA CTG AAT GGT TGC ATT      593
Cys Gly Asn Ile Arg Asp Phe His Gly Leu Ile Leu Asn Gly Cys Ile
155                 160                 165

AAG CAT GAG ATG GTT GAG AAT GTC TTA CCT CTG TTT CAA CTC ATG GCT      641
Lys His Glu Met Val Glu Asn Val Leu Pro Leu Phe Gln Leu Met Ala
170                 175                 180                 185

GAA AGA GTA GGA CAC TTC CTT TGG GAG GAT CAG ACT GAT GAA GAC TCT      689
Glu Arg Val Gly His Phe Leu Trp Glu Asp Gln Thr Asp Glu Asp Ser
            190                 195                 200

CGG CTC TCC GAG CTA GAT GAG GAT GAA CAC AAT GAT AGA GAC TCT CGA      737
Arg Leu Ser Glu Leu Asp Glu Asp Glu His Asn Asp Arg Asp Ser Arg
                205                 210                 215

CTC TTC CAG CTA ACA CAT CTA CTC TTG AAG ATT GTT CCA ACT GAA CTG      785
Leu Phe Gln Leu Thr His Leu Leu Leu Lys Ile Val Pro Thr Glu Leu
            220                 225                 230

GAG GTT ATG CAC ATA TGT TAT ACA AAT TTG AAA GCT TCA ACT TCA GCA      833
Glu Val Met His Ile Cys Tyr Thr Asn Leu Lys Ala Ser Thr Ser Ala
235                 240                 245

GAA GTT GGA CGC TTC ATT AAG AAG CTC CTG GAA ACC TCA CCG GAT ATT      881
Glu Val Gly Arg Phe Ile Lys Lys Leu Leu Glu Thr Ser Pro Asp Ile
250                 255                 260                 265

CTC AGA GAA TAT ATC ATT CAA CTA CAA GAG CAT ATG TTA ACT GTT ATT      929
Leu Arg Glu Tyr Ile Ile Gln Leu Gln Glu His Met Leu Thr Val Ile
            270                 275                 280

CCC CCT AGC ACT TTA GGG GCT CGA AAC ATT CAT GTC ATG ATG GAA TTC      977
Pro Pro Ser Thr Leu Gly Ala Arg Asn Ile His Val Met Met Glu Phe
                285                 290                 295

CTA TTA CTT ATT CTT TCT GAT ATG CCC AAG GAC TTT ATT CAT CAT GAC     1025
Leu Leu Leu Ile Leu Ser Asp Met Pro Lys Asp Phe Ile His His Asp
            300                 305                 310

AAA CTT TTT GAT CTC TTG GCT CAT GTT GGA ACA CTT ACC AGG GAG GTA     1073
Lys Leu Phe Asp Leu Leu Ala His Val Gly Thr Leu Thr Arg Glu Val
315                 320                 325

TCG ACT CTT GTA CGT GAC TTG GAA GAG AAA TTA AGG AAT AAA GAG GGT     1121
Ser Thr Leu Val Arg Asp Leu Glu Glu Lys Leu Arg Asn Lys Glu Gly
330                 335                 340                 345

AAT AAC CAA ACA AAT TGT GCA ACC CTA GAC TTG CTG GAA AAT ATT GAA     1169
Asn Asn Gln Thr Asn Cys Ala Thr Leu Asp Leu Leu Glu Asn Ile Glu
            350                 355                 360

CTC CTC AAG AAA GAT CTC AAA CAT GTT TAT CTG AAA GCC CCA AAT TCA     1217
Leu Leu Lys Lys Asp Leu Lys His Val Tyr Leu Lys Ala Pro Asn Ser
                365                 370                 375

TCT CAA TGT TGC TTC CCC ATG AGT GAT GGA CCA CTC TTC ATG CAT CTT     1265
Ser Gln Cys Cys Phe Pro Met Ser Asp Gly Pro Leu Phe Met His Leu
            380                 385                 390

CTA CAC ATG CAC TTA AAT GAT TTG CTA GAT TCT AAT GCT TAT TCA ATT     1313
Leu His Met His Leu Asn Asp Leu Leu Asp Ser Asn Ala Tyr Ser Ile
395                 400                 405

TCT TTG ATA AAG GAA GAA ATC GAG TTG GTG AGT CAA GAA CTG GAA TTC     1361
Ser Leu Ile Lys Glu Glu Ile Glu Leu Val Ser Gln Glu Leu Glu Phe
410                 415                 420                 425

ATA AGA TCA TTC TTT GGG GAT GCT GCT GAG CAA GGA TTG TAT AAA GAT     1409
Ile Arg Ser Phe Phe Gly Asp Ala Ala Glu Gln Gly Leu Tyr Lys Asp
            430                 435                 440

ATC TGG GCA CGT GTT CTA GAT GTG GCT TAT GAG GCA AAA GAT GTC ATA     1457
Ile Trp Ala Arg Val Leu Asp Val Ala Tyr Glu Ala Lys Asp Val Ile
                445                 450                 455

GAT TCA ATT ATT GTT CGA GAT AAT GGT CTC TTA CAT CTT ATT TTC TCA     1505
```

```
                Asp Ser Ile Ile Val Arg Asp Asn Gly Leu Leu His Leu Ile Phe Ser
                    460                 465                 470

CTT CCC ATT ACC ATA AAG AAG ATC AAA CTT ATC AAA GAA GAG ATC TCT              1553
Leu Pro Ile Thr Ile Lys Lys Ile Lys Leu Ile Lys Glu Glu Ile Ser
    475                 480                 485

GCT TTA GAT GAG AAC ATT CCC AAG GAC AGA GGT CTA ATC GTT GTG AAC              1601
Ala Leu Asp Glu Asn Ile Pro Lys Asp Arg Gly Leu Ile Val Val Asn
490                 495                 500                 505

TCT CCC AAG AAA CCA GTT GAG AGA AAG TCA TTG ACA ACT GAT AAA ATA              1649
Ser Pro Lys Lys Pro Val Glu Arg Lys Ser Leu Thr Thr Asp Lys Ile
                510                 515                 520

ATT GTA GGT TTT GAG GAG GAG ACA AAC TTG ATA CTT AGA AAG CTC ACC              1697
Ile Val Gly Phe Glu Glu Glu Thr Asn Leu Ile Leu Arg Lys Leu Thr
            525                 530                 535

AGT GGA CCC GCA GAT TTA GAT GTC ATT TCG ATC ACC GGT ATG CCG GGT              1745
Ser Gly Pro Ala Asp Leu Asp Val Ile Ser Ile Thr Gly Met Pro Gly
        540                 545                 550

TCA GGT AAA ACT ACT TTG GCA TAC AAA GTA TAC AAT GAT AAG TCA GTT              1793
Ser Gly Lys Thr Thr Leu Ala Tyr Lys Val Tyr Asn Asp Lys Ser Val
    555                 560                 565

TCT AGA CAT TTT GAC CTT CGT GCA TGG TGC ACG GTC GAT CAA GGA TAT              1841
Ser Arg His Phe Asp Leu Arg Ala Trp Cys Thr Val Asp Gln Gly Tyr
570                 575                 580                 585

GAC GAC AAG AAG TTG TTG GAT ACA ATT TTC AGT CAA GTT AGT GGC TCA              1889
Asp Asp Lys Lys Leu Leu Asp Thr Ile Phe Ser Gln Val Ser Gly Ser
                590                 595                 600

GAT TCA AAT TTG AGT GAG AAT ATT GAT GTT GCT GAT AAA TTG CGG AAA              1937
Asp Ser Asn Leu Ser Glu Asn Ile Asp Val Ala Asp Lys Leu Arg Lys
            605                 610                 615

CAA CTG TTT GGA AAG AGG TAT CTT ATT GTC TTA GAT GAT GTG TGG GAT              1985
Gln Leu Phe Gly Lys Arg Tyr Leu Ile Val Leu Asp Asp Val Trp Asp
        620                 625                 630

ACT ACT ACA TTG GAT GAG TTG ACA AGA CCT TTT CCT GAA GCT AAG AAA              2033
Thr Thr Thr Leu Asp Glu Leu Thr Arg Pro Phe Pro Glu Ala Lys Lys
    635                 640                 645

GGA AGT AGG ATT ATT TTG ACA ACT CGA GAA AAG GAA GTG GCT TTG CAT              2081
Gly Ser Arg Ile Ile Leu Thr Thr Arg Glu Lys Glu Val Ala Leu His
650                 655                 660                 665

GGA AAG CTG AAC ACT GAT CCT CTT GAC CTT CGA TTG CTA AGA CCA GAT              2129
Gly Lys Leu Asn Thr Asp Pro Leu Asp Leu Arg Leu Leu Arg Pro Asp
                670                 675                 680

GAA AGT TGG GAA CTT TTA GAT AAA AGG ACA TTT GGT AAT GAG AGT TGC              2177
Glu Ser Trp Glu Leu Leu Asp Lys Arg Thr Phe Gly Asn Glu Ser Cys
            685                 690                 695

CCT GAT GAA CTA TTA GAT GTC GGT AAA GAA ATA GCC GAA AAT TGT AAA              2225
Pro Asp Glu Leu Leu Asp Val Gly Lys Glu Ile Ala Glu Asn Cys Lys
        700                 705                 710

GGG CTT CCT TTG GTG GCT GAT CTG ATT GCT GGA GTC ATT GCT GGG AGG              2273
Gly Leu Pro Leu Val Ala Asp Leu Ile Ala Gly Val Ile Ala Gly Arg
    715                 720                 725

GAA AAG AAA AGG AGT GTG TGG CTT GAA GTT CAA AGT AGT TTG AGT TCT              2321
Glu Lys Lys Arg Ser Val Trp Leu Glu Val Gln Ser Ser Leu Ser Ser
730                 735                 740                 745

TTT ATT TTG AAC AGT GAA GTG GAA GTG ATG AAA GTT ATA GAA TTA AGT              2369
Phe Ile Leu Asn Ser Glu Val Glu Val Met Lys Val Ile Glu Leu Ser
                750                 755                 760

TAT GAC CAT TTA CCA CAT CAC CTC AAG CCA TGC TTG CTT CAC TTT GCA              2417
Tyr Asp His Leu Pro His His Leu Lys Pro Cys Leu Leu His Phe Ala
            765                 770                 775
```

-continued

```
AGT TGG CCG AAG GAC ACT CCT TTG ACA ATC TAT TTG TTT ACT GTT TAT      2465
Ser Trp Pro Lys Asp Thr Pro Leu Thr Ile Tyr Leu Phe Thr Val Tyr
            780                 785                 790

TTG GGT GCT GAA GGA TTT GTG GAA AAG ACG GAG ATG AAG GGT ATA GAA      2513
Leu Gly Ala Glu Gly Phe Val Glu Lys Thr Glu Met Lys Gly Ile Glu
795                 800                 805

GAA GTG GTG AAG ATT TAT ATG GAT GAT TTA ATT TCC AGT AGC TTG GTA      2561
Glu Val Val Lys Ile Tyr Met Asp Asp Leu Ile Ser Ser Ser Leu Val
810                 815                 820                 825

ATT TGT TTC AAT GAG ATA GGT GAT ATA CTG AAT TTC CAA ATT CAT GAT      2609
Ile Cys Phe Asn Glu Ile Gly Asp Ile Leu Asn Phe Gln Ile His Asp
            830                 835                 840

CTT GTG CAT GAC TTT TGT TTG ATA AAA GCA AGA AAG GAA AAT TTG TTT      2657
Leu Val His Asp Phe Cys Leu Ile Lys Ala Arg Lys Glu Asn Leu Phe
            845                 850                 855

GAT CGG ATA AGA TCA AGT GCT CCA TCA GAT TTG TTG CCT CGT CAA ATT      2705
Asp Arg Ile Arg Ser Ser Ala Pro Ser Asp Leu Leu Pro Arg Gln Ile
            860                 865                 870

ACC ATT GAT TAT GAT GAG GAG GAG CAC TTT GGG CTT AAT TTT GTC          2753
Thr Ile Asp Tyr Asp Glu Glu Glu His Phe Gly Leu Asn Phe Val
875                 880                 885

ATG TTC GAT TCA AAT AAG AAA AGG CAT TCT GGT AAA CAC CTC TAT TCT      2801
Met Phe Asp Ser Asn Lys Lys Arg His Ser Gly Lys His Leu Tyr Ser
890                 895                 900                 905

TTG AGG ATA AAT GGA GAC CAG CTG GAT GAC AGT GTT TCT GAT GCA TTT      2849
Leu Arg Ile Asn Gly Asp Gln Leu Asp Asp Ser Val Ser Asp Ala Phe
            910                 915                 920

CAC CTA AGA CAC TTG AGG CTT ATT AGA GTG TTG GAC CTG GAA CCC TCT      2897
His Leu Arg His Leu Arg Leu Ile Arg Val Leu Asp Leu Glu Pro Ser
            925                 930                 935

TTA ATC ATG GTG AAT GAT TCT TTG CTG AAT GAA ATA TGC ATG TTG AAT      2945
Leu Ile Met Val Asn Asp Ser Leu Leu Asn Glu Ile Cys Met Leu Asn
            940                 945                 950

CAT TTG AGG TAC TTA AGA ATT CGG ACA CAA GTT AAA TAT CTG CCT TTC      2993
His Leu Arg Tyr Leu Arg Ile Arg Thr Gln Val Lys Tyr Leu Pro Phe
955                 960                 965

TCT TTC TCA AAC CTC TGG AAT CTA GAA AGT CTG TTT GTG TCT AAC AAA      3041
Ser Phe Ser Asn Leu Trp Asn Leu Glu Ser Leu Phe Val Ser Asn Lys
970                 975                 980                 985

GGA TCA ATC TTG GTA CTA TTA CCG AGA ATT TTG GAT CTT GTA AAG TTG      3089
Gly Ser Ile Leu Val Leu Leu Pro Arg Ile Leu Asp Leu Val Lys Leu
            990                 995                 1000

CGA GTG CTG TCC GTG GGT GCT TGT TCT TTC TTT GAT ATG GAT GCA GAT      3137
Arg Val Leu Ser Val Gly Ala Cys Ser Phe Phe Asp Met Asp Ala Asp
            1005                1010                1015

GAA TCA ATA TTG ATA GCA AAG GAC ACA AAG TTA GAG AAC TTG AGA ATA      3185
Glu Ser Ile Leu Ile Ala Lys Asp Thr Lys Leu Glu Asn Leu Arg Ile
            1020                1025                1030

TTA GGG GAA CTG TTG ATT TCC TAT TCG AAA GAT ACA ATG AAT ATT TTC      3233
Leu Gly Glu Leu Leu Ile Ser Tyr Ser Lys Asp Thr Met Asn Ile Phe
            1035                1040                1045

AAA AGG TTT CCC AAT CTT CAG GTG CTT CAG TTT GAA CTC AAG GAG TCA      3281
Lys Arg Phe Pro Asn Leu Gln Val Leu Gln Phe Glu Leu Lys Glu Ser
1050                1055                1060                1065

TGG GAT TAT TCA ACA GAG CAA CAT TGG TTC CCG AAA TTG GAT TGC CTA      3329
Trp Asp Tyr Ser Thr Glu Gln His Trp Phe Pro Lys Leu Asp Cys Leu
            1070                1075                1080

ACT GAA CTA GAA ACA CTC TGT GTA GGT TTT AAA AGT TCA AAC ACA AAC      3377
Thr Glu Leu Glu Thr Leu Cys Val Gly Phe Lys Ser Ser Asn Thr Asn
            1085                1090                1095
```

```
CAC TGT GGG TCC TCT GTT GTG ACA AAT CGG CCG TGG GAT TTT CAC TTC     3425
His Cys Gly Ser Ser Val Val Thr Asn Arg Pro Trp Asp Phe His Phe
            1100                1105                1110

CCT TCA AAT TTG AAA GAA CTG TTG TTG TAT GAC TTT CCT CTG ACA TCC     3473
Pro Ser Asn Leu Lys Glu Leu Leu Leu Tyr Asp Phe Pro Leu Thr Ser
        1115                1120                1125

GAT TCA CTA TCA ACA ATA GCG AGA CTG CCC AAC CTT GAA AAT TTG TCC     3521
Asp Ser Leu Ser Thr Ile Ala Arg Leu Pro Asn Leu Glu Asn Leu Ser
1130                1135                1140                1145

CTT TAT GAT ACA ATC ATC CAG GGA GAA GAA TGG AAC ATG GGG GAG GAA     3569
Leu Tyr Asp Thr Ile Ile Gln Gly Glu Glu Trp Asn Met Gly Glu Glu
                1150                1155                1160

GAC ACT TTT GAG AAT CTC AAA TTT TTG AAC TTG CGT CTA CTG ACT CTT     3617
Asp Thr Phe Glu Asn Leu Lys Phe Leu Asn Leu Arg Leu Leu Thr Leu
            1165                1170                1175

TCC AAG TGG GAG GTT GGA GAG GAA TCC TTC CCC AAT CTT GAG AAA TTA     3665
Ser Lys Trp Glu Val Gly Glu Glu Ser Phe Pro Asn Leu Glu Lys Leu
        1180                1185                1190

AAA CTG CAG GAA TGT GGT AAG CTT GAG GAG ATT CCA CCT AGT TTT GGA     3713
Lys Leu Gln Glu Cys Gly Lys Leu Glu Glu Ile Pro Pro Ser Phe Gly
1195                1200                1205

GAT ATT TAT TCA TTG AAA TTT ATC AAA ATT GTA AAG AGT CCT CAA CTT     3761
Asp Ile Tyr Ser Leu Lys Phe Ile Lys Ile Val Lys Ser Pro Gln Leu
1210                1215                1220                1225

GAA GAT TCT GCT CTC AAG ATT AAG AAA TAC GCT GAA GAT ATG AGA GGA     3809
Glu Asp Ser Ala Leu Lys Ile Lys Lys Tyr Ala Glu Asp Met Arg Gly
                1230                1235                1240

GGG AAC GAT CTT CAG ATC CTT GGC CAG AAG AAT ATC CCC TTA TTT AAG     3857
Gly Asn Asp Leu Gln Ile Leu Gly Gln Lys Asn Ile Pro Leu Phe Lys
            1245                1250                1255

TAGCATTTTG GTTGAACTTT GCTTGGTGAT ATTGTATATG ATTAAAATAT CCTGTGATGA   3917

GATTCCTCTT AGTTTCTTTT AACAAAAAAT ATAATTTTTA TAAGTACAAA AAAAAAAAA    3977

AAAAA                                                               3982

(2) INFORMATION FOR SEQ ID NO:5:

(i) SEQUENCE CHARACTERISTICS:
        (A) LENGTH: 1257 amino acids
        (B) TYPE: amino acid
        (D) TOPOLOGY: linear (ii) MOLECULE TYPE: protein (xi) SEQUENCE DESCRIPTION: SEQ ID NO:5:

Met Glu Lys Arg Lys Asp Ile Glu Glu Ala Asn Asn Ser Leu Val Leu
 1               5                  10                  15

Phe Ser Ala Leu Ser Lys Asp Ile Ala Asn Val Leu Ile Phe Leu Glu
            20                  25                  30

Asn Glu Glu Asn Gln Lys Ala Leu Asp Lys Asp Gln Val Glu Lys Leu
        35                  40                  45

Lys Leu Lys Met Ala Phe Ile Cys Thr Tyr Val Gln Leu Ser Tyr Ser
    50                  55                  60

Asp Phe Glu Gln Phe Glu Asp Ile Met Thr Arg Asn Arg Gln Glu Val
65                  70                  75                  80

Glu Asn Leu Leu Gln Ser Leu Leu Asp Asp Val Leu Thr Ser Leu
                85                  90                  95

Thr Ser Asn Met Asp Asp Cys Ile Ser Leu Tyr His Arg Ser Tyr Lys
            100                 105                 110
```

-continued

```
Ser Asp Ala Ile Met Met Asp Glu Gln Leu Asp Phe Leu Leu Leu Asn
        115                 120                 125
Leu Tyr His Leu Ser Lys His His Ala Glu Lys Ile Phe Pro Gly Val
        130                 135                 140
Thr Gln Tyr Glu Val Leu Gln Asn Val Cys Gly Asn Ile Arg Asp Phe
145                 150                 155                 160
His Gly Leu Ile Leu Asn Gly Cys Ile Lys His Glu Met Val Glu Asn
                165                 170                 175
Val Leu Pro Leu Phe Gln Leu Met Ala Glu Arg Val Gly His Phe Leu
                180                 185                 190
Trp Glu Asp Gln Thr Asp Glu Asp Ser Arg Leu Ser Glu Leu Asp Glu
                195                 200                 205
Asp Glu His Asn Asp Arg Asp Ser Arg Leu Phe Gln Leu Thr His Leu
        210                 215                 220
Leu Leu Lys Ile Val Pro Thr Glu Leu Glu Val Met His Ile Cys Tyr
225                 230                 235                 240
Thr Asn Leu Lys Ala Ser Thr Ser Ala Glu Val Gly Arg Phe Ile Lys
                245                 250                 255
Lys Leu Leu Glu Thr Ser Pro Asp Ile Leu Arg Glu Tyr Ile Ile Gln
                260                 265                 270
Leu Gln Glu His Met Leu Thr Val Ile Pro Pro Ser Thr Leu Gly Ala
        275                 280                 285
Arg Asn Ile His Val Met Met Glu Phe Leu Leu Leu Ile Leu Ser Asp
        290                 295                 300
Met Pro Lys Asp Phe Ile His His Asp Lys Leu Phe Asp Leu Leu Ala
305                 310                 315                 320
His Val Gly Thr Leu Thr Arg Glu Val Ser Thr Leu Val Arg Asp Leu
                325                 330                 335
Glu Glu Lys Leu Arg Asn Lys Glu Gly Asn Asn Gln Thr Asn Cys Ala
                340                 345                 350
Thr Leu Asp Leu Leu Glu Asn Ile Glu Leu Leu Lys Lys Asp Leu Lys
        355                 360                 365
His Val Tyr Leu Lys Ala Pro Asn Ser Ser Gln Cys Cys Phe Pro Met
        370                 375                 380
Ser Asp Gly Pro Leu Phe Met His Leu Leu His Met His Leu Asn Asp
385                 390                 395                 400
Leu Leu Asp Ser Asn Ala Tyr Ser Ile Ser Leu Ile Lys Glu Glu Ile
                405                 410                 415
Glu Leu Val Ser Gln Glu Leu Glu Phe Ile Arg Ser Phe Phe Gly Asp
                420                 425                 430
Ala Ala Glu Gln Gly Leu Tyr Lys Asp Ile Trp Ala Arg Val Leu Asp
        435                 440                 445
Val Ala Tyr Glu Ala Lys Asp Val Ile Asp Ser Ile Ile Val Arg Asp
        450                 455                 460
Asn Gly Leu Leu His Leu Ile Phe Ser Leu Pro Ile Thr Ile Lys Lys
465                 470                 475                 480
Ile Lys Leu Ile Lys Glu Glu Ile Ser Ala Leu Asp Glu Asn Ile Pro
                485                 490                 495
Lys Asp Arg Gly Leu Ile Val Val Asn Ser Pro Lys Lys Pro Val Glu
                500                 505                 510
Arg Lys Ser Leu Thr Thr Asp Lys Ile Ile Val Gly Phe Glu Glu Glu
        515                 520                 525
```

-continued

Thr Asn Leu Ile Leu Arg Lys Leu Thr Ser Gly Pro Ala Asp Leu Asp
    530                 535                 540

Val Ile Ser Ile Thr Gly Met Pro Gly Ser Gly Lys Thr Thr Leu Ala
545                 550                 555                 560

Tyr Lys Val Tyr Asn Asp Lys Ser Val Ser Arg His Phe Asp Leu Arg
                565                 570                 575

Ala Trp Cys Thr Val Asp Gln Gly Tyr Asp Asp Lys Lys Leu Leu Asp
            580                 585                 590

Thr Ile Phe Ser Gln Val Ser Gly Ser Asp Ser Asn Leu Ser Glu Asn
        595                 600                 605

Ile Asp Val Ala Asp Lys Leu Arg Lys Gln Leu Phe Gly Lys Arg Tyr
    610                 615                 620

Leu Ile Val Leu Asp Asp Val Trp Asp Thr Thr Thr Leu Asp Glu Leu
625                 630                 635                 640

Thr Arg Pro Phe Pro Glu Ala Lys Lys Gly Ser Arg Ile Ile Leu Thr
                645                 650                 655

Thr Arg Glu Lys Glu Val Ala Leu His Gly Lys Leu Asn Thr Asp Pro
            660                 665                 670

Leu Asp Leu Arg Leu Leu Arg Pro Asp Glu Ser Trp Glu Leu Leu Asp
        675                 680                 685

Lys Arg Thr Phe Gly Asn Glu Ser Cys Pro Asp Glu Leu Leu Asp Val
    690                 695                 700

Gly Lys Glu Ile Ala Glu Asn Cys Lys Gly Leu Pro Leu Val Ala Asp
705                 710                 715                 720

Leu Ile Ala Gly Val Ile Ala Gly Arg Glu Lys Lys Arg Ser Val Trp
                725                 730                 735

Leu Glu Val Gln Ser Ser Leu Ser Ser Phe Ile Leu Asn Ser Glu Val
            740                 745                 750

Glu Val Met Lys Val Ile Glu Leu Ser Tyr Asp His Leu Pro His His
        755                 760                 765

Leu Lys Pro Cys Leu Leu His Phe Ala Ser Trp Pro Lys Asp Thr Pro
    770                 775                 780

Leu Thr Ile Tyr Leu Phe Thr Val Tyr Leu Gly Ala Glu Gly Phe Val
785                 790                 795                 800

Glu Lys Thr Glu Met Lys Gly Ile Glu Glu Val Val Lys Ile Tyr Met
                805                 810                 815

Asp Asp Leu Ile Ser Ser Ser Leu Val Ile Cys Phe Asn Glu Ile Gly
            820                 825                 830

Asp Ile Leu Asn Phe Gln Ile His Asp Leu Val His Asp Phe Cys Leu
        835                 840                 845

Ile Lys Ala Arg Lys Glu Asn Leu Phe Asp Arg Ile Arg Ser Ser Ala
    850                 855                 860

Pro Ser Asp Leu Leu Pro Arg Gln Ile Thr Ile Asp Tyr Asp Glu Glu
865                 870                 875                 880

Glu Glu His Phe Gly Leu Asn Phe Val Met Phe Asp Ser Asn Lys Lys
                885                 890                 895

Arg His Ser Gly Lys His Leu Tyr Ser Leu Arg Ile Asn Gly Asp Gln
            900                 905                 910

Leu Asp Asp Ser Val Ser Asp Ala Phe His Leu Arg Leu Arg Leu
        915                 920                 925

Ile Arg Val Leu Asp Leu Glu Pro Ser Leu Ile Met Val Asn Asp Ser
    930                 935                 940

Leu Leu Asn Glu Ile Cys Met Leu Asn His Leu Arg Tyr Leu Arg Ile

-continued

```
         945                 950                 955                 960
Arg Thr Gln Val Lys Tyr Leu Pro Phe Ser Phe Ser Asn Leu Trp Asn
                 965                 970                 975
Leu Glu Ser Leu Phe Val Ser Asn Lys Gly Ser Ile Leu Val Leu Leu
                 980                 985                 990
Pro Arg Ile Leu Asp Leu Val Lys Leu Arg Val Leu Ser Val Gly Ala
             995                1000                1005
Cys Ser Phe Phe Asp Met Asp Ala Asp Glu Ser Ile Leu Ile Ala Lys
            1010                1015                1020
Asp Thr Lys Leu Glu Asn Leu Arg Ile Leu Gly Glu Leu Leu Ile Ser
1025                1030                1035                1040
Tyr Ser Lys Asp Thr Met Asn Ile Phe Lys Arg Phe Pro Asn Leu Gln
                1045                1050                1055
Val Leu Gln Phe Glu Leu Lys Glu Ser Trp Asp Tyr Ser Thr Glu Gln
                1060                1065                1070
His Trp Phe Pro Lys Leu Asp Cys Leu Thr Glu Leu Glu Thr Leu Cys
            1075                1080                1085
Val Gly Phe Lys Ser Ser Asn Thr Asn His Cys Gly Ser Ser Val Val
            1090                1095                1100
Thr Asn Arg Pro Trp Asp Phe His Phe Pro Ser Asn Leu Lys Glu Leu
1105                1110                1115                1120
Leu Leu Tyr Asp Phe Pro Leu Thr Ser Asp Ser Leu Ser Thr Ile Ala
                1125                1130                1135
Arg Leu Pro Asn Leu Glu Asn Leu Ser Leu Tyr Asp Thr Ile Ile Gln
                1140                1145                1150
Gly Glu Glu Trp Asn Met Gly Glu Glu Asp Thr Phe Glu Asn Leu Lys
            1155                1160                1165
Phe Leu Asn Leu Arg Leu Leu Thr Leu Ser Lys Trp Glu Val Gly Glu
        1170                1175                1180
Glu Ser Phe Pro Asn Leu Glu Lys Leu Lys Leu Gln Glu Cys Gly Lys
1185                1190                1195                1200
Leu Glu Glu Ile Pro Pro Ser Phe Gly Asp Ile Tyr Ser Leu Lys Phe
                1205                1210                1215
Ile Lys Ile Val Lys Ser Pro Gln Leu Glu Asp Ser Ala Leu Lys Ile
                1220                1225                1230
Lys Lys Tyr Ala Glu Asp Met Arg Gly Gly Asn Asp Leu Gln Ile Leu
            1235                1240                1245
Gly Gln Lys Asn Ile Pro Leu Phe Lys
    1250                1255
```

MI NUCLEIC ACIDS AND USES THEREOF FOR CONFERRING PEST RESISTANCE IN PLANTS

CROSS-REFERENCE TO RELATED APPLICATIONS

This application claims priority to U.S. Provisional Application Serial No. 60/028,191, filed Oct. 10, 1996, which is incorporated herein by reference.

STATEMENT AS TO RIGHTS TO INVENTIONS MADE UNDER FEDERALLY SPONSORED RESEARCH AND DEVELOPMENT

This invention was made with Government support under Grant No. BIR-8929216, awarded by the National Science Foundation and Grant Nos. 88-37234 and 91037300-6339, awarded by the United States Department of Agriculture. The Government has certain rights in this invention.

FIELD OF THE INVENTION

The present invention relates generally to plant molecular biology. In particular, it relates to nucleic acids and methods for conferring pest resistance in plants.

BACKGROUND OF THE INVENTION

Loci conferring disease and pest resistance have been identified in many plant species. Genetic analysis of many plant-pathogen interactions has demonstrated that plants contain loci that confer resistance against specific races of a pathogen containing a complementary avirulence gene. Molecular characterization of these genes should provide means for conferring disease resistance to a wide variety of crop plants.

Plant parasitic nematodes are significant pest in many parts of the world. Especially significant in terms of crop losses are the sedentary endo-parasites, cyst nematodes (Globodera spp. and Heterodera spp.) and root-knot nematodes (Meloidogyne spp.).

A number of plant resistance genes that have been characterized at the molecular level (see, e.g., Staskawicz et al., *Science* 268:661–667 (1995)). The derived amino acid sequences of the most common class all contain leucine-rich repeats (LRR) and nucleotide binding sites (NBS). Examples included RPS2, RPM1 (bacterial resistances in Arabidopsis; Mindrinos et al. *Cell* 78:1089–1099 (1994)); Bent et al. *Science* 265:1856–1860 (1994); Grant et al., *Science* 269:843–846 (1995)), L6 (fungal resistance in flax; Lawrence, et al., *The Plant Cell* 7:1195–1206 (1995)), and N, (virus resistance in tobacco; Whitham, et al., *Cell* 78:1101–1115 (1994); and U.S. Pat. No. 5,571,706).

The NBS is a common motif in several mammalian gene families encoding signal transduction components (e.g., Ras) and is associated with ATP/GTP-binding sites. LRR domains can mediate protein-protein interactions and are found in a variety of proteins involved in signal transduction, cell adhesion and various other functions. LRRs are leucine rich regions often comprising 20–30 amino acid repeats where leucine and other aliphatic residues occur periodically. LRRs can function extracellularly or intracellularly.

Today, nematode and other pests are controlled primarily using chemical pesticides. These compounds are generally very toxic and have been suspected of causing environmental damage. These concerns have prompted efforts to find other methods of controlling nematodes in economically important crop plants. The present invention addresses these and other needs.

SUMMARY OF THE INVENTION

The present invention provides isolated nucleic acid constructs comprising an Mi polynucleotide sequence, which hybridizes to SEQ. ID. NO:1 or to SEQ. ID. NO:2 under stringent conditions. The Mi polynucleotides encode polypeptides which confer resistance to nematodes and other pests. The polypeptides have a leucine rich repeat (LRR) motif and a conserved nucleotide binding site (NBS) as described in Staskawicz et al. *Science* 268:661(1995). The nucleic acid constructs of the invention may further comprise a promoter operably linked to the Mi polynucleotide sequence. The promoter may be a tissue-specific promoter or a constitutive promoter.

The invention further provides transgenic plants comprising a recombinant expression cassette comprising a plant promoter operably linked to an Mi polynucleotide sequence. Although any plant can be used in the invention, tomato plants may be conveniently used.

The invention further provides methods of enhancing resistance to nematodes and other pests in a plant. The methods comprise introducing into the plant a recombinant expression cassette comprising a plant promoter operably linked to an Mi polynucleotide sequence.

Definitions

Units, prefixes, and symbols can be denoted in their SI accepted form. Numeric ranges are inclusive of the numbers defining the range. Unless otherwise indicated, nucleic acids are written left to right in 5' to 3' orientation, respectively. The headings provided herein are not limitations of the various aspects or embodiments of the invention which can be had by reference to the specification as a whole. Accordingly, the terms defined immediately below are more fully defined by reference to the specification as a whole.

As used herein, the term "plant" includes reference to whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants.

As used herein, "pest" includes, but is not limited to, viruses, fungi, nematodes, insects, and bacteria.

As used herein, "heterologous" when used to describe nucleic acids or polypeptides refers to nucleic acids or polypeptides that originate from a foreign species, or, if from the same species, are substantially modified from their original form. For example, a promoter operably linked to a heterologous structural gene is from a species different from that from which the structural gene was derived, or, if from the same species, one or both are substantially modified from their original form.

A polynucleotide or polypeptide is "exogenous to" an individual plant is one which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as an $R_1$ generation transgenic plant. Transgenic plants which arise from sexual cross or by selfing are descendants of such a plant.

As used herein, "Mi gene" or "Mi polynucleotide" is a polynucleotide encoding resistance to plant pests such as viruses, fungi, nematodes, insects, and bacteria, and which hybridizes under stringent conditions and/or has at least 60% sequence identity at the deduced amino acid level to the exemplified sequences provided herein. Mi polynucleotides code Mi polypeptides which comprise LRR motifs and NBS motifs. The Mi polypeptides encoded by Mi genes have at least 55% or 60% sequence identity, typically at least 65 % sequence identity, preferably at least 70% sequence identity, often at least 75 % sequence identity, more preferably at least 80% sequence identity, and most preferably at least 90% sequence identity at the deduced amino acid level relative to the exemplary Mi sequences provided herein.

As used herein, "Mi polynucleotide" includes reference to a contiguous sequence from an Mi gene of at least 18, 20, 25, 30, 40, or 50 nucleotides in length, up to at least about 100 or at least about 200 nucleotides in length. In some embodiments the polynucleotides is preferably at least 100 nucleotides in length, more preferably at least 200 nucleotides in length, most preferably at least 500 nucleotides in length. Thus, a Mi polynucleotide may be an Mi gene or a subsequence thereof.

As used herein, "isolated" includes reference to material which is substantially or essentially free from components which normally accompany or interact with it as found in its naturally occurring environment. The isolated material optionally comprises material not found with the material in its natural environment.

As used herein, "nucleic acid" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

In the expression of transgenes one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional Mi polypeptide, one of skill will recognize that because of codon degeneracy, a number of polynucleotide sequences will encode the same polypeptide. These variants are specifically covered by the term "Mi polynucleotide sequence". In addition, the term specifically includes those full length sequences substantially identical (determined as described below) with an Mi gene sequence which encode proteins that retain the function of the Mi protein. Thus, in the case of Mi genes disclosed here, the term includes variant polynucleotide sequences which have substantial identity with the sequences disclosed here and which encode proteins capable of conferring resistance to nematodes, bacteria, viruses, fungi, insects or other pests on a transgenic plant comprising the sequence.

Two polynucleotides or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a specified contiguous portion of a reference polynucleotide sequence. Sequence comparisons between two (or more) polynucleotides or polypeptides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 55% or 60% sequence identity, generally at least 65 %, preferably at least 70%, often at least 75%, more preferably at least 80% and most preferably at least 90%, compared to a reference sequence using the programs described above (preferably BESTFIT) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 55 % or 60%, preferably at least 70%, more preferably at least 80%, and most preferably at least 95 %. Polypeptides having "sequence similarity" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other under appropriate conditions. Appropriate conditions can be high or low stringency and will be different in different circumstances. Generally, stringent conditions are selected to be about 5° C. to about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 50° C. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code.

Nucleic acids of the invention can be identified from a cDNA or genomic library prepared according to standard procedures and the nucleic acids disclosed here used as a probe. Thus, for example, stringent hybridization conditions will typically include at least one low stringency wash using 0.3 molar salt (e.g., 2×SSC) at 65+ C. The washes are preferably followed by one or more subsequent washes using 0.03 molar salt (e.g., 0.2×SSC) at 50° C., usually 60° C., or more usually 65° C. Nucleic acid probes used to identify the nucleic acids are preferably at least 100 nucleotides in length.

As used herein, a homolog of a particular Mi gene (e.g., the tomato gene disclosed here) is a second gene (either in the same species or in a different species) which encodes a protein having an amino acid sequence having at least 50% identity or 75 % similarity to (determined as described above) to a polypeptide sequence in the first gene product. It is believed that, in general, homologs share a common evolutionary past.

As used herein, "nucleotide binding site" or "nucleotide binding domain" includes reference to a region consisting of kinase-1a, kinase 2, and kinase 3a motifs, which participates in ATP/GTP-binding. Such motifs are described for instance in Yu et al., *Proc. Acad. Sci. USA* 93:11751–11756 (1996); Mindrinos, et al., *Cell* 78:1089–1099 and Shen et al., FEBS, 335:380–385 (1993).

As used herein, "leucine rich region" includes reference to a region that has a leucine content of at least 20% leucine or isoleucine, or 30% of the aliphatic residues: leucine, isoleucine, methionine, valine, and phenylalanine, and arranged with approximate repeated periodicity. The length of the repeat may vary in length but is generally about 20 to 30 amino acids. See, Bent et al., *Science*, 265:1856–1860 (1994). Using the sequences disclosed here and standard nucleic acid hybridization and/or amplification techniques, one of skill can identify members having this region.

As used herein, "tissue-specific promoter" includes reference to a promoter in which expression of an operably linked gene is limited to a particular tissue or tissues.

As used herein "recombinant" includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, a "recombinant expression cassette" is a nucleic acid construct, generated recombinantly or synthetically, with a series of specified nucleic acid elements which permit transcription of a particular nucleic acid in a target cell. The expression vector can be part of a plasmid, virus, or nucleic acid fragment. Typically, the recombinant expression cassette portion of the expression vector includes a nucleic acid to be transcribed, and a promoter.

As used herein, "transgenic plant" includes reference to a plant modified by introduction of a heterologous polynucleotide. Generally, the heterologous polynucleotide is an Mi structural or regulatory gene or subsequences thereof.

As used herein, "hybridization complex" includes reference to a duplex nucleic acid sequence formed by selective hybridization of two single-stranded nucleic acids with each other.

As used herein, "amplified" includes reference to an increase in the molarity of a specified sequence. Amplification methods include the polymerase chain reaction (PCR), the ligase chain reaction (LCR), the transcription-based amplification system (TAS), the self-sustained sequence replication system (SSR). A wide variety of cloning methods, host cells, and in vitro amplification methodologies are well-known to persons of skill.

As used herein, "nucleic acid sample" includes reference to a specimen suspected of comprising Mi resistance genes. Such specimens are generally derived, directly or indirectly, from lettuce tissue.

DESCRIPTION OF THE PREFERRED EMBODIMENTS

Figure 1:
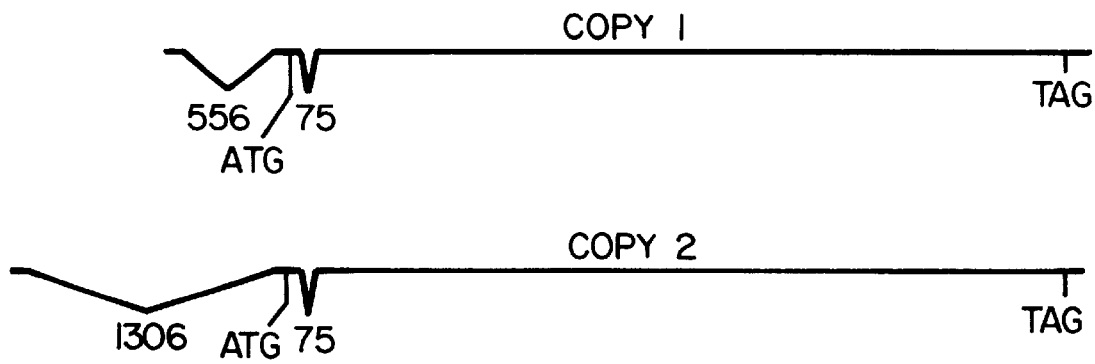
FIG. 1 is a diagram of the mature transcripts of Mi genes of the invention. Mature transcripts are shown as horizontal lines. "V" shapes indicate positions of introns near the 51 ends of each gene. Numbers below the "V"s indicate the size of the introns in nucleotides. Translation start (ATG) and stop (TAG) positions are indicated.

This invention relates to plant Mi genes, such as the Mi genes of tomato exemplified here. Nucleic acid sequences from Mi genes can be used to confer resistance to nematodes and other pests (e.g., insects such as aphids and other sucking, piercing insects) in plants. The invention thus has use over a broad range of types of plants, including species from the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, and, Sorghum.

The nucleic acids of the present invention can be used in marker-aided selection. Marker-aided selection does not require the complete sequence of the gene or precise knowledge of which sequence confers which specificity. Instead, partial sequences can be used as hybridization probes or as the basis for oligonucleotide primers to amplify by PCR or other methods to follow the segregation of chromosome segments containing resistance genes in plants. Because the Mi marker is the gene itself, there can be negligible recombination between the marker and the resistance phenotype. Thus, Mi polynucleotides of the present invention provide an optimal means to DNA fingerprint cultivars and wild germplasm with respect to their disease resistance. This can be used to indicate which germplasm accessions and cultivars carry the same resistance genes. At present, selection of plants (e.g., tomato) for resistance to some diseases is slow and difficult. But linked markers allow indirect selection for such resistance genes.

The Mi polynucleotides also have utility in the construction of disease resistant transgenic plants. This avoids lengthy and sometimes difficult backcrossing programs currently necessary for introgression of resistance. It is also possible to transfer resistance polynucleotides between sexually-incompatible species, thereby greatly increasing the germplasm pool that can be used as a source of resistance genes. Cloning of multiple Mi sequences in a single cassette will allow pyramiding of genes for resistance against multiple isolates of a single pathogen or against multiple pathogens. Once introduced, such a cassette can be manipulated by classical breeding methods as a single Mendelian unit.

Transgenic plants of the present invention can also be constructed using an Mi promoter. The promoter sequences from Mi sequences of the invention can be used with Mi genes or heterologous genes. Thus, Mi promoters can be used to express a variety of genes in the same temporal and spatial patterns and at similar levels to resistance genes.

Preparation of Nucleic Acids of the Invention

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, Cold Spring Harbor Laboratory, Cold Spring Harbor, New York, (1989).

The isolation of Mi genes may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as roots and a cDNA library which contains the Mi gene transcript is prepared from the mRNA. Alternatively, cDNA may be prepared from mRNA extracted from other tissues in which Mi genes or homologs are expressed.

The cDNA or genomic library can then be screened using a probe based upon the sequence of a cloned Mi gene such as the tomato genes disclosed here. Probes may be used to hybridize with genomic DNA or cDNA sequences to isolate homologous genes in the same or different plant species.

Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%.

Alternatively, the nucleic acids of interest can be amplified from nucleic acid samples using amplification techniques. For instance, polymerase chain reaction (PCR) technology to amplify the sequences of the Mi and related genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired MRNA in samples, for nucleic acid sequencing, or for other purposes.

The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium as described earlier.

Appropriate primers and probes for identifying Mi sequences from plant tissues are generated from comparisons of the sequences provided herein. For a general overview of PCR see *PCR Protocols: A Guide to Methods and Applications*. (Innis, M, Gelfand, D., Sninsky, J. and White, T., eds.), Academic Press, San Diego (1990), incorporated herein by reference.

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Mi Proteins

The present invention further provides isolated Mi proteins encoded by the Mi polynucleotides disclosed herein. One of skill will recognize that the nucleic acid encoding a functional Mi protein need not have a sequence identical to the exemplified genes disclosed here. For example, because of codon degeneracy a large number of nucleic acid sequences can encode the same polypeptide. In addition, the polypeptides encoded by the Mi genes, like other proteins, have different domains which perform different functions. Thus, the Mi gene sequences need not be full length, so long as the desired functional domain (e.g., LRR or NBS) of the protein is expressed.

The resistance proteins are at least 50 amino acid residues in length. Typically, the Mi proteins are at least 150 amino acid residues, generally at least 200, preferably at least 500, more preferably at least 1000 amino acids in length. In particularly preferred embodiments, the Mi proteins are of sufficient length to provide resistance to pests when expressed in the desired plants. Generally then, the Mi proteins will be the length encoded by an Mi gene of the present invention. However, those of ordinary skill will appreciate that minor deletions, substitutions, or additions to an Mi protein will typically yield a protein with pest resistance characteristics similar or identical to that of the full length sequence. Thus, full-length Mi proteins modified by 1, 2, 3, 4, or 5 deletions, substitutions, or additions, generally provide an effective degree of pest resistance relative to the full-length protein.

The Mi proteins which provide pest resistance will typically comprise at least one of an LRR or an NBS. Preferably, both are present. LRR and/or NBS regions present in the Mi proteins of the present invention can be provided by Mi genes of the present invention. In some embodiments, the LRR and/or NBS regions are obtained from other pest resistance genes. See, e.g., Yu et al., *Proc. Natl. Acad. Sci. USA*, 93:11751–11756 (1996); Bent et al., *Science*, 265:1856–1860 (1994).

Modified protein chains can also be readily designed utilizing various recombinant DNA techniques well known to those skilled in the art. For example, the chains can vary from the naturally occurring sequence at the primary structure level by amino acid substitutions, additions, deletions, and the like. Modification can also include swapping domains from the proteins of the invention with related domains from other pest resistance genes.

Pests that can be targeted by Mi genes and proteins of the present invention include such nematodes such as Globodera spp., Heterodera spp. and Meloidogyne spp. Other pests which can be targeted by the present invention include aphids such as members of the genus Macrosiphum, bacteria, viruses, and the like.

The present invention also provides antibodies which specifically react with Mi proteins of the present invention under immunologically reactive conditions. An antibody immunologically reactive with a particular antigen can be generated in vivo or by recombinant methods such as selection of libraries of recombinant antibodies in phage or similar vectors. "Immunologically reactive conditions" includes reference to conditions which allow an antibody, generated to a particular epitope of an antigen, to bind to that epitope to a detectably greater degree than the antibody binds to substantially all other epitopes, generally at least two times above background binding, preferably at least five times above background. Immunologically reactive conditions are dependent upon the format of the antibody binding reaction and typically are those utilized in immunoassay protocols.

"Antibody" includes reference to an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding forms of antibodies (e.g., Fab', F(ab')$_2$, Fab, Fv, rIgG, and, inverted IgG). See, Pierce Catalog and Handbook, 1994–1995 (Pierce Chemical Co., Rockford, Ill.). An antibody immunologically reactive with a particular antigen can be generated in vivo or by recombinant methods such as selection of libraries of recombinant antibodies in phage or similar vectors. See, e.g., Huse et al. (1989) *Science* 246:1275–1281; and Ward, et al. (1989) *Nature* 341:544–546; and Vaughan et al. (1996) *Nature Biotechnology*, 14:309–314.

Many methods of making antibodies are known to persons of skill. A number of immunogens are used to produce antibodies specifically reactive to an isolated Mi protein of the present invention under immunologically reactive conditions. An isolated recombinant, synthetic, or native Mi protein of the present invention is the preferred immunogens (antigen) for the production of monoclonal or polyclonal antibodies.

The Mi protein is then injected into an animal capable of producing antibodies. Either monoclonal or polyclonal antibodies can be generated for subsequent use in immunoassays to measure the presence and quantity of the Mi protein. Methods of producing monoclonal or polyclonal antibodies are known to those of skill in the art. See, e.g., Coligan (1991) *Current Protocols in Immunology* Wiley/Greene, NY; and Harlow and Lane (1989) *Antibodies: A Laboratory Manual* Cold Spring Harbor Press, NY); Goding (1986) *Monoclonal Antibodies: Principles and Practice* (2d ed.) Academic Press, New York, N.Y.

Frequently, the Mi proteins and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241.

The antibodies of the present invention can be used to screen plants for the expression of Mi proteins of the present invention. The antibodies of this invention are also used for affinity chromatography in isolating Mi protein.

The present invention further provides Mi polypeptides that specifically bind, under immunologically reactive conditions, to an antibody generated against a defined immunogen, such as an immunogen consisting of the Mi polypeptides of the present invention. Immunogens will generally be at least 10 contiguous amino acids from an Mi polypeptide of the present invention. Optionally, immunogens can be from regions exclusive of the NBS and/or LRR regions of the Mi polypeptides. Nucleic acids which encode such cross-reactive Mi polypeptides are also provided by the present invention. The Mi polypeptides can be isolated from any number plants as discussed earlier. Preferred are species from the family Solanaceae and in particular the genus Lycopersicon.

"Specifically binds" includes reference to the preferential association of a ligand, in whole or part, with a particular target molecule (i.e., "binding partner" or "binding moiety") relative to compositions lacking that target molecule. It is, of course, recognized that a certain degree of non-specific interaction may occur between a ligand and a non-target molecule. Nevertheless, specific binding, may be distinguished as mediated through specific recognition of the target molecule. Typically specific binding results in a much stronger association between the ligand and the target molecule than between the ligand and non-target molecule. Specific binding by an antibody to a protein under such conditions requires an antibody that is selected for its specificity for a particular protein. The affinity constant of the antibody binding site for its cognate monovalent antigen is at least $10^7$, usually at least $10^8$, preferably at least $10^9$, more preferably at least $10^{10}$, and most preferably at least $10^{11}$ liters/mole. A variety of immunoassay formats are appropriate for selecting antibodies specifically reactive with a particular protein. For example, solid-phase ELISA immunoassays are routinely used to select monoclonal antibodies specifically reactive with a protein. See Harlow and Lane (1988) Antibodies, A Laboratory Manual, Cold Spring Harbor Publications, New York, for a description of immunoassay formats and conditions that can be used to determine specific reactivity. The antibody may be polyclonal but preferably is monoclonal. Generally, antibodies cross-reactive to such proteins as RPS2, RPM1 (bacterial resistances in Arabidopsis, L6 (fungal resistance in flax, PRF (resistance to *Pseudomonas syringae* in tomato), and N, (virus resistance in tobacco), are removed by immunoabsorbtion.

Immunoassays in the competitive binding format are typically used for cross-reactivity determinations. For example, an immunogenic Mi polypeptide is immobilized to a solid support. Polypeptides added to the assay compete with the binding of the antisera to the immobilized antigen. The ability of the above polypeptides to compete with the binding of the antisera to the immobilized Mi polypeptide is compared to the immunogenic Mi polypeptide. The percent cross-reactivity for the above proteins is calculated, using standard calculations. Those antisera with less than 10% cross-reactivity with such proteins as RPS2, RPM 1, L6, PRF, and N, are selected and pooled. The cross-reacting antibodies are then removed from the pooled antisera by immunoabsorbtion with these non-Mi resistance proteins.

The immunoabsorbed and pooled antisera are then used in a competitive binding immunoassay to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

Production of Transgenic Plants of the Invention

Isolated sequences prepared as described herein can then be used to provide Mi gene expression and therefore nematode resistance in desired plants. One of skill will recognize that the nucleic acid encoding a functional Mi protein need not have a sequence identical to the exemplified gene disclosed here. In addition, the polypeptides encoded by the Mi genes, like other proteins, have different domains which perform different functions. Thus, the Mi gene sequences need not be full length, so long as the desired functional domain of the protein is expressed. As noted above, the proteins of the invention comprise a leucine rich repeat (LRR) domain.

Modified protein chains can also be readily designed utilizing various recombinant DNA techniques well known to those skilled in the art. For example, the chains can vary from the naturally occurring sequence at the primary structure level by amino acid substitutions, additions, deletions, and the like. Modification can also include swapping domains from the proteins of the invention with related domains from other pest resistance genes.

To use isolated Mi sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988).

A DNA sequence coding for the desired Mi polypeptide, for example a cDNA or a genomic sequence encoding a full length protein, will be used to construct a recombinant expression cassette which can be introduced into the desired plant. An expression cassette will typically comprise the Mi polynucleotide operably linked to transcriptional and translational initiation regulatory sequences which will direct the transcription of the sequence from the Mi gene in the intended tissues of the transformed plant.

For example, a plant promoter fragment may be employed which will direct expression of the Mi in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the Mi gene in a specific tissue or may be otherwise under more precise environmental or developmental control. Such promoters are referred to here as "inducible" promoters. Examples of environmental conditions that may effect transcription by inducible promoters include pathogen attack, anaerobic conditions, or the presence of light.

Examples of promoters under developmental control include promoters that initiate transcription only in certain tissues, such as leaves, roots, fruit, seeds, or flowers. The operation of a promoter may also vary depending on its location in the genome. Thus, an inducible promoter may become fully or partially constitutive in certain locations.

The endogenous promoters from the Mi genes of the invention can be used to direct expression of the genes. These promoters can also be used to direct expression of heterologous structural genes. The promoters can be used, for example, in recombinant expression cassettes to drive expression of genes conferring resistance to any number of pathogens or pests, including fungi, bacteria, and the like.

To identify the promoters, the 5' portions of the clones described here are analyzed for sequences characteristic of promoter sequences. For instance, promoter sequence elements include the TATA box consensus sequence (TATAAT), which is usually 20 to 30 base pairs upstream of the transcription start site. In plants, further upstream from the TATA box, at positions −80 to −100, there is typically a promoter element with a series of adenines surrounding the trinucleotide G (or T) N G. J. Messing et al., in *Genetic Engineering in Plants*, pp. 221–227 (Kosage, Meredith and Hollaender, eds. 1983). Particular promoter sequences are defined below.

If proper polypeptide expression is desired, a polyadenylation region at the 3'-end of the Mi coding region should be included. The polyadenylation region can be derived from the natural gene, from a variety of other plant genes, or from T-DNA.

The vector comprising the sequences from an Mi gene will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Such DNA constructs may be introduced into the genome of the desired plant host by a variety of conventional techniques. For example, the DNA construct may be introduced directly into the genomic DNA of the plant cell using techniques such as electroporation, PEG poration, particle bombardment and microinjection of plant cell protoplasts or embryogenic callus, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* or *Agrobacterium rhizogenes* host vector. The virulence functions of the Agrobacterium host will direct the insertion of the construct and adjacent marker into the plant cell DNA when the cell is infected by the bacteria.

Transformation techniques are known in the art and well described in the scientific and patent literature. The introduction of DNA constructs using polyethylene glycol precipitation is described in Paszkowski et at. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

*Agrobacterium tumefaciens*-meditated transformation techniques are well described in the scientific literature. See, for example Horsch et al. *Science* 233:496–498 (1984), and Fraley et al. *Proc. Natl. Acad. Sci. USA* 80:4803 (1983). Although Agrobacterium is useful primarily in dicots, certain monocots can be transformed by Agrobacterium. For instance, Agrobacterium transformation of rice is described by Hiei et al, *Plant J.* 6:271–282 (1994).

Transformed plant cells which are derived by any of the above transformation techniques can be cultured to regenerate a whole plant which possesses the transformed genotype and thus the desired Mi-controlled phenotype. Such regeneration techniques rely on manipulation of certain phytohormones in a tissue culture growth medium, typically relying on a biocide and/or herbicide marker which has been introduced together with the Mi nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The methods of the present invention are particularly useful for incorporating the Mi polynucleotides into transformed plants in ways and under circumstances which are not found naturally. In particular, the Mi polypeptides may be expressed at times or in quantities which are not characteristic of natural plants.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The effect of the modification of Mi gene expression can be measured by detection of increases or decreases in niRNA levels using, for instance, Northern blots. In addition, the phenotypic effects of gene expression can be detected by measuring nematode or other pest resistance in plants. Suitable assays for determining nematode resistance are well known. For example, Yaghoobi et al., *Theor. App. Gen.* 91457–464 (1995) describes suitable methods for this purpose.

The following Example is offered by way of illustration, not limitation.

EXAMPLE 1
Identification of Mi Genes by DNA Sequence

A genetic locus, Mi, was localized by genetic analysis to a region of the genome of about 65kb. The DNA corresponding to this region was cloned into Bacterial Artificial Chromosome (BAC) vectors. Sequence analysis of a 52 kb BAC3 insert (SEQ ID NO:1) identified three open reading frames (ORFs) encoding proteins with LRR and NBS domains. The presence of early stop codons and deletions in one of these sequences indicate that it is most likely a pseudogene. The sequences of the other two copies, also referred to as Copy 1 and Copy 2, were investigated further. These two ORFs have the following locations: Copy 1 begins at base 45,330, while Copy 2 begins at base 14,662.

Analysis of the Mi Gene Transcripts

By RNA blot analysis, transcripts of approximately 4 kb corresponding to Copy 1 and Copy 2 were found in both resistant and susceptible tomato roots and in leaves of resistant but not susceptible plants. Using standard techniques, cDNA sequences corresponding to full length transcripts of Copy 1 and Copy 2 were obtained (SEQ ID NOS: 2 and 4 respectively). Sequence analysis of the cDNA clones and comparison with their corresponding genomic sequence indicates that each gene contains two introns near its 5' end (FIG. 1). The positions of the introns are conserved between the two genes.

The 1255 and 1257 amino acid (aa) predicted polypeptides encoded by the cDNAs was determined (SEQ ID NO:3 and SEQ ID NO:5). The polypeptides are 91% identical in amino acid sequence and contain structural features similar to several previously characterized plant resistance genes (R genes) of the NBS/LRR superfamily. Comparison of the Mi protein to other members of the NBS/LRR family of R genes revealed that the Prf gene of tomato (Salmeron et al. *Cell* 86:123–133 (1996)) shared the greatest homology (28 % amino acid identity), followed by two other tomato genes 12C-1 and 12C-2 (Ori et al. *Plant Cell* 9:521–532 (1997)) (25% and 26%, respectively) and by the Arabidopsis gene RPM1 (Grant et al. *Science* 269:843–846 (1995)) (24%).

Nematode Resistance Test on Transferred Copies of Mi Genes Copy 1 and Copy 2

A 14.7 kb insert of tomato genomic DNA containing the entire Copy 2 coding region, 4.62 kb of 5' to the transcription start site and 4.77 kb of 3' flanking sequence, was inserted into a binary vector and transferred to *Agrobacterium tumefaciens* using standard techniques. Transgenic tobacco plants and tomato plants from the nematode susceptible line Moneymaker were transformed with the Copy 2 DNA fragment. Four cuttings of each independent transformant were tested for root-knot nematode resistance in a greenhouse assay.

Of the first 11 tomato transformants tested, 8 had acquired resistance to root-knot nematodes (Table 1). This experiment demonstrates that the 14.75 kb DNA insert carrying Copy 2 is sufficient to produce effective nematode resistance when introduced into nematode-susceptible tomato plants by Agrobacterium-mediated transformation. Eighteen progeny plants from a transformant that carried one copy of the Copy 2 clone were tested for resistance to nematodes. The majority of these plants were resistant to root-knot nematodes. This experiment demonstrates that the resistance produced by the introduced Copy 2 gene is heritable.

These experiments also establish the location of the Mi promoter sequence for Copy 2 in SEQ ID NO:1. In particular, they demonstrate that the 4.62 kb 5' flanking sequence contains all the sequences necessary for expression of the Copy 2 gene in tomato plants. This sequence is from nucleotides 10,071 to 14691 in SEQ ID NO:1. For Copy 1, the corresponding sequence is from nucleotides 42,798 to 44,461. Copy 1 and 2 each have the identical sequence (TATATTT) which appears to be a TATA box at 20–30 nucleotides upstream from the transcription start sites.

Tobacco plants did not show resistance in these experiments. The lack of resistance could be explained by the use of the endogenous tomato Mi promoter. Further experiments using promoters known to be functional in tobacco plants should clarify these results.

In addition, a genomic clone of the Copy 1 gene was isolated as a 10.88 kb BglI fragment which contained the entire copy 1 ORF, 1.66 kb of sequence 5' of the putative transcription start site and 435 bp of 3' region. This DNA fragment was inserted into a binary vector and used to transform tobacco and tomato. Plants produced by these experiments are analyzed as described above.

Homologous Genes in Tomato and Other Species

DNA gel blot analysis found Mi genes present in resistant and susceptible line of tomato. Moderate stringency hybridization with a probe from Copy 2 sequence indicates that there are 5 or more copies of closely related sequence present in susceptible tomato and five and more copies in resistant tomato. Low stringency hybridization with DNA from potato and petite Havana tobacco indicates that multiple homologs of the Mi gene are present in these species. The potato hybridization signal (more than 10 bands) remained after high stringency wash, indicating a high degree of conservation of potato genes with similarity to Copy 2. No hybridizing bands were detected in the plant species Arabidopsis at low stringency.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

TABLE 1

Nematode resistance test data on susceptible tomato (cv. Moneymaker) transformed with Mi gene Copy 2.

| Plant | ave. # of egg masses/ plant* | copies of transferred |
|---|---|---|
| transformants: | | |
| 143-1 | 100 | 2 |
| 143-3 | 6 | 2 |
| 143-4 | 95 | 1 |
| 143-7 | 2 | 2 |
| 143-8 | 96 | 1 |
| 143-10 | 1.5 | 4 |
| 143-11 | 5 | 1 |
| 143-13 | 1.5 | 4 |
| 143-16 | 0 | 4 |
| 143-18 | 1 | 4 |
| 143-23 | 2.5 | 1 |
| controls: | | |
| untransformed plants (susc.) | 100 | 0 |
| untransformed Mi plants (res.) | 0 | 0 |

*Egg masses were counted until all were included or 100 was reached. Each data point is the average of 4 or more replicated tests. Assays were carried out as in Jaghoobi et al., Theor. Appl. Genet. 91:457–464 (1995).

What is claimed is:

1. An isolated nucleic acid comprising an Mi polynucleotide sequence capable of conferring pest resistance on a plant, which polynucleotide hybridizes to SEQ ID NO:2 or SEQ ID NO:4 under stringent conditions, wherein the stringent conditions comprise at least one wash in 0.2×SSC at a temperature of at least about 50° C.

2. The nucleic acid of claim 1, wherein the Mi polynucleotide sequence encodes an Mi polypeptide having a leucine rich repeat motif.

3. The nucleic acid of claim 1, wherein the polynucleotide sequence is a full length gene.

4. The nucleic acid of claim 1, wherein the Mi polynucleotide sequence is as shown in SEQ ID NO:2.

5. The nucleic acid of claim 1, wherein the Mi polynucleotide sequence is as shown in SEQ ID NO:4.

6. The nucleic acid of claim 1, further comprising a promoter operably linked to the Mi polynucleotide sequence.

7. The nucleic acid of claim 6, wherein the promoter is a tissue-specific promoter.

8. The nucleic acid of claim 6, wherein the promoter is a constitutive promoter.

9. The nucleic acid of claim 6, wherein the promoter comprises nucleotides 10071 to 14691 of SEQ ID NO:1.

10. An isolated nucleic acid comprising a polynucleotide sequence capable of conferring pest resistance on a plant which hybridizes under stringent conditions to SEQ ID NO:1, wherein the stringent conditions comprise at least one wash in 0.2×SSC at a temperature of at least about 50° C.

11. An isolated nucleic acid comprising a polynucleotide sequence which encodes a polypeptide comprising at least about 1000 consecutive amino acids of SEQ ID NO:3 or SEQ ID NO:5.

12. A nucleic acid construct comprising an Mi polynucleotide sequence capable of conferring pest resistance on a plant, which polynucleotide hybridizes to SEQ ID NO:2 or SEQ ID NO:4 under stringent conditions, wherein the stringent conditions comprise at least one wash in 0.2×SSC at a temperature of at least about 50° C.

13. The nucleic acid construct of claim 12, wherein the Mi polynucleotide sequence encodes an Mi polypeptide having a leucine rich repeat motif.

14. The nucleic acid construct of claim 12, wherein the polynucleotide sequence is a full length gene.

15. The nucleic acid construct of claim 12, wherein the Mi polynucleotide sequence is as shown in SEQ ID NO:2.

16. The nucleic acid construct of claims 12, wherein the Mi polynucleotide sequence is as shown in SEQ ID NO:4.

17. The nucleic acid construct of claim 12, further comprising a promoter operably linked to the Mi polynucleotide sequence.

18. The nucleic acid construct of claim 17, wherein the promoter is a tissue-specific promoter.

19. The nucleic acid construct of claim 17, wherein the promoter is a constitutive promoter.

20. The nucleic acid construct of claim 17, wherein the promoter comprises nucleotides 10071 to 14691 of SEQ ID NO:1.

21. A nucleic acid construct comprising a polynucleotide sequence capable of conferring pest resistance on a plant which hybridizes under stringent conditions to SEQ ID NO:1, wherein the stringent conditions comprise at least one wash in 0.2×SSC at a temperature of at least about 50° C.

22. A nucleic acid construct comprising a polynucleotide sequence which encodes a polypeptide comprising at least about 1000 consecutive amino acids of SEQ ID NO:3 or SEQ ID NO:5.

23. A transgenic plant comprising a recombinant expression cassette comprising a plant promoter operably linked to the nucleic acid of claim 1.

24. The transgenic plant of claim 23, wherein the plant promoter is a heterologous promoter.

25. The transgenic plant of claim 23, wherein the plant promoter comprises nucleotides 10071 to 14691 of SEQ ID NO:1.

26. The transgenic plant of claim 23, wherein the plant is tomato.

27. The transgenic plant of claim 23, wherein the Mi polynucleotide sequence is as shown in SEQ ID NO:2.

28. The transgenic plant of claim 23, wherein the Mi polynucleotide sequence is as shown in SEQ ID NO:4.

29. A method of enhancing resistance to nematodes in a plant, the method comprising introducing into the plant a recombinant expression cassette comprising a plant promoter operably linked to the nucleic acid of claim 1.

30. The method of claim 29, wherein the plant is tomato.

31. The method of claim 29, wherein the Mi polynucleotide is as shown in SEQ ID NO:2 or SEQ ID NO:4.

32. The method of claim 29, wherein the promoter is a tissue-specific promoter.

33. The method of claim 29, wherein the promoter is a consitutive promoter.

34. The method of claim 29, wherein the promoter comprises nucleotides 10071 to 14691 of SEQ ID NO:1.

* * * * *